US009365842B2

(12) United States Patent
Den Haan et al.

(10) Patent No.: US 9,365,842 B2
(45) Date of Patent: Jun. 14, 2016

(54) NUCLEIC ACIDS ENCODING FUNGAL CELLOBIOHYDROLASES FOR EXPRESSION IN YEAST

(75) Inventors: Riaan Den Haan, Durbanville (ZA); Emile Van Zyl, Stellenbosch (ZA); Danie Lagrange, Durbanville (ZA)

(73) Assignee: Stellenbosch University, Stellenbosch (ZA)

( * ) Notice: Subject to any disclaimer, the term of this patent is extended or adjusted under 35 U.S.C. 154(b) by 479 days.

(21) Appl. No.: 12/992,003

(22) PCT Filed: May 11, 2009

(86) PCT No.: PCT/IB2009/005881
§ 371 (c)(1),
(2), (4) Date: Feb. 3, 2011

(87) PCT Pub. No.: WO2009/138877
PCT Pub. Date: Nov. 19, 2009

(65) Prior Publication Data
US 2011/0124074 A1    May 26, 2011

Related U.S. Application Data

(60) Provisional application No. 61/052,213, filed on May 11, 2008.

(51) Int. Cl.
| C07H 21/00 | (2006.01) |
| C12N 15/00 | (2006.01) |
| C12N 9/42  | (2006.01) |
| C12P 7/10  | (2006.01) |

(52) U.S. Cl.
CPC ............. *C12N 9/2437* (2013.01); *C12P 7/10* (2013.01); *C12Y 302/01091* (2013.01); *Y02E 50/16* (2013.01); *Y02P 20/52* (2015.11)

(58) Field of Classification Search
USPC ............. 435/200, 18, 252.3, 320.1; 536/23.1, 536/23.2
See application file for complete search history.

(56) References Cited

U.S. PATENT DOCUMENTS

| 4,683,202 A | 7/1987 | Mullis |
| 8,470,592 B2 * | 6/2013 | Brevnova et al. ........... 435/320.1 |

FOREIGN PATENT DOCUMENTS

| WO | WO 92/03560 A1 | 3/1992 |
| WO | WO 93/24631 A1 | 12/1993 |
| WO | WO 03/000941 A2 | 1/2003 |
| WO | WO 2005/001065 A2 | 1/2005 |
| WO | WO 2007/094852 A2 | 8/2007 |
| WO | WO 2008/064314 A2 | 5/2008 |

OTHER PUBLICATIONS

Gustafsson et al., Trends in Biotechnology 22(7):346-353, 2004.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Bowie, J.U., et al., "Deciphering the Message in Protein Sequences: Tolerance to Amino Acid Substitutions," *Science* 247:1306-1310, Science, United States (1990).
Brutlag, D.L., et al., "Improved Sensitivity of Biological Sequence Database Searches," *Comp. App. Biosci.* 6:237-245, Oxford University Press, United Kingdom (1990).
Cho, K.M., et al., "δ-Integration of Endo/Exo-Glucanase and β-Glucosidase Genes into the Yeast Chromosomes for Direct Conversion of Cellulose to Ethanol," *Enzyme and Microbial Technology* 25:23-30, Elsevier Science Inc., United Kingdom (1999).
Crous, J.M., et al., "Cloning and Expression of an *Aspergillus kawachii* Endo-1,4-β-xylanase Gene in *Saccharomyces cerevisiae*," *Current Genetics* 28:467-473, Springer-Verlag, Germany (1995).
Cunningham, B.C. and Wells, J.A., "High-Resolution Epitope Mapping of hGH-Receptor Interactions by Alanine-Scanning Mutagenesis," *Science* 244:1081-1085, American Association for the Advancement of Science, United States (1989).
Davies, G. & Henrissat, B., "Structures and Mechanisms of Glycosyl Hydrolases," *Structure* 3:853-859, Current Biology Ltd., United States (1995).
Demain, A. L., et al., "Cellulase, Clostridia, and Ethanol," *Microbial. Mol. Biol. Rev.* 69:124-154, American Society for Microbiology, United States (2005).
Den Haan, et al., "Functional Expression of Cellobiohydrolases in *Saccharomyces cerevisiae* Towards One-step Conversion of Cellulose to Ethanol," *Enzyme and Microbial Technology* 40:1291-1299, Elsevier, Holland (2007).
Frohman, M.A., et al., "Rapid Production of Full-length cDNAs from Rare Transcripts: Amplification Using a Single Gene-specific Oligonucleotide Primer," *Proc. Natl. Acad. Sci. USA* 85:8998, National Academy of Sciences, United States (1988).
Fujita, Y., et al., "Synergistic Saccharification, and Direct Fermentation to Ethanol, of Amorphous Cellulose by Use of an Engineered Yeast Strain Codisplaying Three Types of Cellulolytic Enzyme," *Applied and Environmental Microbiology* 70:1207-1212, American Society for Microbiology, United States (2004).
Gassick, A., et al., "Three-dimensional Structure of a Thermostable Native Cellobiohydrolase, CBH IB, and Molecular Characterization of the *cel7* Gene from the Filamentous Fungus, *Talaromyces emersonii*," *Eur. J. Biochem.* 271:4495-4506, John Wiley & Sons, Inc., United States (2004).

(Continued)

*Primary Examiner* — Delia Ramirez
(74) *Attorney, Agent, or Firm* — Nutter McClennen & Fish LLP

(57) ABSTRACT

The present invention provides for heterologous expression of polypeptides encoded by wild-type and codon-optimized variants of cbh1 and/or cbh2 from the fungal organisms *Talaromyces emersonii* (*T. emersonii*), *Humicola grisea* (*H. grisea*), *Thermoascus aurantiacus* (*T. aurantiacus*), and *Trichoderma reesei* (*T. reesei*) in host cells, such as the yeast *Saccharomyces cerevisiae*. The expression in such host cells of the corresponding genes, and variants and combinations thereof, result in improved specific activity of the expressed cellobiohydrolases. Thus, such genes and expression systems are useful for efficient and cost-effective consolidated bioprocessing systems.

63 Claims, 26 Drawing Sheets

(56) References Cited

OTHER PUBLICATIONS

Figure 1:
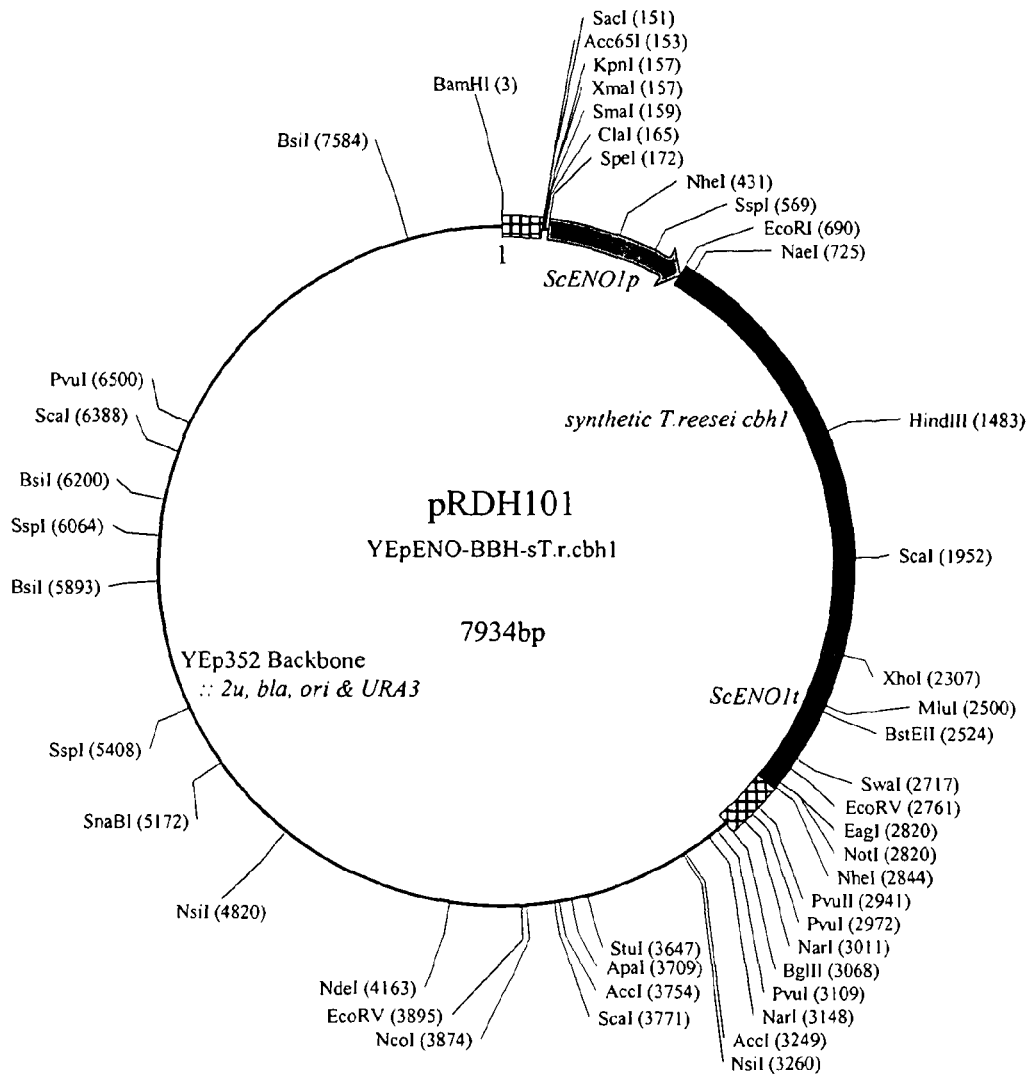

Hahn-Hägerdal, B., et al., "Metabolic Engineering of *Saccharomyces cerevisiae* for Xylose Utilization," *Adv. in Biochem. Eng. Biotechnol.* 73:53-84, Springer-Verlag, Germany (2001).
Henrissat, B., et al., "Conserved Catalytic Machinery and the Prediction of a Common Fold for Several Families of Glycosyl Hyydrolases," *Proc. Natl. Acad. Sci.* 92: 7090-7094, National Academy of Sciences, United States (1995).
Hong, J., et al., "Cloning of a Gene Encoding Thermostable Cellobiohydrolase from *Thermoascus aurantiacus* and its Expression in Yeast," *Applied Microbiology and Biotechnology* 63:42-50, Springer-Verlag, Germany (2003).
Kotula, L. & Curtis, P.J.., "Evaluation of Foreign Gene Codon Optimization in Yeast: Expression of a Mouse IG Kappa Chain," *Nature Biotechnology* 9:1386-1389, Nature Publishing Group, United States (1991).
La Grange, D.C., et al., "Expression of a *Trichoderma reesei* β-Xylanase Gene (*XYN2*) in *Saccharomyces cerevisiae*," *Appl. Environ. Microbiol.* 62:1036-1044, American Society for Microbiology, United States (1996).
Loh, E.Y., et al., "Polymerase Chain Reaction with Single-Sided Specificity: Analysis of T Cell Receptor δ Chain," *Science* 243:217, American Association for the Advancement of Science, United States (1989).
McBride, J.E., et al., "Utilization of Cellobiose by Recombinant β-Glucosidase-Expressing Strains of *Saccharomyces cerevisiae*: Characterization and Evaluation of the Sufficiency of Expression," *Enzyme and Microbial Technology* 37:93-101, Elsevier, Holland (2005).
Nakamura, Y., et al., "Codon Usage Tabulated from International DNA Sequence Databases: Status for the Year 2000," *Nucl. Acids Res.* 28:292, Oxford University Press, United Kingdom (2000).
Ohara, O., et al., "One-sided Polymerase Chain Reaction: The Amplification of cDNA," *Proc. Natl. Acad. Sci. USA* 86:5673-5677, National Academy of Sciences, United States (1989).
Penttilä, M.E., et al., "Efficient secretion of two fungal cellobiohydrolases by *Saccharomyces cerevisiae*," *Gene* 63:103-112, Elsevier B.V., United Kingdom (1988).
Sun, Y. & Cheng, J., "Hydrolysis of Lignocellulosic Materials for Ethanol Production: A Review," *Bioresource Technol.* 83:1-11, Elsevier, Holland (2002).
Tabor, S. & Richardson, C.C., "A Bacteriophage T7 RNA Polymerase/Promoter System for Controlled Exclusive Expression of Specific Genes," *Proc. Natl. Acad. Sci. USA* 82:1074-1078, National Academy of Sciences, United States (1985).
Van Rensburg, P., et al., "Engineering Yeast for Efficient Cellulose Degradation," *Yeast* 14:67-76, Jon Wiley & Sons, Ltd., United States (1998).
Van Rooyen, R., et al., "Construction of Cellobiose-Growing and Fermenting *Saccharomyces cerevisiae* Strains," *J. Biotechnol.* 120:284-295, Elsevier, Holland (2005).
Van Zyl, W.H, et al., "Consolidated Bioprocessing for Bioethanol Production using *Saccharomyces cereviside*," *Advances in Biochemical Engineering Biotechnology* 108:205-235, Springer-Verlag, Germany (2007).
Walker, G.T., et al., "Isothermal in vitro Amplification of DNA by a Restriction Enzyme/DNA Polymerase System," *Proc. Natl. Acad. Sci. USA* 89:392-396, National Academy of Sciences, United States (1992).
International Search Report for International Application No. PCT/IB2009/005881, European Patent Office, Rijswijk, mailed on Nov. 11, 2009.
Written Opinion of the International Searching Authority for International Application No. PCT/IB2009/005881, European Patent Office, Rijswijk, filed on Nov. 5, 2009.
EMBL Accession No. AY081766, Collins, C.M., et al., Submitted (Mar. 4, 2002) Biochemistry, National University of Ireland, Ireland.
EMBL Accession No. AF421954, Hong, J., et al., Submitted (Sep. 21, 2001) Graduate School of Agriculture, Kyoto University, Japan.
EMBL Accession No. AY075018, Collins, C.M., et al., Submitted (Jan. 23, 2002) Biochemistry, National University of Ireland, Ireland.
EMBL Accession No. X17258, Radford, A., Submitted (Dec. 7, 1989) The University of Leeds, Department of Genetics, Leeds.
EMBL Accession No. AF478686, Hong, J., et al., Submitted (Jan. 29, 2002) Graduate School of Agriculture, Kyoto University, Japan.
EMBL Accession No. AF439936, Collins, C.M., et al., Submitted (Oct. 25, 2001) Biochemistry, National University of Ireland, Ireland.
EMBL Accession No. E00389, Shiyaron, P.S., et al., created (Oct. 3, 1997) Cetus Corp., California, United States.
EMBL Accession No. M16190, Teeri, T.T., et al., created (Jul. 16, 1988) *Gene* 51:43-52 (1987).
UNIPROT Accession No. Q8TFL9, Collins, C.M., et al., created (Jun. 1, 2002) Biochemistry, National University of Ireland, Ireland.
UNIPROT Accession No. P15828, de Oliviera Alzevedo, M. and Radford, A., created (Apr. 1, 1990), The University of Leeds, Department of Genetics, Leeds.
UNIPROT Accession No. Q96UR5, Hong, J., et al., created (Dec. 1, 2001), Graduate School of Agriculture, Kyoto University, Japan.
UNIPROT Accession No. Q8NIB5, Collins, C.M., et al., created (Oct. 1, 2002) Biochemistry, National University of Ireland, Ireland.
GSN Accession No. ADW02257 Larenas, E.A., et al., Submitted (Mar. 24, 2005) Genencor Int. Inc., United States.
GSN Accession No. ADW02258, Larenas, E.A., et al., Submitted (Mar. 24, 2005) Genencor Int. Inc., United States.
Grassick, A., et al., "Crystallization and preliminary crystallographic analysis of the catalytic domain cellobiohydrolase I from *Talaromyces emersonii*," *Acta Crystallpgraphica Section D* D59:1283-1284, International Union of Crystallography, Denmakr (2003).
Kooistra, R., et al., "Efficient gene targeting in *Kluyveromyces lactis*," *Yeast* 21: 781-792, John Wiley & Sons, Ltd., England (2004).
Setati, M.E., et al., "Expression of *the Aspergillus aculeatus* Endo-β-1,4-mannanase Encoding Gene (*manI*) in *Saccharomyces cerevisiae* and Characterization of the Recombinant Enzyme," *Protein Expression and Purification* 21:105-114, Academic Press, United States (2001).

* cited by examiner

NUCLEIC ACIDS ENCODING FUNGAL CELLOBIOHYDROLASES FOR EXPRESSION IN YEAST

BACKGROUND OF THE INVENTION

Lignocellulosic biomass is widely recognized as a promising source of raw material for production of renewable fuels and chemicals. The primary obstacle impeding the more widespread production of energy from biomass feedstocks is the general absence of low-cost technology for overcoming the recalcitrance of these materials to conversion into useful fuels. Lignocellulosic biomass contains carbohydrate fractions (e.g., cellulose and hemicellulose) that can be converted into ethanol. In order to convert these fractions, the cellulose and hemicellulose must ultimately be converted or hydrolyzed into monosaccharides; it is the hydrolysis that has historically proven to be problematic.

Biologically mediated processes are promising for energy conversion, in particular for the conversion of lignocellulosic biomass into fuels. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pre-treated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

Three major types of enzymatic activities are required for native cellulose degradation: The first type are endoglucanases (1,4-β-D-glucan 4-glucanohydrolases; EC 3.2.1.4). Endoglucanases cut at random in the cellulose polysaccharide chain of amorphous cellulose, generating oligosaccharides of varying lengths and consequently new chain ends. The second type are exoglucanases, including cellodextrinases (1,4-β-D-glucan glucanohydrolases; EC 3.2.1.74) and cellobiohydrolases (1,4-β-D-glucan cellobiohydrolases; EC 3.2.1.91). Exoglucanases act in a processive manner on the reducing or non-reducing ends of cellulose polysaccharide chains, liberating either glucose (glucanohydrolases) or cellobiose (cellobiohydrolase) as major products. Exoglucanases can also act on microcrystalline cellulose, presumably peeling cellulose chains from the microcrystalline structure. The third type are β-glucosidases (β-glucoside glucohydrolases; EC 3.2.1.21). β-Glucosidases hydrolyze soluble cellodextrins and cellobiose to glucose units.

A variety of plant biomass resources are available as lignocellulosics for the production of biofuels, notably bioethanol. The major sources are (i) wood residues from paper mills, sawmills and furniture manufacturing, (ii) municipal solid wastes, (iii) agricultural residues and (iv) energy crops. Preconversion of particularly the cellulosic fraction in these biomass resources (using either physical, chemical or enzymatic processes) to fermentable sugars (glucose, cellobiose and cellodextrins) would enable their fermentation to bioethanol, provided the necessary fermentative micro-organism with the ability to utilize these sugars is used.

On a world-wide basis, $1.3 \times 10^{10}$ metric tons (dry weight) of terrestrial plants are produced annually (Demain, A. L., et al., *Microbiol. Mol. Biol. Rev.* 69, 124-154 (2005)). Plant biomass consists of about 40-55% cellulose, 25-50% hemicellulose and 10-40% lignin, depending whether the source is hardwood, softwood, or grasses (Sun, Y. and Cheng, J., *Bioresource Technol.* 83, 1-11 (2002)). The major polysaccharide present is water-insoluble, cellulose that contains the major fraction of fermentable sugars (glucose, cellobiose or cellodextrins).

Bakers' yeast (*Saccharomyces cerevisiae*) remains the preferred micro-organism for the production of ethanol (Hahn-Hagerdal, B., et al., *Adv. Biochem. Eng. Biotechnol.* 73, 53-84 (2001)). Attributes in favor of this microbe are (i) high productivity at close to theoretical yields (0.51 g ethanol produced/g glucose used), (ii) high osmo- and ethanol tolerance, (iii) natural robustness in industrial processes, (iv) being generally regarded as safe (GRAS) due to its long association with wine and bread making, and beer brewing. Furthermore, *S. cerevisiae* exhibits tolerance to inhibitors commonly found in hydrolyzates resulting from biomass pretreatment. The major shortcoming of *S. cerevisiae* is its inability to utilize complex polysaccharides such as cellulose, or its break-down products, such as cellobiose and cellodextrins.

Genes encoding cellobiohydrolases in *T. reesei* (cbh1 and cbh2), *A. niger* (cbhA and cbhB) and *P. chrysosporium* (cbh1-4) have been cloned and described. The proteins encoded by these genes are all modular enzymes containing a catalytic domain linked via a flexible liner sequence to a cellulose-binding module. Cbh1, Cbh2, CbhB and Cbh1-4 are family 7 glycosyl hydrolases. Glycosyl hydrolases are a widespread group of enzymes that hydrolyse the glycosidic bond between two or more carbohydrates, or between a carbohydrate and a non-carbohydrate moiety. A classification system for glycosyl hydrolases, based on sequence similarity, has led to the definition of 85 different families (Henrissat, B. et al., *Proc. Natl. Acad. Sci.* 92:7090-7094 (1995); Davies, G. and Henrissat, B., *Structure* 3: 853-859 (1995)). Glycoside hydrolase family 7 (GHF7) comprises enzymes with several known activities including endoglucanase (EC:3.2.1.4) and cellobiohydrolase (EC:3.2.1.91). These enzymes were formerly known as cellulase family C. Glycosyl hydrolase family 7 enzymes have a 67% homology at the amino acid level, but the homology between any of these enzymes and the glycosyl hydrolase family 6 CBH2 is less than 15%.

Exoglucanases and cellobiohydrolases play a role in the conversion of cellulose to glucose by cutting the disaccharide cellobiose from the nonreducing end of the cellulose polymer chain. Structurally, cellulases and xylanases generally consist of a catalytic domain joined to a cellulose-binding module (CBM) via a linker region that is rich in proline and/or hydroxy-amino acids. In some cases, however, cellulases do not contain a CBM, and only contain a catalytic domain. Examples of such CBM-lacking cellulases include Cbhs from *Humcola grisea, Phanerochaete chrysosporium* and *Aspergillus niger*. Grassick et al., *Eur. J. Biochem.* 271: 4495-4506 (2004). In type I exoglucanases, the CBM domain is found at the C-terminal extremity of these enzyme (this short domain forms a hairpin loop structure stabilised by 2 disulphide bridges).

Classically, exoglucanases such as the cellobiohydrolases (Cbh) possess tunnel-like active sites, which can only accept a substrate chain via its terminal regions. These exo-acting Cbh enzymes act by threading the cellulose chain through the tunnel, where successive cellobiose units are removed in a sequential manner. Sequential hydrolysis of a cellulose chain is termed 'processivity.'

Two of the better characterized Cbh members of GH7 are Cel7A from *T. reesei* and Cel7D (Cbh58) from *P. chrysosporium*. Both Cbhs consist of two β-sheets that pack face-to-face to form a β-sandwich. Cel7A from *T. reesei* is composed of long loops, one face of the sandwich that form a cellulose-binding tunnel. The catalytic residues are glutamate 212 and 217, which are located on opposite sides of the active site.

Several genes from the GH7 family of enzymes have been cloned and characterized from a variety of fungal sources, including *H. grisea, T. reesei, T. aurantiacus, Penicillium janthinellum, P. chrysospirum* and *Aspergillus* species. In addition, Cbh enzymes from *T. emersonii*, including Cbh1, have been isolated and characterized. The *T. emersonii* Cbh1 contains a secretory signal peptide and a catalytic domain. The CBM and linker region that are characteristic of some other GH family members are not present in the molecule.

With the aid of recombinant DNA technology, several of these heterologous cellulases from bacterial and fungal sources have been transferred to *S. cerevisiae*, enabling the degradation of cellulosic derivatives (Van Rensburg, P., et al., Yeast 14, 67-76 (1998)), or growth on cellobiose (Van Rooyen, R., et al., *J. Biotech.* 120, 284-295 (2005)); McBride, J. E., et al., *Enzyme Microb. Techol.* 37, 93-101 (2005)).

Related work was described by Fujita, Y., et al., (*Appl. Environ. Microbiol.* 70, 1207-1212 (2004)) where cellulases immobilised on the yeast cell surface had significant limitations. Firstly, Fujita et al. were unable to achieve fermentation of amorphous cellulose using yeast expressing only recombinant Bgl1 and EgII. A second limitation of the Fujita et al. approach was that cells had to be pre-grown to high cell density on standard carbon sources before the cells were useful for ethanol production using amorphous cellulose (e.g., Fujita et al. teaches high biomass loadings of ~15 g/L to accomplish ethanol production).

As noted above, ethanol producing yeast such as *S. cerevisiae* require addition of external cellulases when cultivated on cellulosic substrates, such as pre-treated wood, because this yeast does not produce endogenous cellulases. Expression of fungal cellulases such as *T. reesei* Cbh1 and Cbh2 in yeast *S. cerevisiae* have been shown to be functional. Den Haan, R., et al., "Functional expression of cellobiohydrolases in *Saccharomyces cerevisiae* towards one-step conversion of cellulose to ethanol," *Enzyme and Microbial Technology* 40:1291-1299 (2007). However current levels of expression and specific activity of cellulases heterologously expressed in yeast are still not sufficient to enable growth and ethanol production by yeast on cellulosic substrates without externally added enzymes. While studies have shown that perhaps certain cellulases, such as *T. reesei* Cbh1 have specific activity when heterologously expressed, there remains a significant need for improvement in the amount of Cbh activity expressed in order to attain the goal of achieving a consolidated bioprocessing (CBP) system capable of efficiently and cost-effectively converting cellulosic substrates to ethanol.

In order to address the limitations of heterologous Cbh expression in consolidated bioprocessing systems, the present invention provides for heterologous expression of wild-type and codon-optimized variants of Cbh1 and/or Cbh2 from the fungal organisms *Talaromyces emersonii* (*T. emersonii*), *Humicola grisea* (*H. grisea*), *Thermoascus aurantiacus* (*T. aurantiacus*), and *Trichoderma reesei* (*T. reesei*) in host cells, such as the yeast *Saccharomyces cerevisiae*. The expression in such host cells of the corresponding genes, and variants and combinations thereof, result in improved specific activity of the expressed cellobiohydrolases. Thus, such genes and expression systems are useful for efficient and cost-effective consolidated bioprocessing systems.

BRIEF SUMMARY OF THE INVENTION

The present invention provides for the heterologous expression of a *T. emersonii, H. grisea, T. aurantiacus* or *T. reesei* Cbh1 or Cbh2 in host cells, such as the yeast *Saccharomyces cerevisiae*.

The Cbh1 and Cbh2 expressed in host cells of the present invention is encoded by a wild-type or codon-optimized *T. emersonii, H. grisea, T. aurantiacus* or *T. reesei* cbh1 or cbh2. Thus, the present invention further provides for an isolated polynucleotide comprising a nucleic acid at least about 70%, 75%, or 80% identical, at least about 90% to about 95% identical, or at least about 96%, 97%, 98%, 99% or 100% identical to a wild-type or codon optimized *T. emersonii, H. grisea, T. aurantiacus* or *T. reesei* cbh1 or cbh2. In particular aspects, the *T. emersonii, H. grisea, T. aurantiacus* or *T. reesei* cbh1 or cbh2 is selected from the group consisting of SEQ ID NOs:1-10 and 15-16, or fragments, variants, or derivatives thereof.

In additional aspects, the present invention encompasses an isolated polynucleotide comprising a nucleic acid that is 70%, 75%, or 80% identical, at least about 90% to about 95% identical, or at least about 96%, 97%, 98%, 99% or 100% identical to a nucleic acid encoding a functional or structural domain of *T. emersonii, H. grisea, T. aurantiacus* or *T. reesei* cbh1 or cbh2 as set forth above. Domains of the present invention include a catalytic domain or a cellulose binding module (CBM).

In further aspects, the present invention encompasses polypeptides which comprise, or alternatively consist of, an amino acid sequence which is at least 80%, 85%, 90%, 95%, 96%, 97%, 98%, 99% identical to a *T. emersonii, H. grisea, T. aurantiacus* or *T. reesei* Cbh1 or Cbh2, or domain, fragment, variant, or derivative thereof. In particular embodiments, the *T. emersonii, H. grisea, T. aurantiacus* or *T. reesei* Cbh1 or Cbh2 is selected from the group consisting of SEQ ID NOs: 11-14 or 17-18.

In further aspects, the present invention encompasses vectors comprising a polynucleotide of the present invention. Such vectors include plasmids for expression in yeast, such as the yeast *Saccharomyces cerevisiae*. Yeast vectors can be YIp (yeast integrating plasmids), YRp (yeast replicating plasmids), YCp (yeast replicating plasmids with cetromere (CEN) elements incorporated), YEp (yeast episomal plasmids), or YLp (yeast linear plasmids). In certain aspects, these plasmids contain two types of selectable genes: plasmid-encoded drug-resistance genes and cloned yeast genes, where the drug resistant gene is typically used for selection in bacterial cells and the cloned yeast gene is used for selection in yeast. Drug-resistance genes include ampicillin, kanamycin, tetracycline, neomycin. Cloned yeast genes include HIS3, LEU2, LYS2, TRP1, URA3 and TRP1.

In certain embodiments, the vector comprises a (1) a first polynucleotide, where the first polynucleotide encodes for a *T. emersonii, H. grisea, T. aurantiacus*, or *T. reesei* Cbh1 or Cbh2, or domain, fragment, variant, or derivative thereof; and (2) a second polynucleotide, where the second polynucleotide encodes for a *T. emersonii, H. grisea, T. aurantiacus*, or *T. reesei* CBH1 or CBH2, or domain, fragment, variant, or derivative thereof.

In certain additional embodiments, the vector comprises a first polynucleotide encoding for a *T. emersonii* cbh1, *H. grisea* cbh1, or *T. aurantiacusi* cbh1, *T. emersonii* cbh1 and a second polynucleotide encoding for the CBM domain of *T. reesei* cbh1 or *T. reesei* cbh2. In particular embodiments, the vector comprises a first polynucleotide and a second polynucleotide, where the first polynucleotide is *T. emersonii* cbh1 and the second polynucleotide encodes for a CBM from *T. reesei* Cbh1 or Cbh2. In further embodiments, the first and second polynucleotides are in the same orientation, or the second polynucleotide is in the reverse orientation of the first polynucleotide. In additional embodiments, the first polynucleotide is either N-terminal or C-terminal to the second polynucleotide. In certain other embodiments, the first polynucleotide and/or the second polynucleotide are encoded by codon-optimized polynucleotides, for example, polynucleotides codon-optimized for *S. cerevisiae*. In additional embodiments, the first polynucleotide is a codon-optimized *T. emersonii* cbh1 and the second polynucleotide encodes for a codon-optimized CBM from *T. reesei* Cbh1 or Cbh2.

In particular embodiments, the vector of the present invention is selected from the group consisting of pRDH101, pRDH103-112, pRDH118-121, pRDH123-129 and pDLG116-118.

The present invention further provides for a host cell comprising a polynucleotide, a polypeptide, or a vector of the present invention from which a *T. emersonii, H. grisea, T. aurantiacus* or *T. reesei* Cbh1 or Cbh2 is heterologously expressed. In certain aspects, the host cell is a yeast such as *Saccharomyces cerevisiae*. In addition embodiments, the host cell further comprises at least one or more heterologously expressed endoglucanase polypeptides and/or at least one or more heterologously expressed β-glucosidase polypeptides and/or at least one or more heterologously expressed exoglucanase polypeptides. In particular aspects, the endoglucanase polypeptide is a *T. reesei* Eg1. In additional aspects the β-glucosidase polypeptide is a *S. fibuligera* Bgl1.

The present invention further provides for a method for hydrolyzing a cellulosic substrate, comprising contacting said cellulosic substrate with a host cell according to the present invention. In certain aspects, the cellulosic substrate is of a lignocellulosic biomass. Heterologous expression of *T. emersonii, H. grisea, T. aurantiacus* or *T. reesei* Cbh1 or Cbh2 in host cells will augment cellulose hydrolysis and facilitate ethanol production by those host cells on cellulosic substrates.

BRIEF DESCRIPTION OF THE DRAWINGS/FIGURES

FIG. 1. Plasmid map of pRDH101. The pRDH101 plasmid is the YEpENOBBH vector backbone containing synthetic (codon-optimized) *T. reesei* cbh1.

Figure 2:
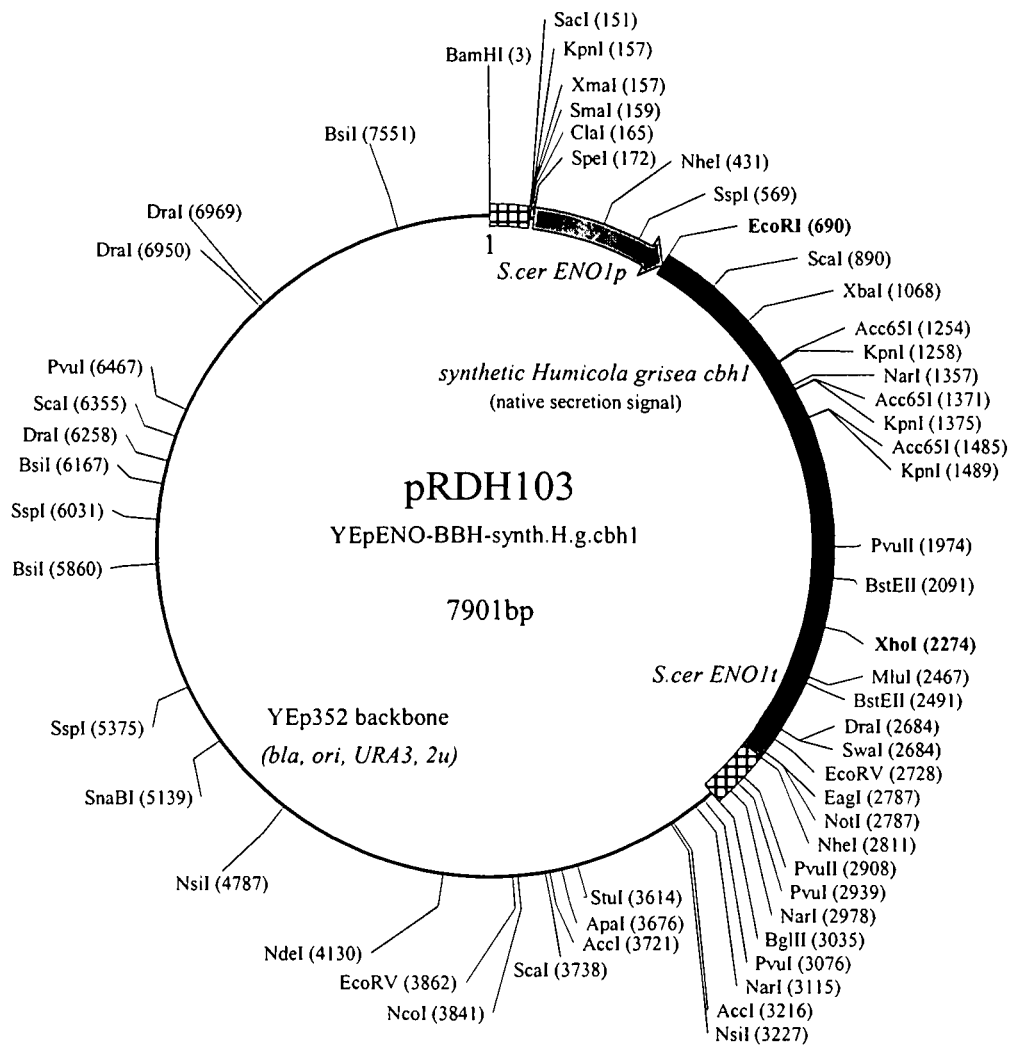

FIG. 2. Plasmid map of pRDH103. The pRDH103 plasmid is the YEpENOBBH vector backbone containing synthetic (codon-optimized) *H. grisea* cbh1.

Figure 3:
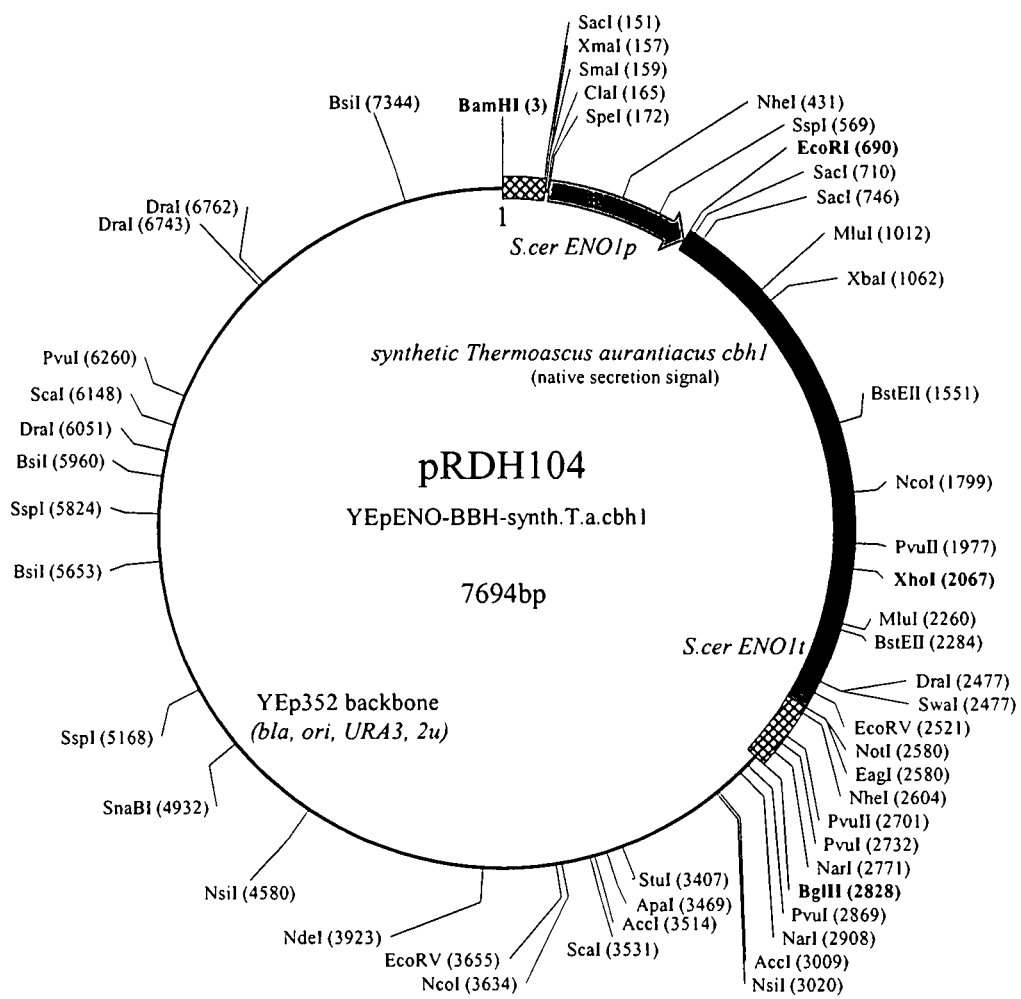

FIG. 3. Plasmid map of pRDH104. The pRDH104 plasmid is the YEpENOBBH vector backbone containing synthetic (codon-optimized) *T. aurantiacus* cbh1.

Figure 4:
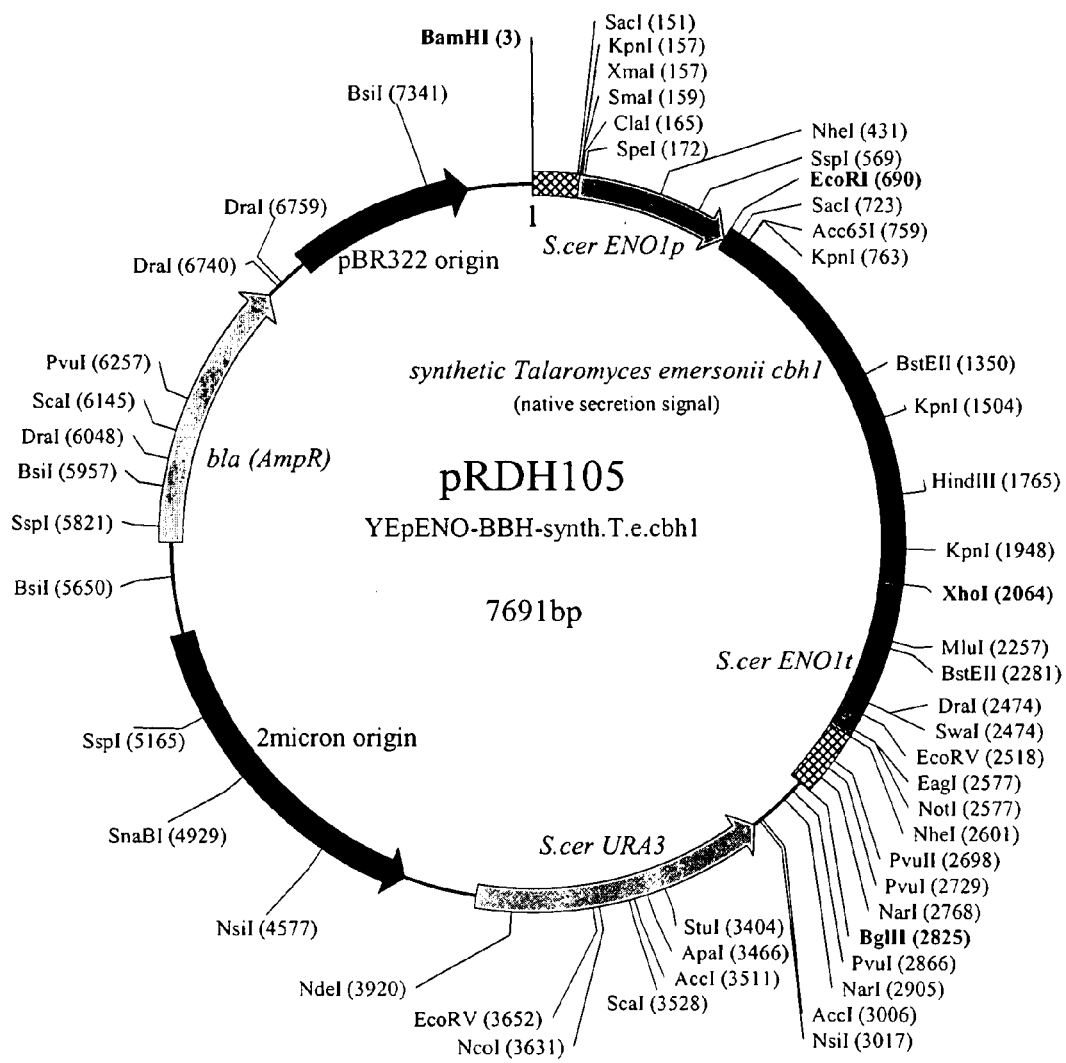

FIG. 4. Plasmid map of pRDH105. The pRDH105 plasmid is the YEpENOBBH vector backbone containing synthetic (codon-optimized) *T. emersonii* cbh1.

Figure 5:
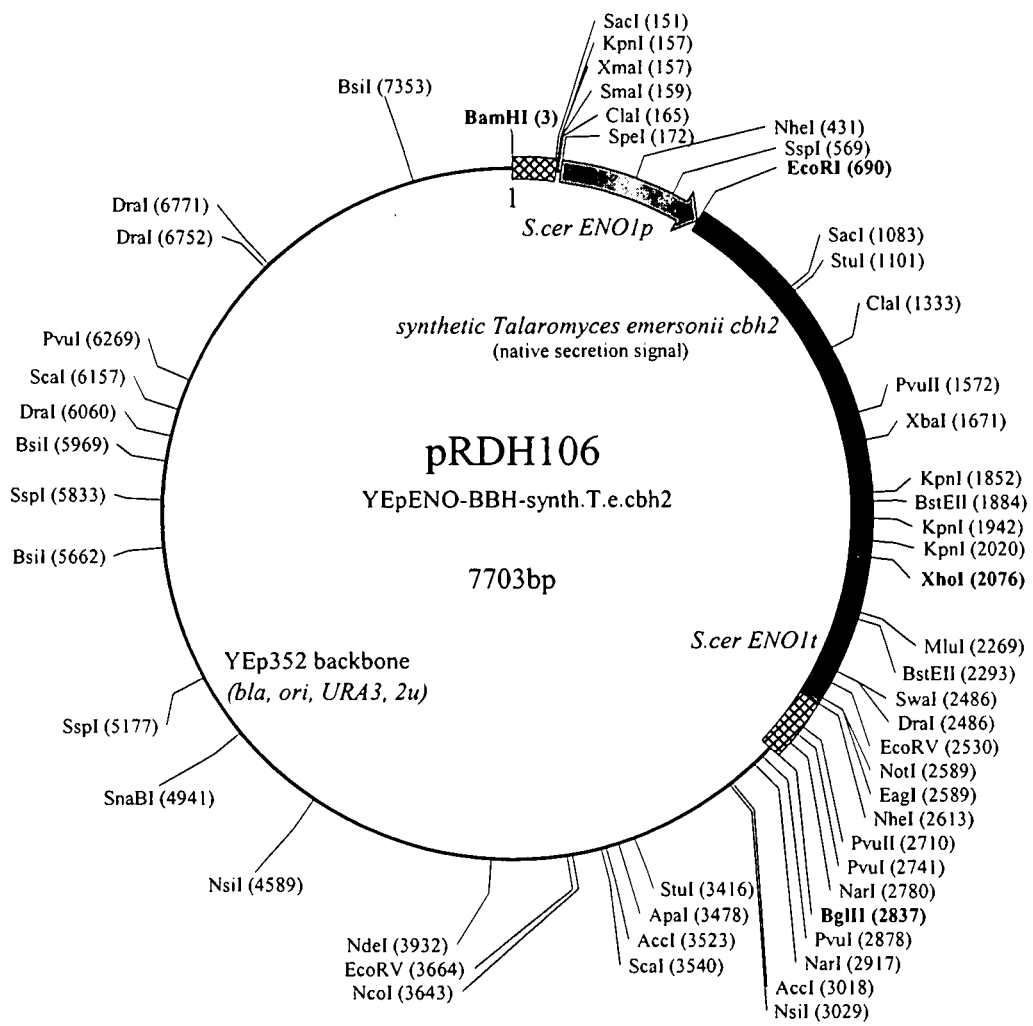

FIG. 5. Plasmid map of pRDH106. The pRDH106 plasmid is the YEpENOBBH vector backbone containing synthetic (codon-optimized) *T. reesei* cbh2.

Figure 6:
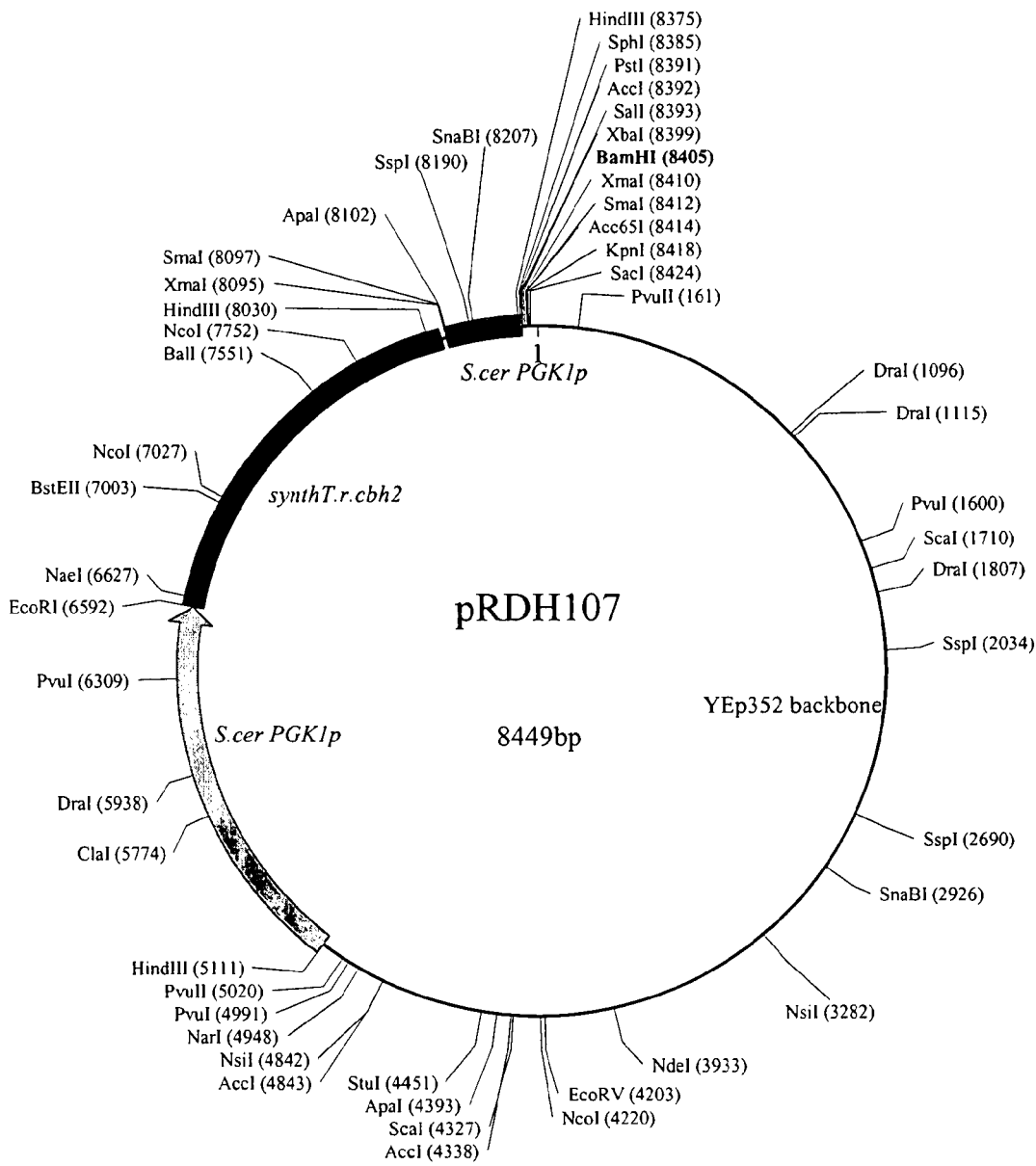

FIG. 6. Plasmid map of pRDH107. The pRDH107 plasmid is the pJC1 vector backbone containing synthetic (codon-optimized) *T. reesei* cbh2.

Figure 7:
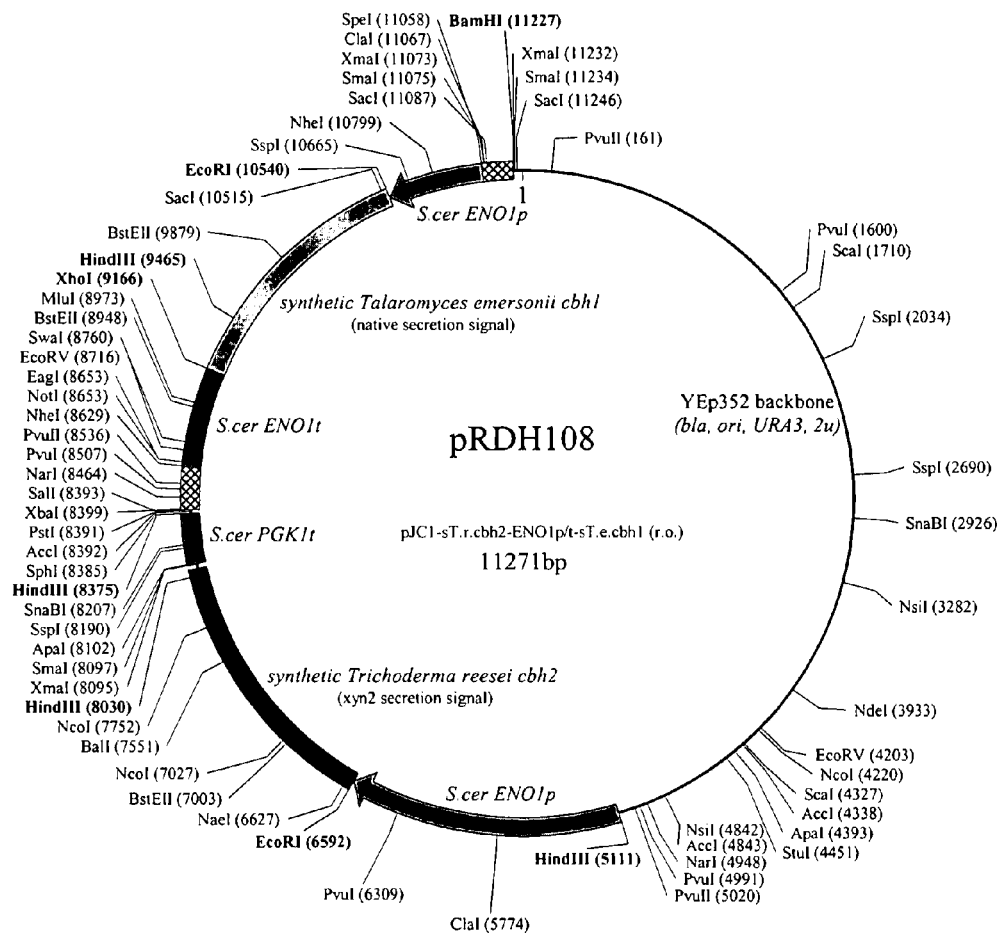

FIG. 7. Plasmid map of pRDH108. The pRDH108 plasmid is the pJC1 vector backbone containing synthetic (codon-optimized) *T. reesei* cbh2 and synthetic (codon-optimized) *T. emersonii* cbh1 in the reverse orientation to one another.

Figure 8:
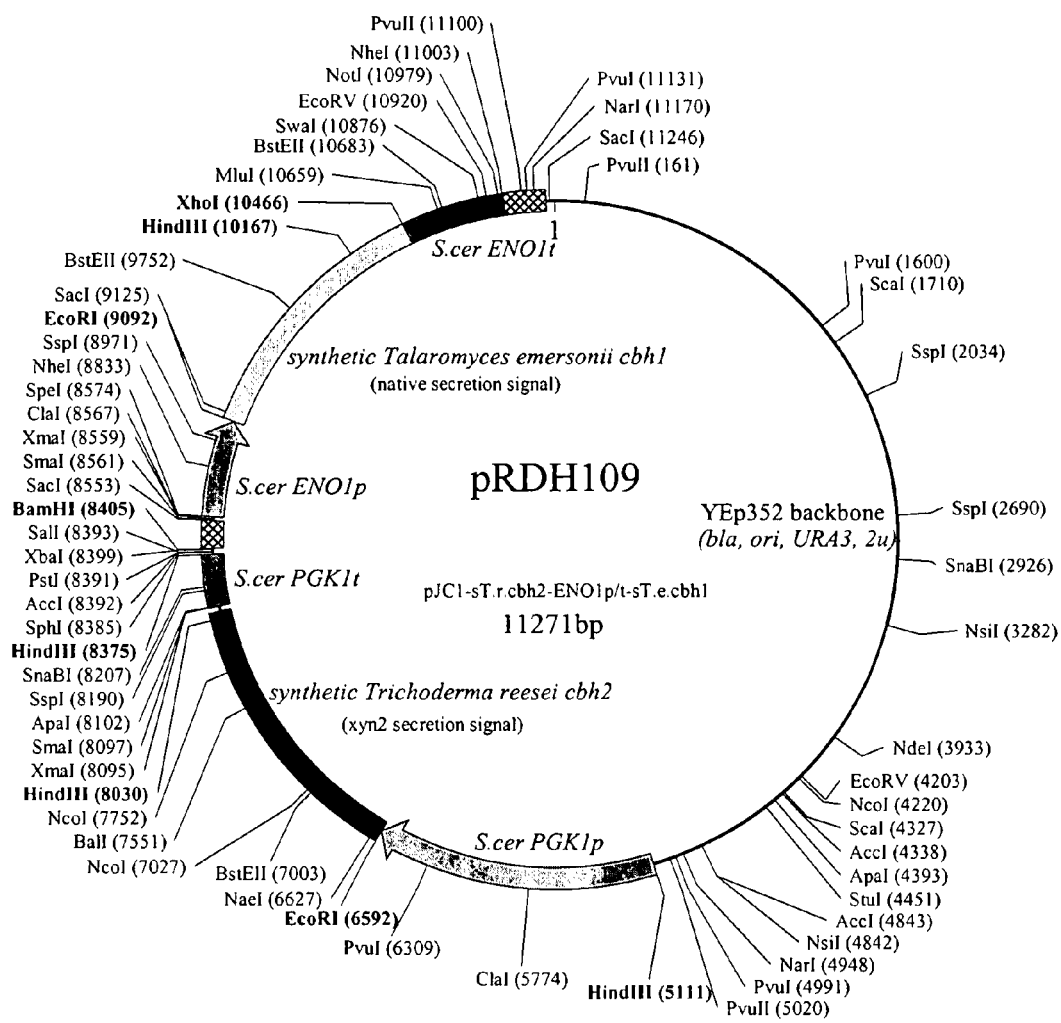

FIG. 8. Plasmid map of pRDH109. The pRDH109 plasmid is the pJC1 vector backbone containing synthetic (codon-optimized) *T. reesei* cbh2 and synthetic (codon-optimized) *T. emersonii* cbh1 in the same orientation to one another.

Figure 9:
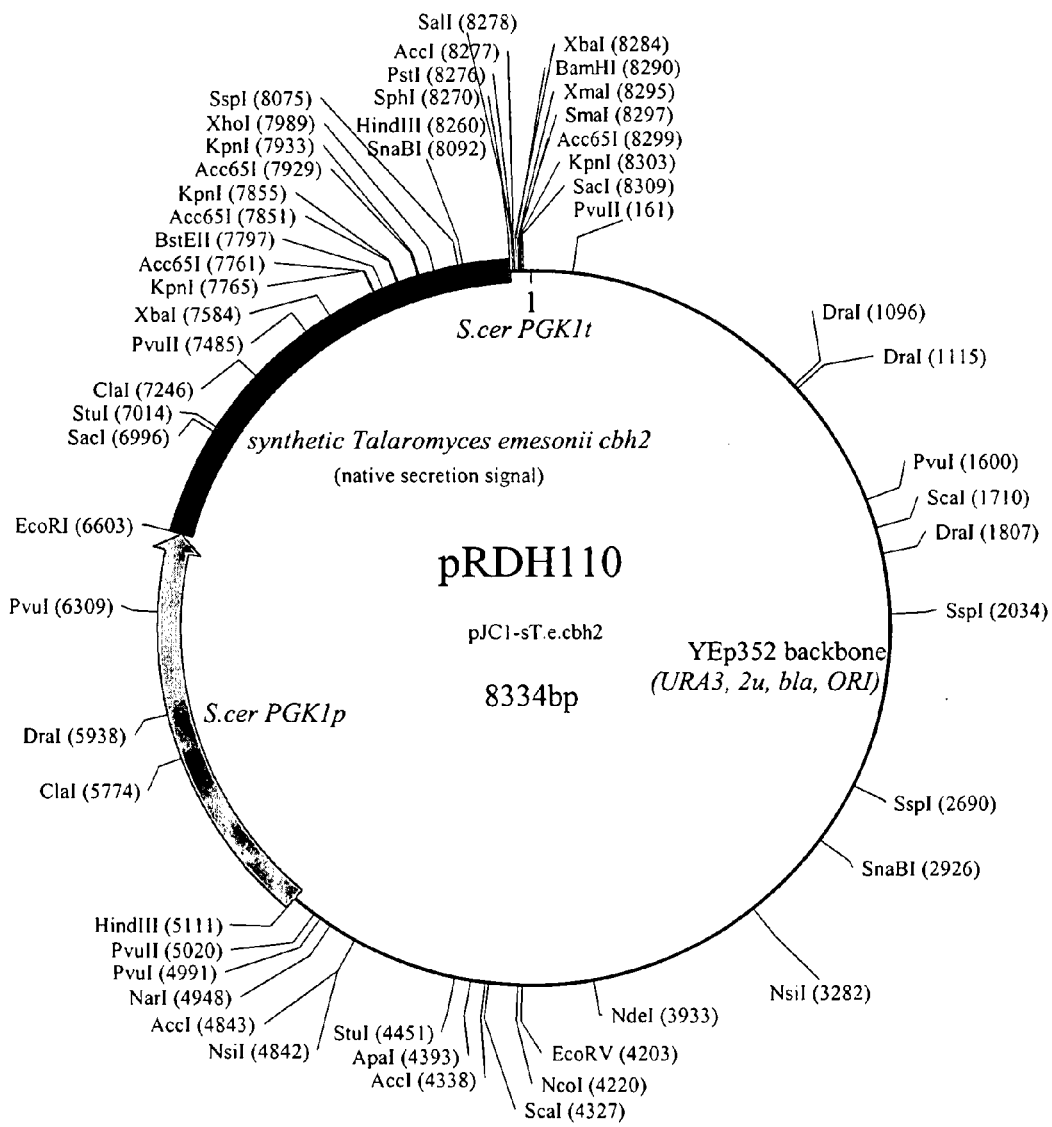

FIG. 9. Plasmid map of pRDH110. The pRDH110 plasmid is the pJC1 vector backbone containing synthetic (codon-optimized) *T. emersonii* cbh2.

Figure 10:
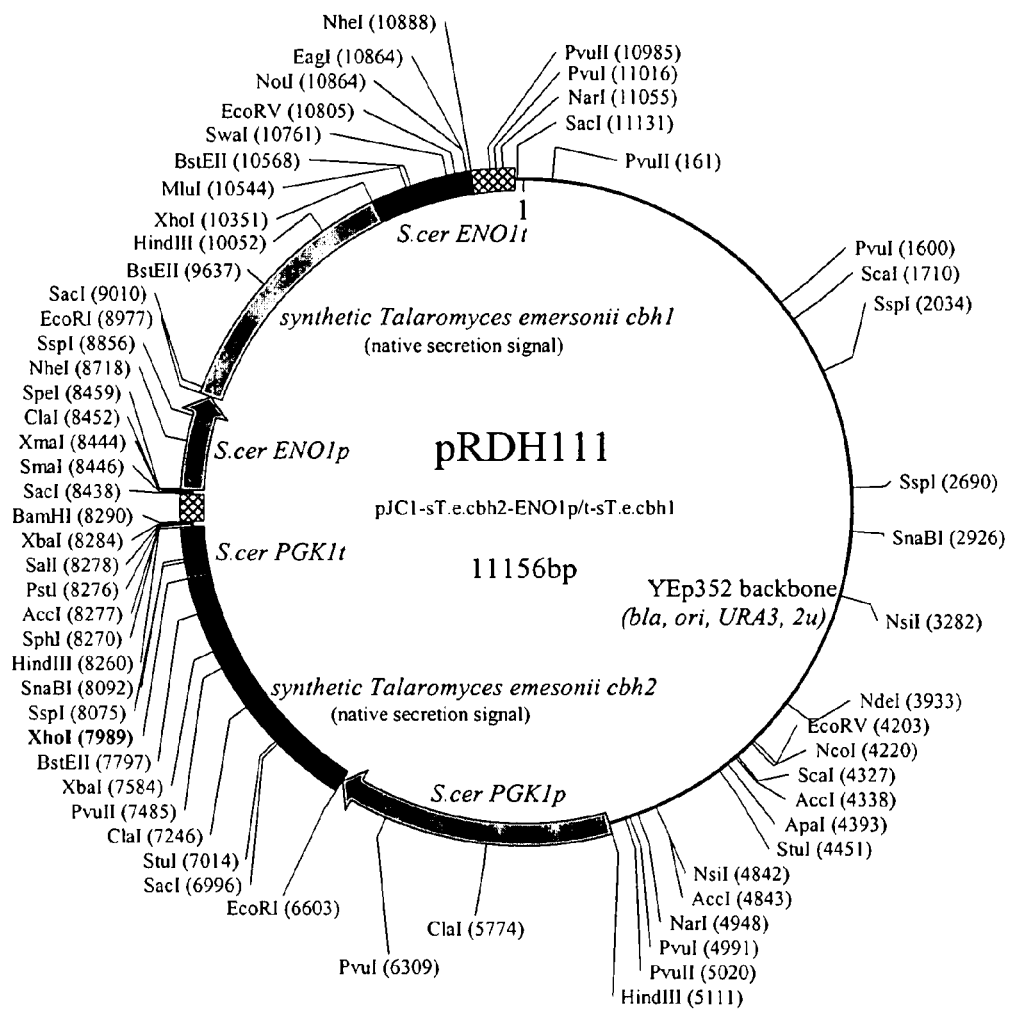

FIG. 10. Plasmid map of pRDH111. The pRDH111 plasmid is the pJC1 vector backbone containing synthetic (codon-optimized) *T. emersonii* cbh2 and synthetic (codon-optimized) *T. emersonii* cbh1 in the same orientation to one another.

Figure 11:
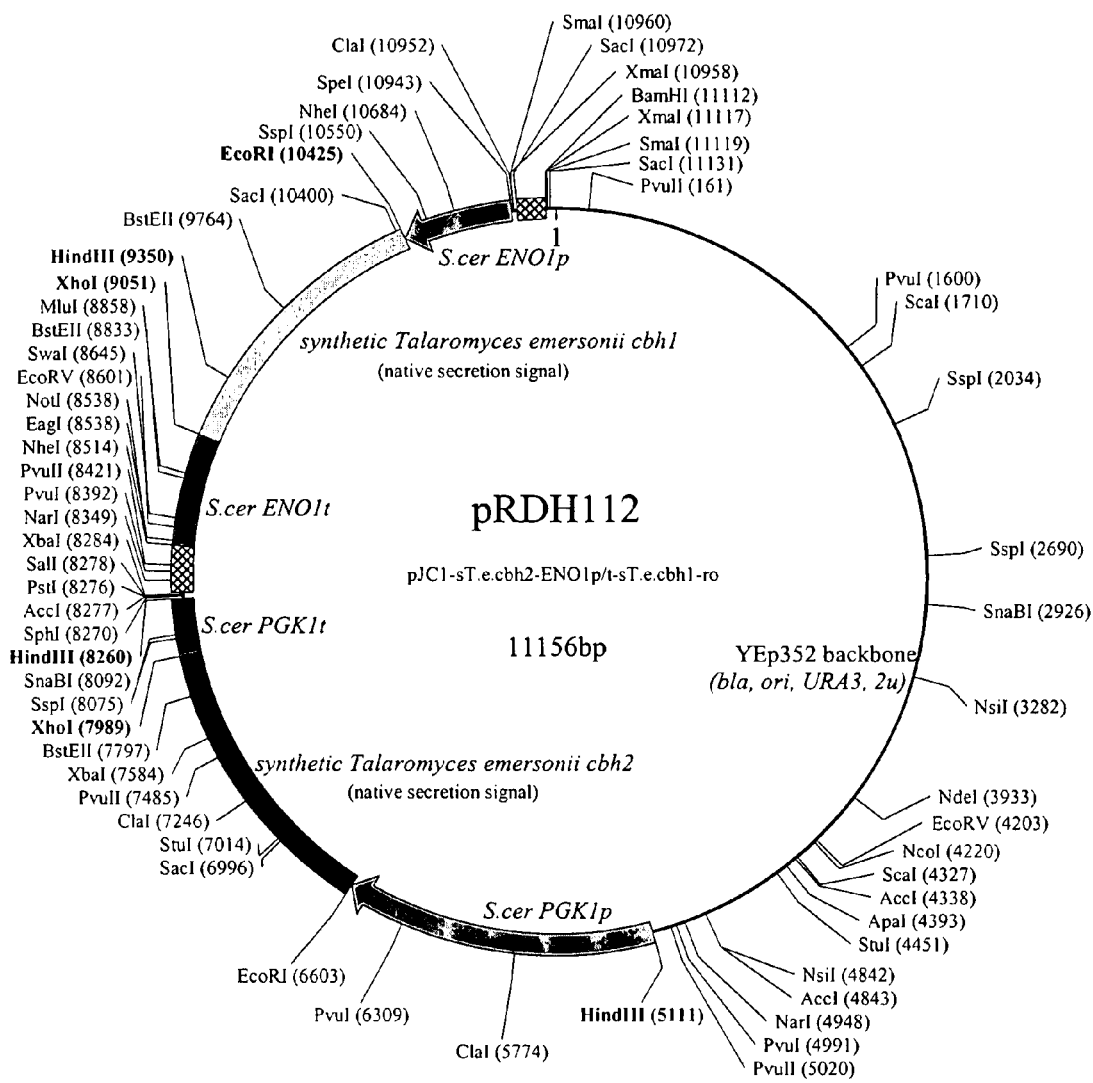

FIG. 11. Plasmid map of pRDH112. The pRDH112 plasmid is the pJC1 vector backbone containing synthetic (codon-optimized) *T. emersonii* cbh2 and synthetic (codon-optimized) *T. emersonii* cbh1 in the reverse orientation to one another.

Figure 12:
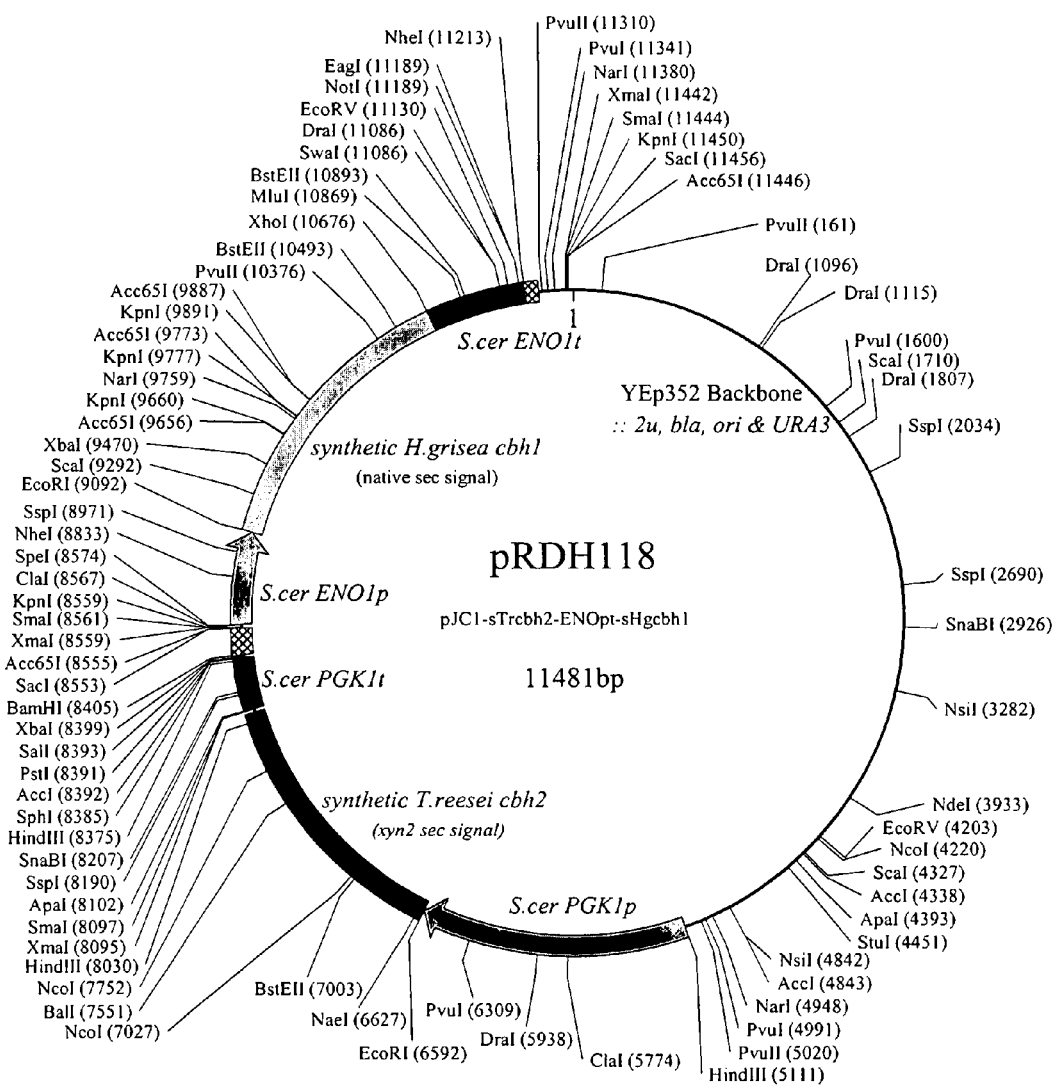

FIG. 12. Plasmid map of pRDH118. The pRDH118 plasmid is the pJC1 vector backbone containing synthetic (codon-optimized) *T. reesei* cbh2 and synthetic (codon-optimized) *H. grisea* cbh1 in the same orientation to one another.

Figure 13:
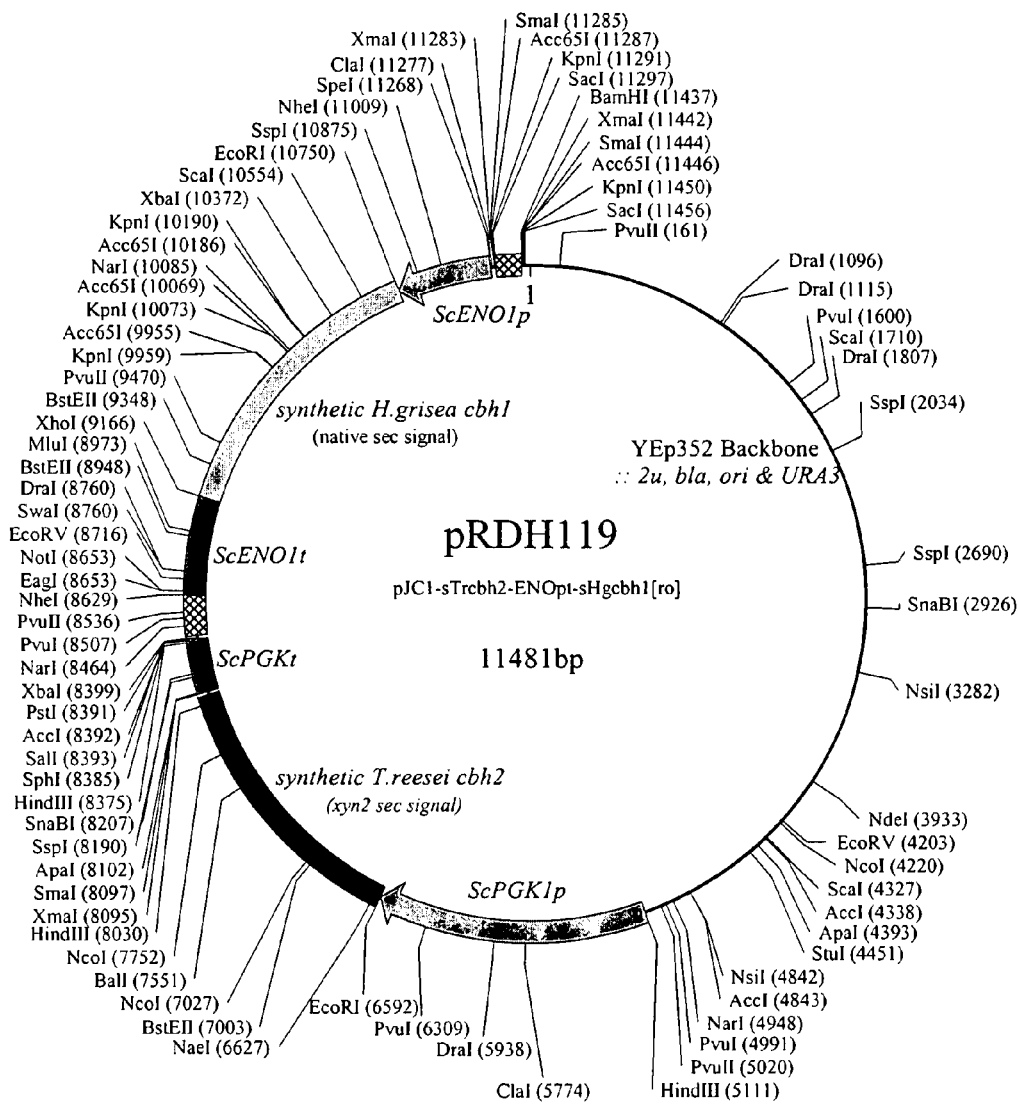

FIG. 13. Plasmid map of pRDH119. The pRDH119 plasmid is the pJC1 vector backbone containing synthetic (codon-optimized) *T. reesei* cbh2 and synthetic (codon-optimized) *H. grisea* cbh1 in the reverse orientation to one another.

Figure 14:
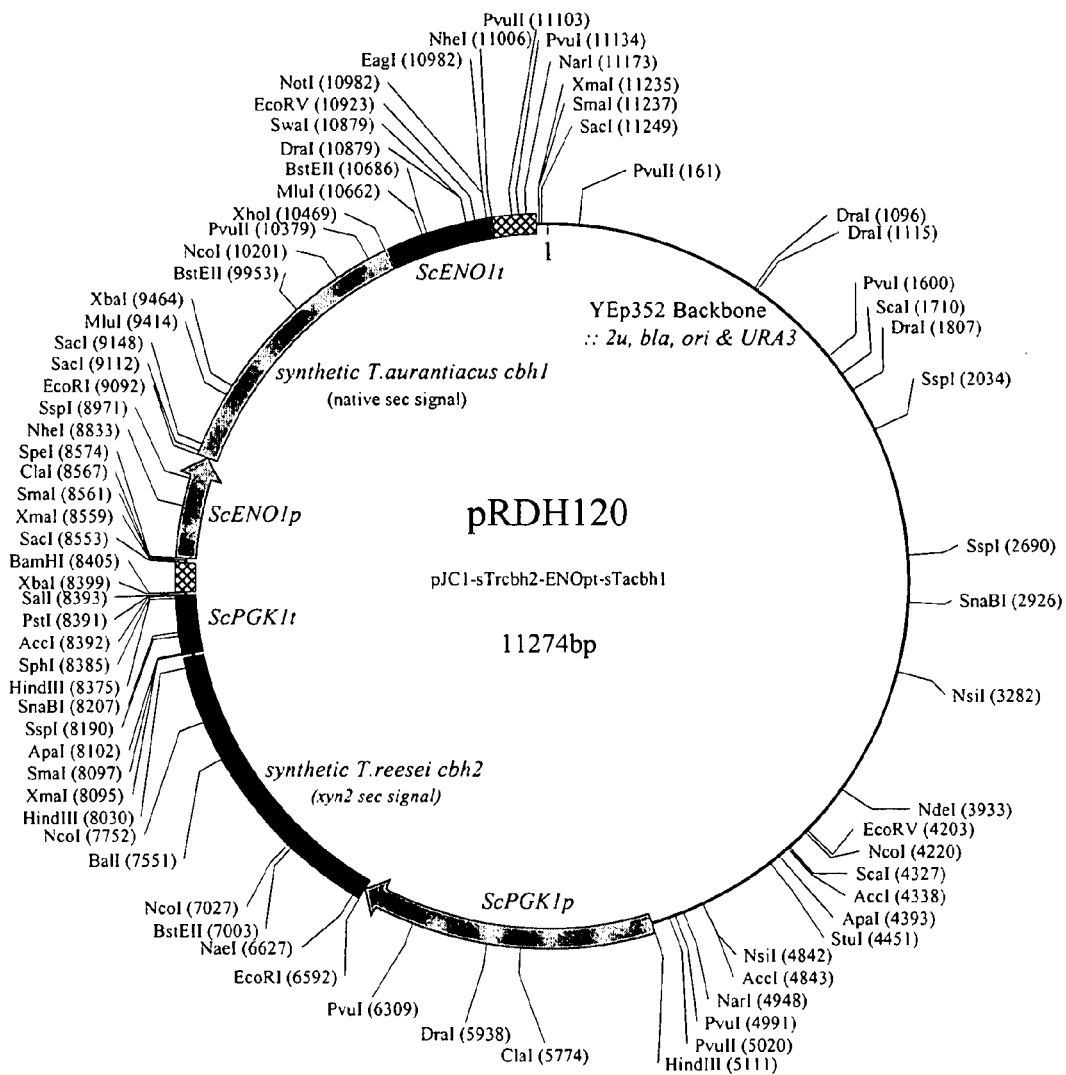

FIG. 14. Plasmid map of pRDH120. The pRDH120 plasmid is the pJC1 vector backbone containing synthetic (codon-optimized) *T. reesei* cbh2 and synthetic (codon-optimized) *T. aurantiacus* cbh1 in the same orientation to one another.

Figure 15:
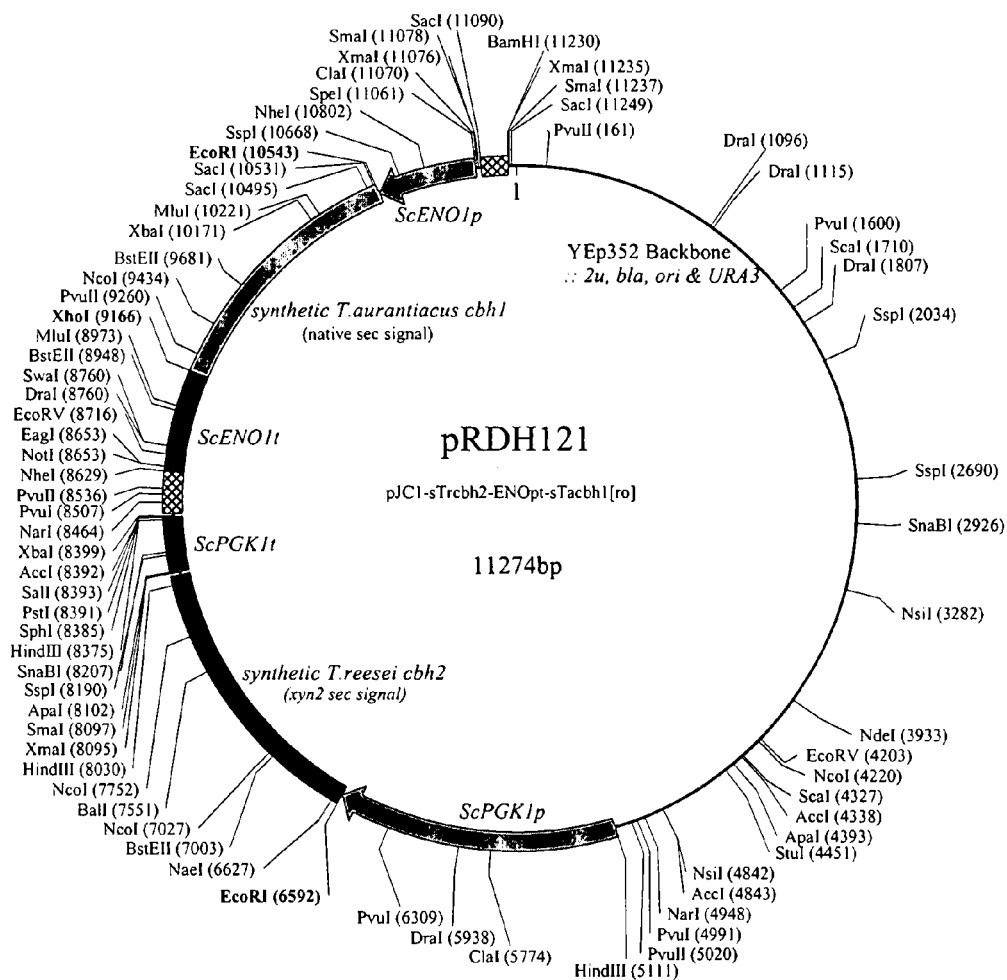

FIG. 15. Plasmid map of pRDH121. The pRDH121 plasmid is the pJC1 vector backbone containing synthetic (codon-optimized) *T. reesei* cbh2 and synthetic (codon-optimized) *T. aurantiacus* cbh1 in the reverse orientation to one another.

Figure 16:
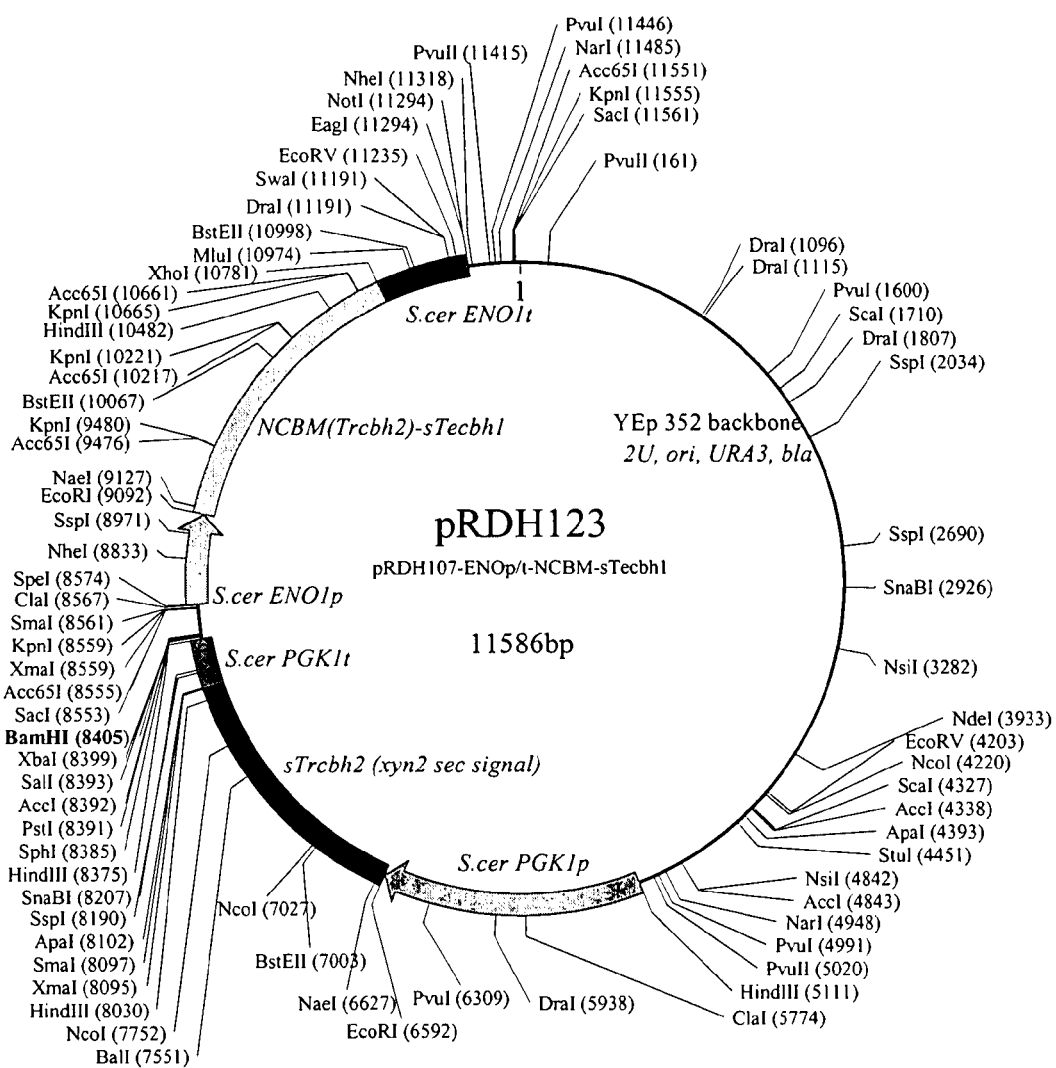

FIG. 16. Plasmid map of pRDH123. The pRDH123 plasmid is the pRDH107 vector backbone containing synthetic (codon-optimized) *T. reesei* cbh2 with a xyn2 secretion signal and a synthetic (codon-optimized) *T. emersonii* cbh2 with a *T. reesei* cbh2 CBM fused at the N-terminal, both of which are in the same orientation to one another.

Figure 17:
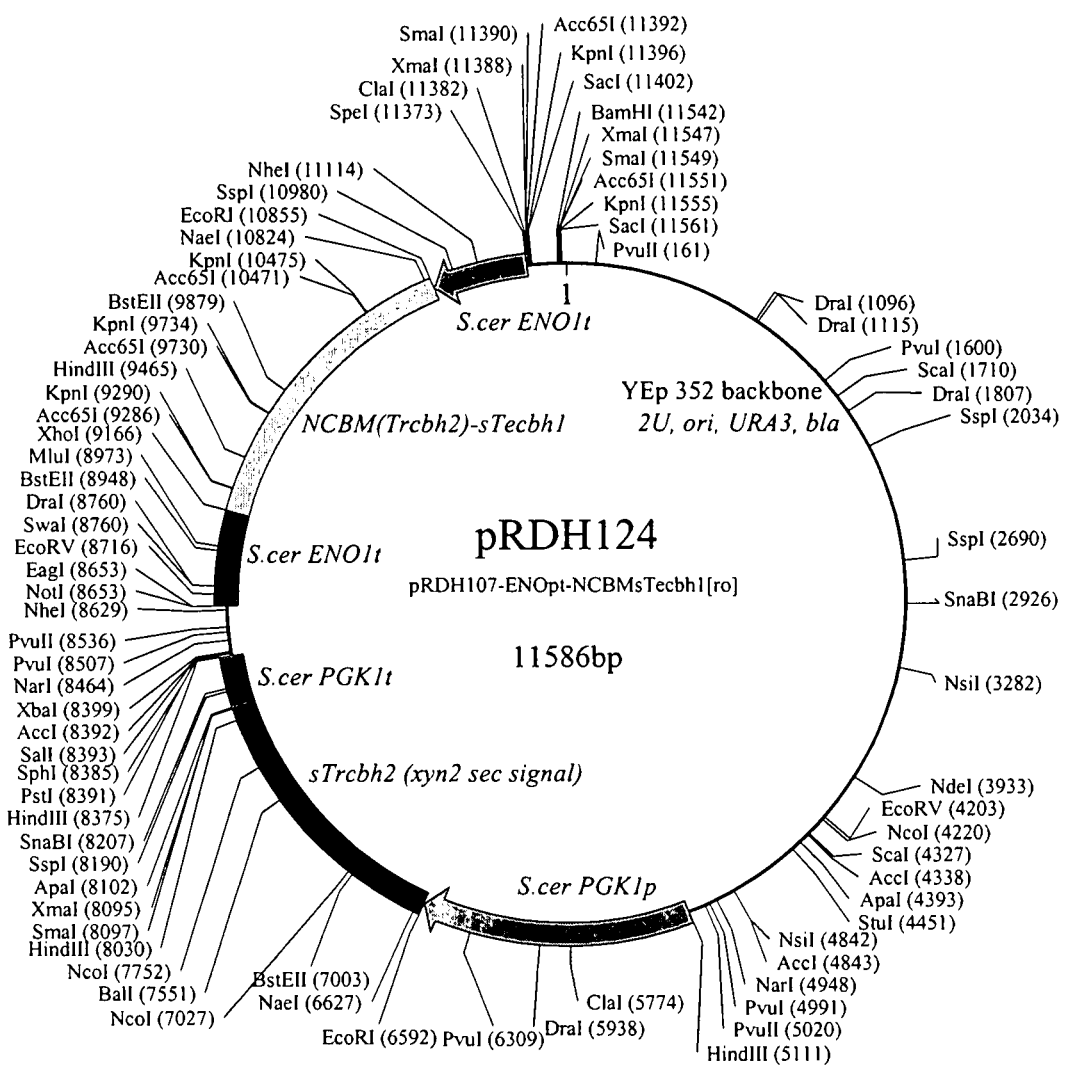

FIG. 17. Plasmid map of pRDH124. The pRDH124 plasmid is the pRDH107 vector backbone containing synthetic (codon-optimized) *T. reesei* cbh2 with a xyn2 secretion signal and a synthetic (codon-optimized) *T. emersonii* cbh2 with a *T. reesei* cbh2 CBM fused at the N-terminal, both of which are in the reverse orientation to one another.

Figure 18:
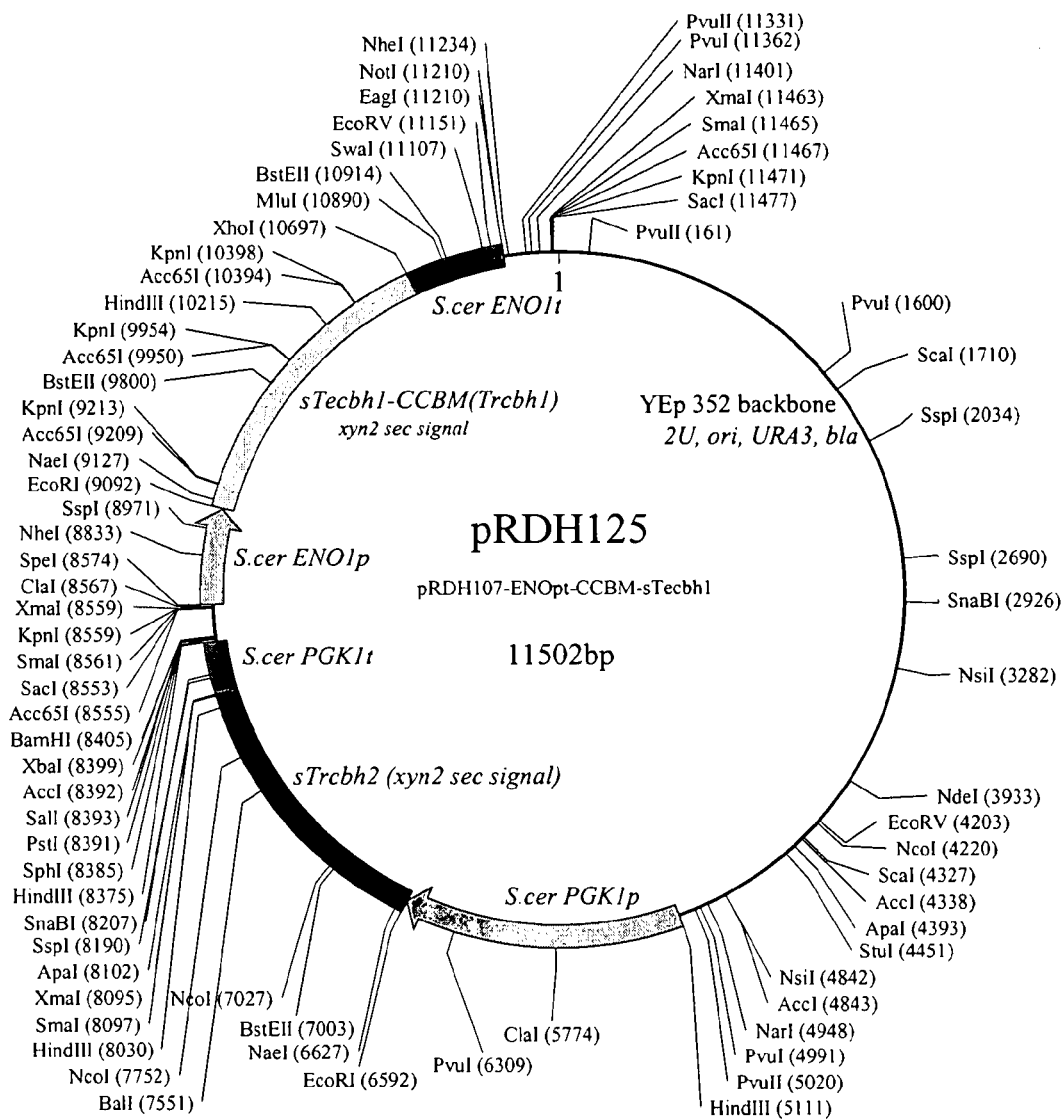

FIG. 18. Plasmid map of pRDH125. The pRDH125 plasmid is the pRDH107 vector backbone containing synthetic (codon-optimized) *T. reesei* cbh2 with a xyn2 secretion signal and a synthetic (codon-optimized) *T. emersonii* cbh2 with a xyn2 secretion signal with a *T. reesei* cbh2 CBM fused at the C-terminal, both of which are in the same orientation to one another.

Figure 19:
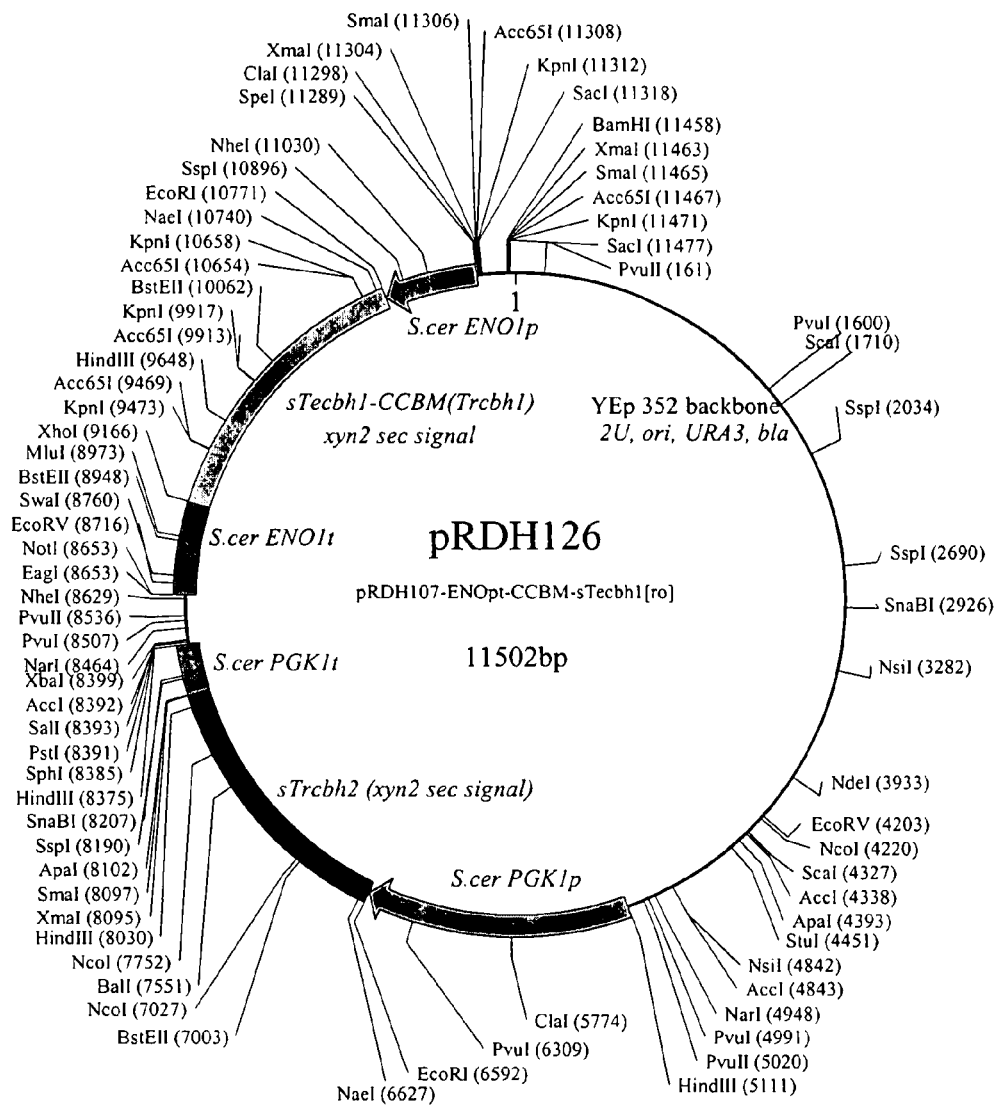

FIG. 19. Plasmid map of pRDH126. The pRDH126 plasmid is the pRDH107 vector backbone containing synthetic (codon-optimized) *T. reesei* cbh2 with a xyn2 secretion signal and a synthetic (codon-optimized) *T. emersonii* cbh2 with a xyn2 secretion signal with a *T. reesei* cbh2 CBM fused at the C-terminal, both of which are in the reverse orientation to one another.

Figure 20:
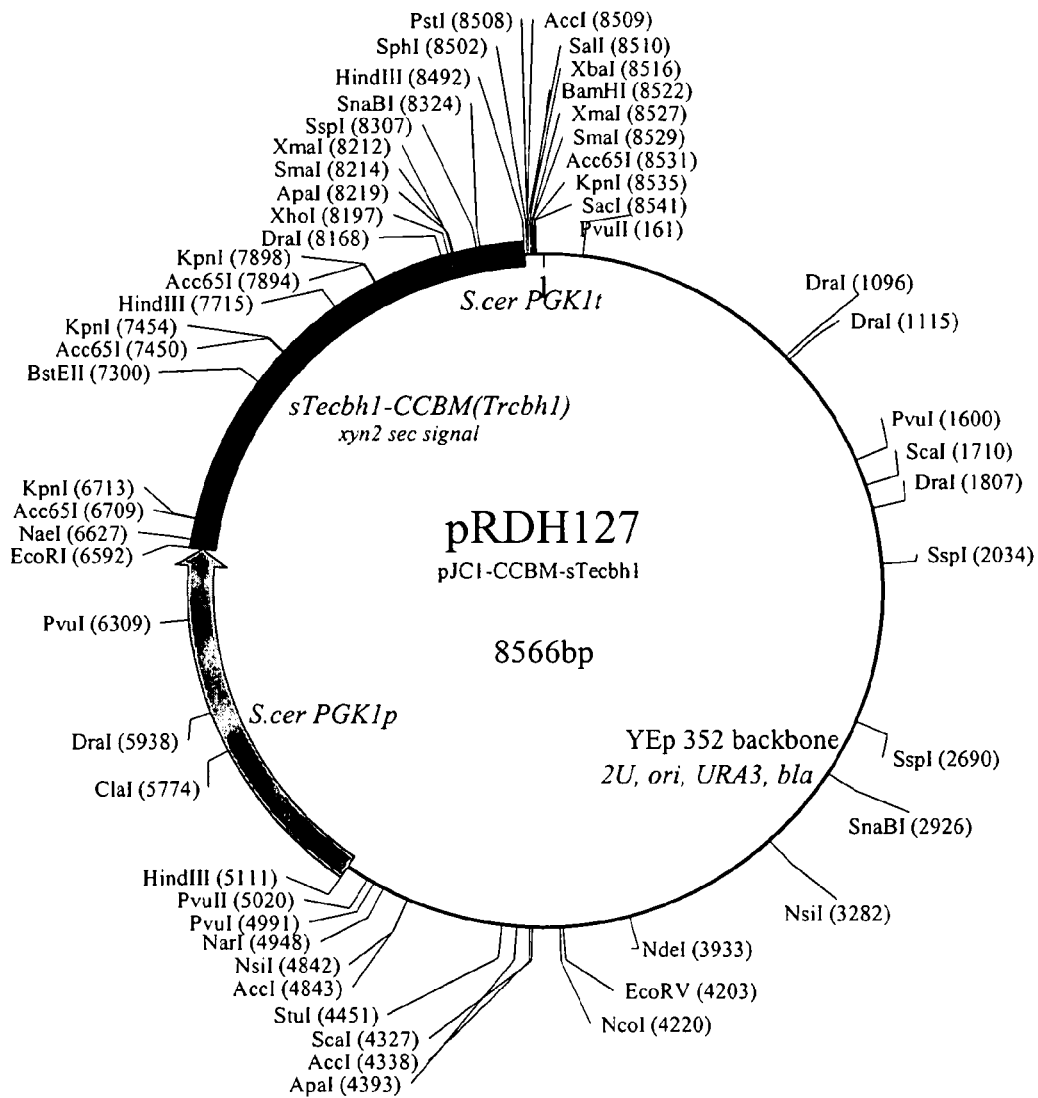

FIG. 20. Plasmid map of pRDH127. The pRDH127 plasmid is the pJC1 vector backbone containing synthetic (codon-optimized) *T. emersonii* cbh1 having a xyn2 secretion signal with a *T. reesei* cbh2 CBM fused at the C-terminal.

Figure 21:
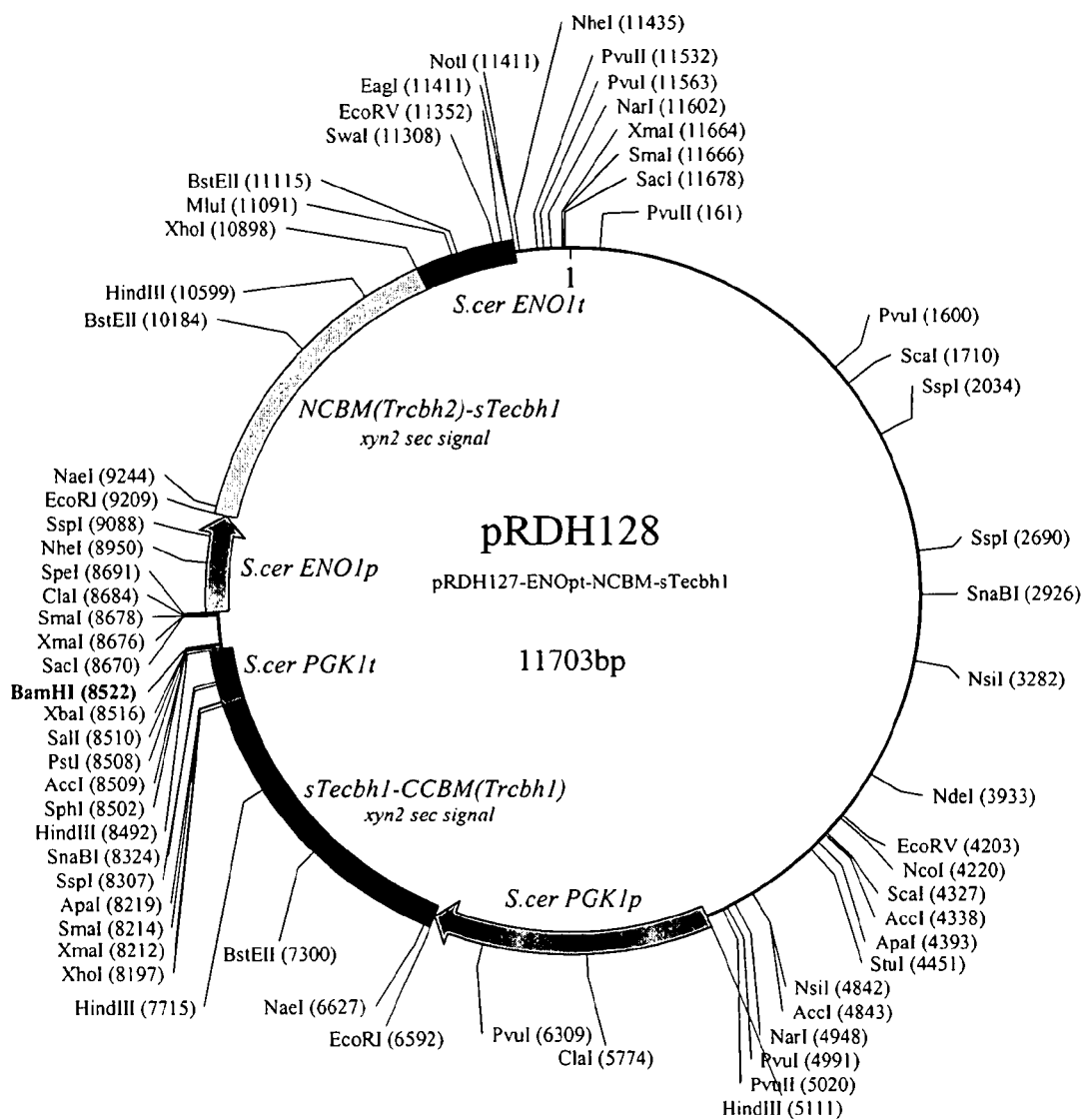

FIG. 21. Plasmid map of pRDH128. The pRDH128 plasmid is the pRDH127 vector backbone containing synthetic (codon-optimized) *T. emersonii* cbh1 having a xyn2 secretion signal with a *T. reesei* cbh2 CBM fused at the N-terminal.

Figure 22:
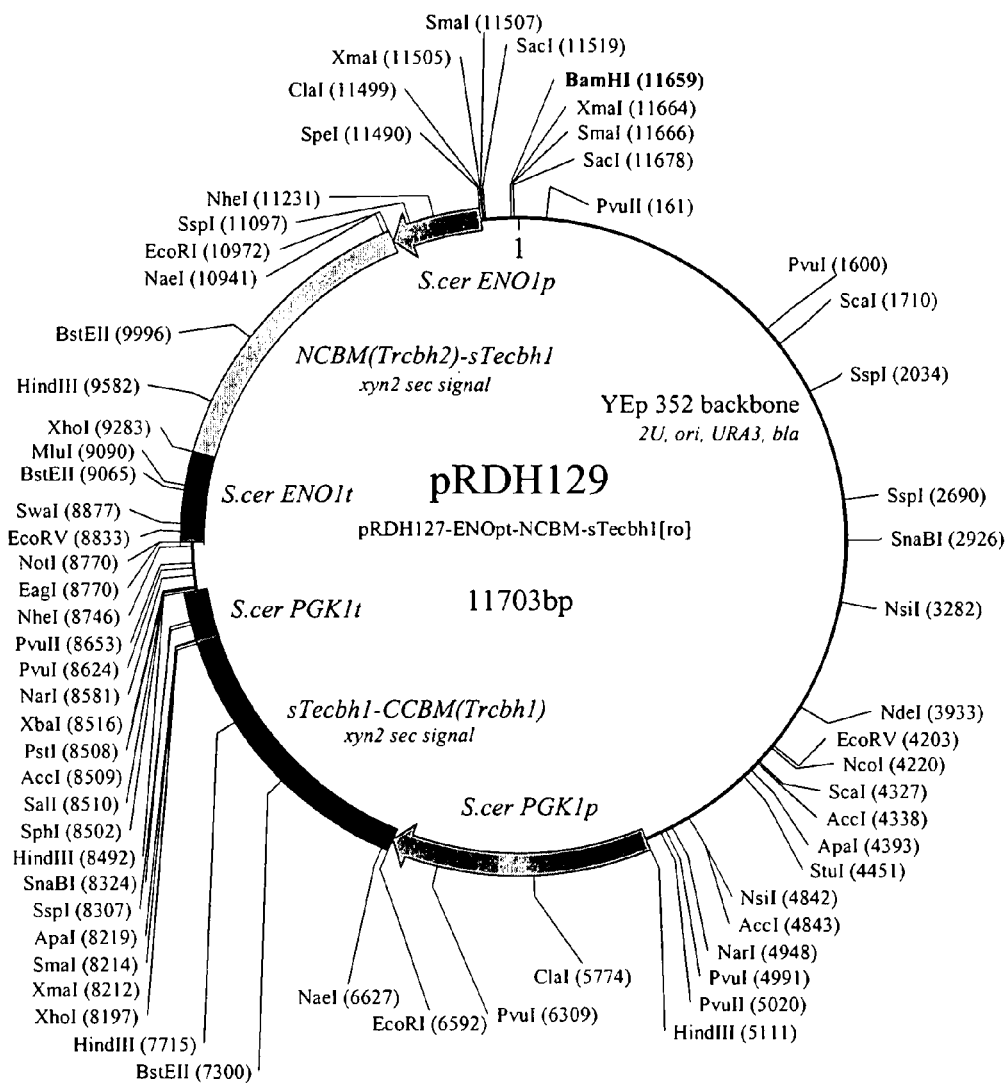

FIG. 22. Plasmid map of pRDH129. The pRDH129 plasmid is the pRDH127 vector backbone containing synthetic (codon-optimized) *T. emersonii* cbh1 having a xyn2 secretion signal with a *T. reesei* cbh2 CBM fused at the N-terminal and a synthetic (codon-optimized) *T. emersonii* cbh1 having a xyn2 secretion signal with a *T. reesei* cbh2 CBM fused at the C-terminal, both of which are in the reverse orientation to one another.

Figure 23:
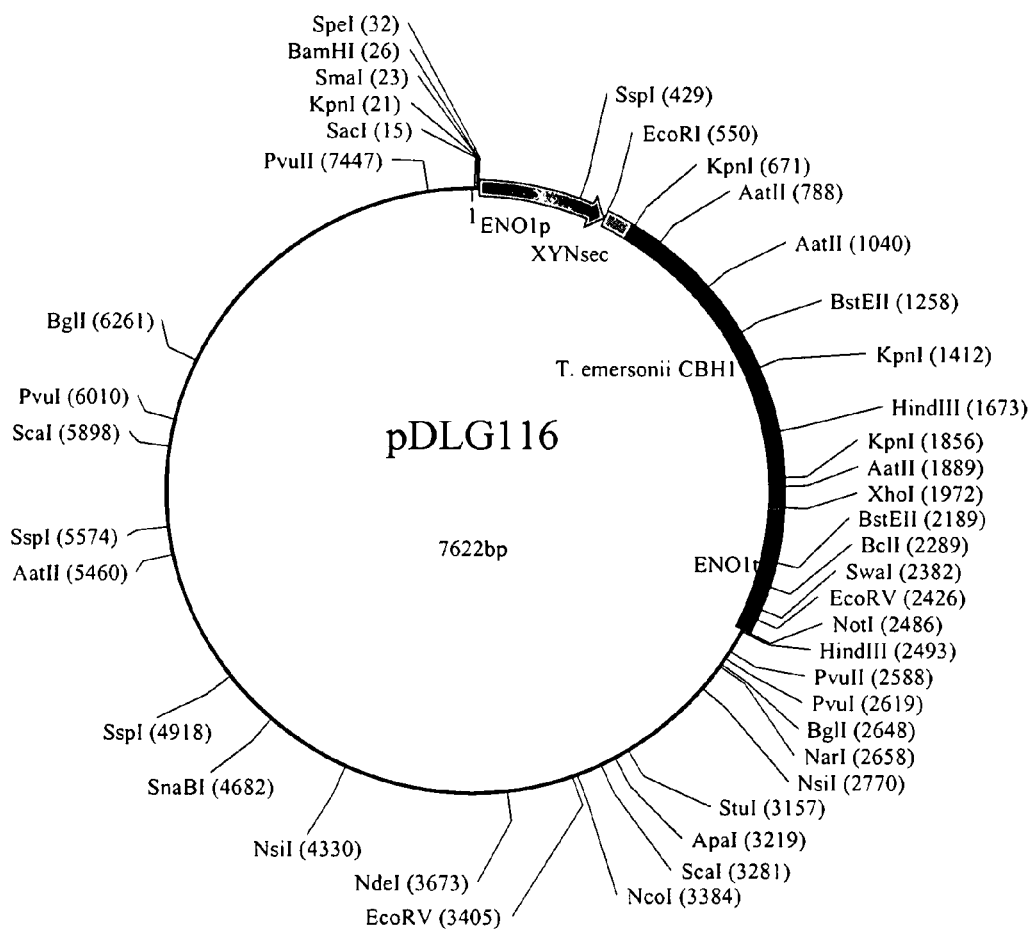

FIG. 23. Plasmid map of pDLG116. The pDLG116 plasmid contains *T. emersonii* cbh1 with the xyn2 secretion signal under the control of the ENO1 promoter and terminator.

Figure 24:
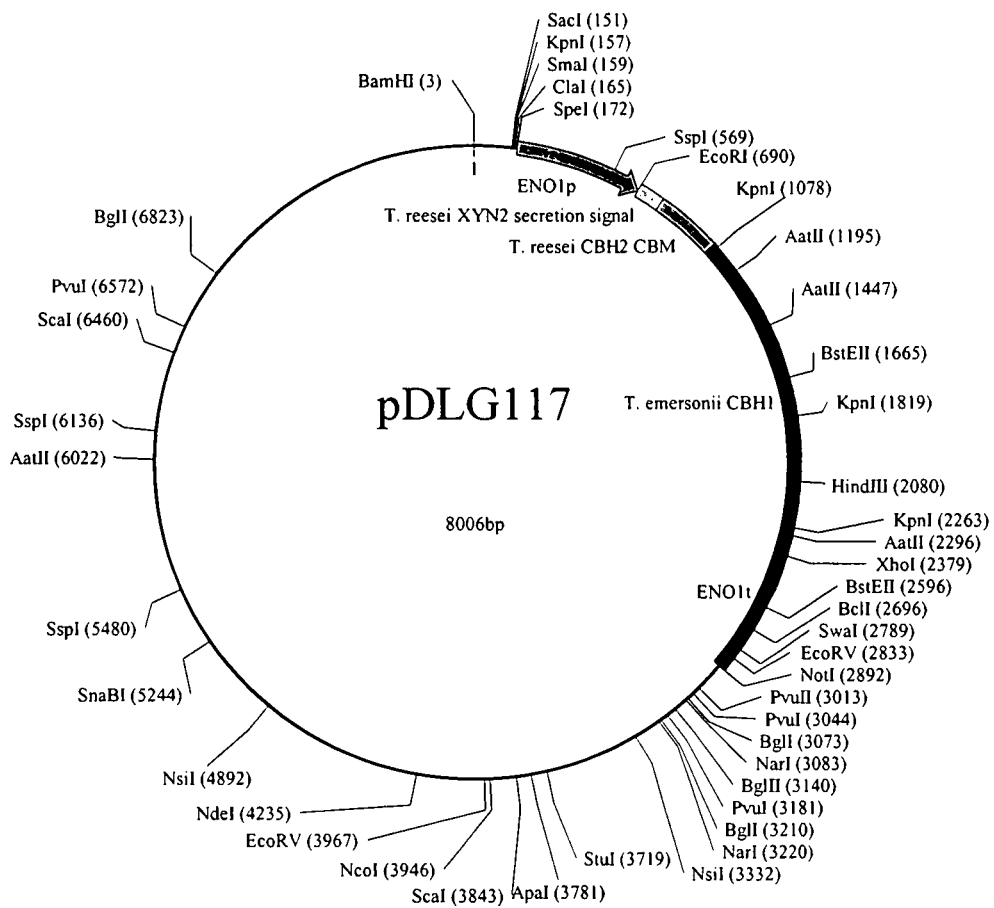

FIG. 24. Plasmid map of pDLG117. The pDLG117 plasmid contains *T. emersonii* cbh1 with the *T. reesei* xyn2 secretion signal and the *T. reesei* cbh2 CBM on the N-terminal side. Cloned as a EcoRI-XhoI into YEPENO1BBH.

Figure 25:
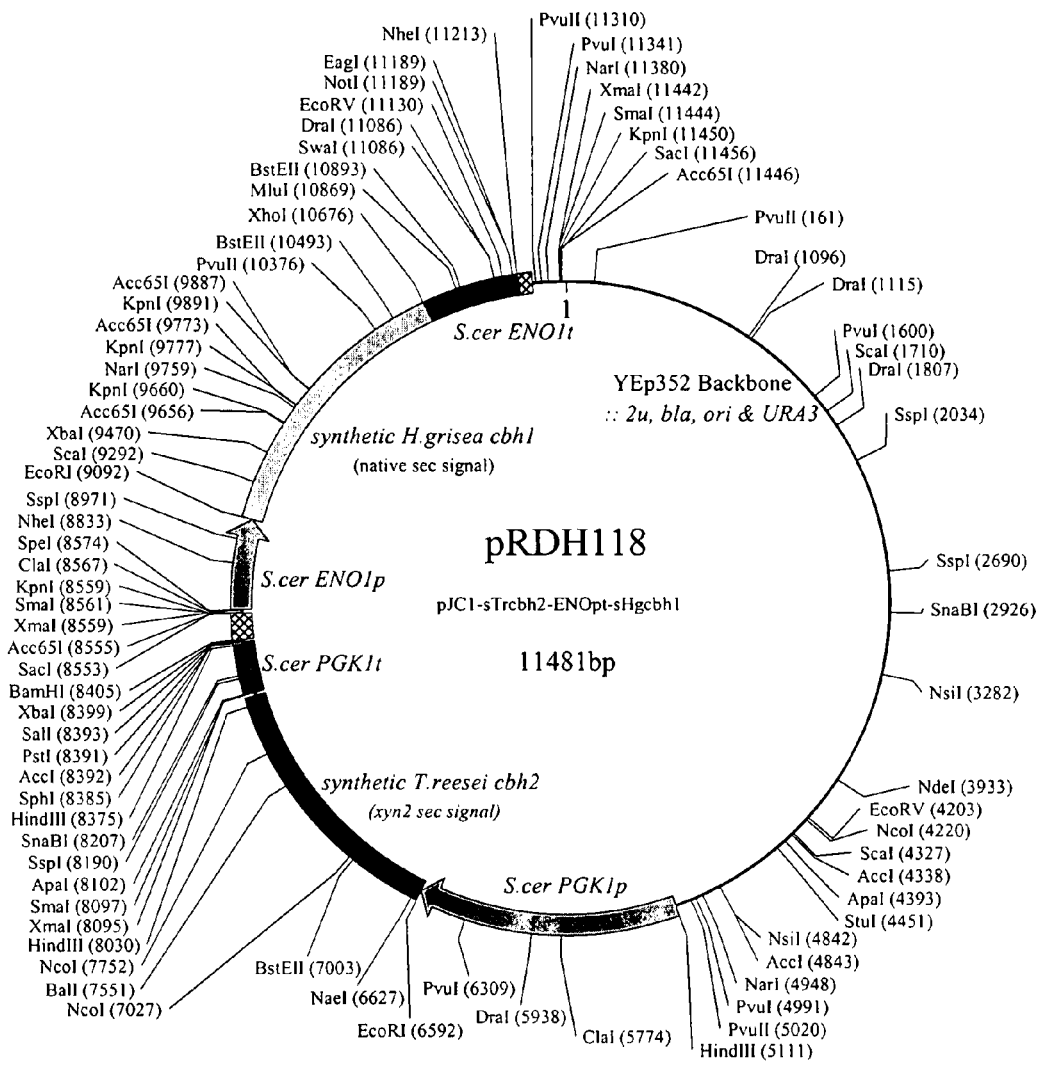

FIG. 25. Plasmid map of pDLG118. The pDLG118 plasmid corresponds to YEpENOBBH containing the *Talaromyces emersonii* cbh1 (XYNSEC and C-terminal CBM).

Figure 26:
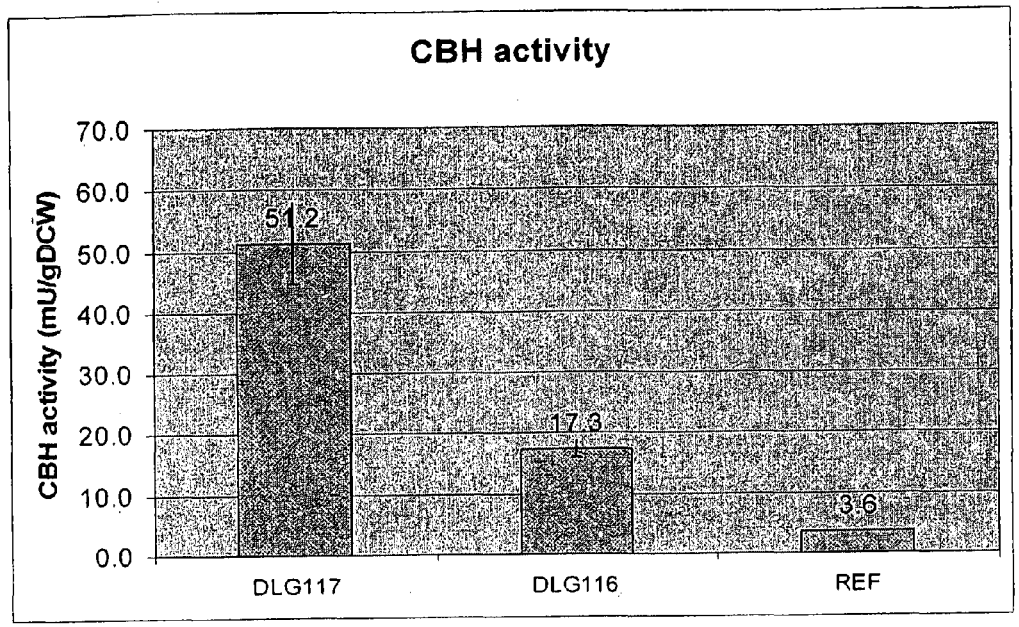

FIG. 26. A bar graph depicting Cbh activity using an adsorption-reaction-sugar detection assay comparing cells transformed with pDLG117, pDLG116 and control.

Figure 27:
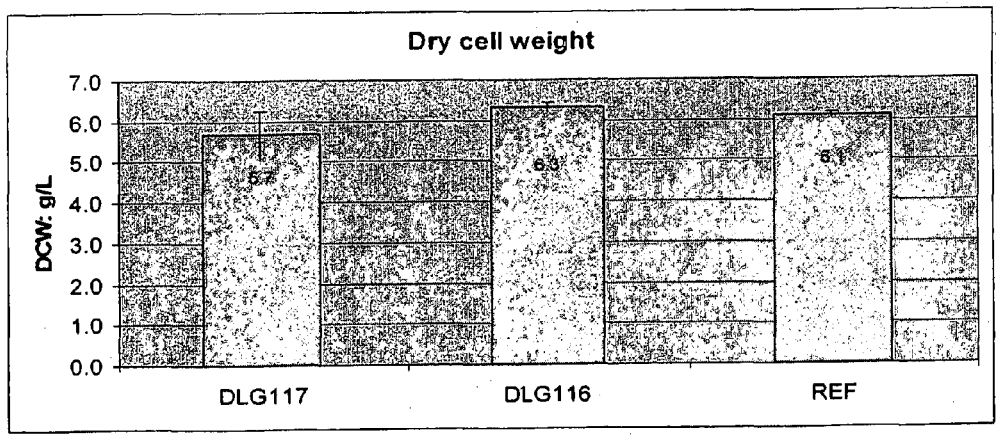

FIG. 27. A bar graph depicting dry cell weight of the cells transformed with pDLG117, pDLG116 and control.

DETAILED DESCRIPTION OF THE INVENTION

The present invention relates to, inter alia, the heterologous expression of the CBH1 gene from *T. emersonii* in host cells, including yeast, e.g., *Saccharomyces cerevisiae*. The present invention provides important tools to enable growth of yeast on cellulosic substrates on ethanol production.

DEFINITIONS

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Preferably, the plasmids or vectors of the present invention are stable and self-replicating.

An "expression vector" is a vector that is capable of directing the expression of genes to which it is operably associated.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

The term "probe" refers to a single-stranded nucleic acid molecule that can base pair with a complementary single stranded target nucleic acid to form a double-stranded molecule.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

As used herein, the term "oligonucleotide" refers to a nucleic acid, generally of about 18 nucleotides, that is hybridizable to a genomic DNA molecule, a cDNA molecule, or an mRNA molecule. Oligonucleotides can be labeled, e.g., with 32P-nucleotides or nucleotides to which a label, such as biotin, has been covalently conjugated. An oligonucleotide can be used as a probe to detect the presence of a nucleic acid according to the invention. Similarly, oligonucleotides (one or both of which may be labeled) can be used as PCR primers, either for cloning full length or a fragment of a nucleic acid of the invention, or to detect the presence of nucleic acids according to the invention. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease SI), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

Polynucleotides of the Invention

The present invention provides for the use of cbh1 and/or cbh2 polynucleotide sequences from *Talaromyces emersonii* (*T. emersonii*), *Humicola grisea* (*H. grisea*), *Thermoascus aurantiacus* (*T. aurantiacus*), and *Trichoderma reesei* (*T. reesei*).

The *T. emersonii* cbh1 nucleic acid sequence is available in GenBank (Accession Number AY081766), and has the following sequence:

(SEQ ID NO: 1)
CTCAGACTCAAACACTCCATCAGCAGCTTCGAAAGCGGTCTTTTTGCT

ATCATCATGCTTCGACGGGCTCTTCTTCTATCCTCTTCCGCCATCCTT

GCTGTCAAGGCACAGCAGGCCGGCACGGCGACGGCAGAGAACCACCCG

CCCCTGACATGGCAGGAATGCACCGCCCCTGGGAGCTGCACCACCCAG

AACGGGGCGGTCGTTCTTGATGCGAACTGGCGTTGGGTGCACGATGTG

AACGGATACACCAACTGCTACACGGGCAATACCTGGGACCCCACGTAC

TGCCCTGACGACGAAACCTGCGCCCAGAACTGTGCGCTGGACGGCGCG

-continued
GATTACGAGGGCACCTACGGCGTGACTTCGTCGGGCAGCTCCTTGAAA

CTCAATTTCGTCACCGGGTCGAACGTCGGATCCCGTCTCTACCTGCTG

CAGGACGACTCGACCTATCAGATCTTCAAGCTTCTGAACCGCGAGTTC

AGCTTTGACGTCGATGTCTCCAATCTTCCGTGCGGATTGAACGGCGCT

CTGTACTTTGTCGCCATGGACGCCGACGGCGGCGTGTCCAAGTACCCG

AACAACAAGGCTGGTGCCAAGTACGGAACCGGGTATTGCGACTCCCAA

TGCCCACGGGACCTCAAGTTCATCGACGGCGAGGCCAACGTCGAGGGC

TGGCAGCCGTCTTCGAACAACGCCAACACCGGAATTGGCGACCACGGC

TCCTGCTGTGCGGAGATGGATGTCTGGGAAGCAAACAGCATCTCCAAT

GCGGTCACTCCGCACCCGTGCGACACGCCAGGCCAGACGATGTGCTCT

GGAGATGACTGCGGTGGCACATACTCTAACGATCGCTACGCGGGAACC

TGCGATCCTGACGGCTGTGACTTCAACCCTTACCGCATGGGCAACACT

TCTTTCTACGGGCCTGGCAAGATCATCGATACCACCAAGCCCTTCACT

GTCGTGACGCAGTTCCTCACTGATGATGGTACGGATACTGGAACTCTC

AGCGAGATCAAGCGCTTCTACATCCAGAACAGCAACGTCATTCCGCAG

CCCAACTCGGACATCAGTGGCGTGACCGGCAACTCGATCACGACGGAG

TTCTGCACTGCTCAGAAGCAGGCCTTTGGCGACACGGACGACTTCTCT

CAGCACGGTGGCCTGGCCAAGATGGGAGCGGCCATGCAGCAGGGTATG

GTCCTGGTGATGAGTTTGTGGGACGACTACGCCGCGCAGATGCTGTGG

TTGGATTCCGACTACCCGACGGATGCGGACCCCACGACCCCTGGTATT

GCCCGTGGAACGTGTCCGACGGACTCGGGCGTCCCATCGGATGTCGAG

TCGCAGAGCCCCAACTCCTACGTGACCTACTCGAACATTAAGTTTGGT

CCGATCAACTCGACCTTCACCGCTTCGTGAGTCTTGGTTACATTTGAA

GTAGACGGAAGTAGCTCTGCGATGGAACTGGCATATGGAGAAGACCAC

ACAAAACTGCATCGAAGAAAAGAGGGGGGAAAAGAGAAAAGCAAAGTT

ATTTAGTTTGAAAATGAAACTACGCTCGTTTTTATTCTTGAAAATCGC

CACTCTTGCCTTTTTTTTCTTTTTCTTTTTATTTTTTTTCCTTTTGA

AATCTTCAATTTAAATGTACATATTGTTAAATCAAATCAAGTAAATAT

ACTTGAAAAAAAAAAAAAAAAAAA

The *H. grisea* cbh1 nucleic acid sequence is available in GenBank (Accession Number X17258), and has the following sequence:

(SEQ ID NO: 2)
GCCGTGACCTTGCGCGCTTTGGGTGGCGGTGGCGAGTCGTGGACGGTG

CTTGCTGGTCGCCGGCCTTCCCGGCGATCCGCGTGATGAGAGGGCCAC

CAACGGCGGGATGATGCTCCATGGGAACTTCCCCATGGAGAAGAGAG

AGAAACTTGCGGAGCCGTGATCTGGGGAAAGATGCTCCGTGTCTCGTC

TATATAACTCGAGTCTCCCCGAGCCCTCAACACCACCAGCTCTGATCT

CACCATCCCCATCGACAATCACGCAAACACAGCAGTTGTCGGGCCATT

CCTTCAGACACATCAGTCACCCTCCTTCAAAATGCGTACCGCCAAGTT

CGCCACCCTCGCCGCCCTTGTGGCCTCGGCCGCCGCCCAGCAGGCGTG

-continued

```
CAGTCTCACCACCGAGAGGCACCCTTCCCTCTCTTGGAACAAGTGCAC
CGCCGGCGGCCAGTGCCAGACCGTCCAGGCTTCCATCACTCTCGACTC
CAACTGGCGCTGGACTCACCAGGTGTCTGGCTCCACCAACTGCTACAC
GGGCAACAAGTGGGATACTAGCATCTGCACTGATGCCAAGTCGTGCGC
TCAGAACTGCTGCGTCGATGGTGCCGACTACACCAGCACCTATGGCAT
CACCACCAACGGTGATTCCCTGAGCCTCAAGTTCGTCACCAAGGGCCA
GCACTCGACCAACGTCGGCTCGCGTACCTACCTGATGGACGGCGAGGA
CAAGTATCAGAGTACGTTCTATCTTCAGCCTTCTCGCGCCTTGAATCC
TGGCTAACGTTTACACTTCACAGCCTTCGAGCTCCTCGGCAACGAGTT
CACCCTTCGATGTCGATGTCTCCAACATCGGCTGCGGTCTCAACGGCGC
CCTGTACTTCGTCTCCATGGACGCCGATGGTGGTCTCAGCCGCTATCC
TGGCAACAAGGCTGGTGCCAAGTACGGTACCGGCTACTGCGATGCTCA
GTGCCCCCGTGACATCAAGTTCATCAACGGCGAGGCCAACATTGAGGG
CTGGACCGGCTCCACCAACGACCCCAACGCCGGCGCGGGCCGCTATGG
TACCTGCTGCTCTGAGATGGATATCTGGGAAGCCAACAACATGGCTAC
TGCCTTCACTCCTCACCCTTGCACCATCATTGGCCAGAGCCGCTGCGA
GGGCGACTCGTGCGGTGGCACCTACAGCAACGAGCGCTACGCCGGCGT
CTGCGACCCCGATGGCTGCGACTTCAACTCGTACCGCCAGGGCAACAA
GACCTTCTACGGCAAGGGCATGACCGTCGACACCACCAAGAAGATCAC
TGTCGTCACCCAGTTCCTCAAGGATGCCAACGGCGATCTCGGCGAGAT
CAAGCGCTTCTACGTCCAGGATGGCAAGATCATCCCCAACTCCGAGTC
CACCATCCCCGGCGTCGAGGGCAATTCCATCACCCAGGACTGGTGCGA
CCGCCAGAAGGTTGCCTTTGGCGACATTGACGACTTCAACCGCAAGGG
CGGCATGAAGCAGATGGGCAAGGCCCTCGCCGGCCCCATGGTCCTGGT
CATGTCCATCTGGGATGACCACGCCTCCAACATGCTCTGGCTCGACTC
GACCTTCCCTGTCGATGCCGCTGGCAAGCCCGGCGCCGAGCGCGGTGC
CTGCCCGACCACCTCGGGTGTCCCTGCTGAGGTTGAGGCCGAGGCCCC
CAACAGCAACGTCGTCTTCTCCAACATCCGCTTCGGCCCCATCGGCTC
GACCGTTGCTGGTCTCCCCGGCGCGGGCAACGGCGGCAACAACGGCGG
CAACCCCCCGCCCCCACCACCACCACCTCCTCGGCTCCGGCCACCAC
CACCACCGCCAGCGCTGGCCCCAAGGCTGGCCGCTGGCAGCAGTGCGG
CGGCATCGGCTTCACTGGCCCGACCCAGTGCGAGGAGCCCTACATTTG
CACCAAGCTCAACGACTGGTACTCTCAGTGCCTGTAAATTCTGAGTCG
CTGACTCGACGATCACGGCCGGTTTTTGCATGAAAGGAAACAAACGAC
CGCGATAAAAATGGAGGGTAATGAGATGTC
```

The *T. aurantiacus* cbh1 nucleic acid sequence is available in GenBank (Accession Number AF478686), and has the following sequence:

(SEQ ID NO: 3)
```
GAATTCTAGACCTTTATCCTTTCATCCGACCAGACTTCCCTTTTTGAC
CTTGGCGCCCTGTTGACTACCTACCTACCTAGGTAGTAACGTCGTCGA
CCCTCTTGAATGATCCTTGTCACACTGCAAACATCCGAAAACATACGG
CAAAAGATGATTGGGCATGGATGCAGGAGACATCGAATGAGGGCTTAG
AAGGAAATGAAAACCTGGGACCAGGACGCTAGGTACGATGAAATCCGC
CAATGGTGAAACTTTAAGTCGTGCCTACAGCACAGGCTCTGTGAAGAT
TGCGCTGTTCAGACTTAATCTTCTCATCACAGTCCAAGTCTTTATGAA
AAGGAAAAAGAGAGGGAAGAGCGCTATTTCGAGCTGTTGGCCTCATAG
GGAGACAGTCGAGCATACCAGCGGTATCGACGTTAGACTCAACCAAGA
ATAATGACGAGAATAAACACAGAAGTCAACCTTGAACTGGATAGCAGG
GTTCCAGCAGCAGATAGTTACTTGCATAAAGACAACTCCCCGAGGGCT
CTCTGCATACACCAGGATGTTCCGGAATTATTCACTGCTCGTTTCCGA
CGTGGCGTCAGTGATCCGTCTCCACAGAACTCTACCTGGGAATAACCC
AGGGGAGGAATCTGCAAGTAAGAACTTAATACCAATCCCCGGGGCTGC
CGAGGTGAATCGAATCTCCCGCGGGAAATTAAACCCATACGATGTTTT
TGCACCACATGCATGCTTAGCACGATTTCTCCGCAAGGGAGTCACAGA
GAAAGACATATTTCGCATACTACTGTGACTCTGCAGAGTTACATATCA
CTCAGGATACATTGCAGATCATTGTCCGGGCATCAAAAATGGACCTGC
AGGATCAACGGCCCGACAAAACACAAGTGGCTAAAGCTGGGGGATGCC
CGAAACCCTCTGGTGCAATATCATTTGATGGATGTTCCCCCCGCATTT
CTAAGCATCGACGGATCGGCCCGCATACTAATCCTTTTATCAACCAA
AAGTTCCACTCGACTAGAGAAAAAAAGGCCAAGGCCACTAGTTGCAG
TCGGATACTGGTCTTTTCGCCGTCCAACACCTTCATCCATGATCCCCT
TAGCCACCAATGCCCCACATAATACATGTTGACATAGGTACGTAGCTC
TGTTATCCAATCGGATCCGAACCTCTTTAACGGACCCCTCCTACACAC
CTTATCCTAACTTCAGAAGACTGTTGCCCATTGGGGATTGAGGAGGTC
CGGGTCGCAGGATGCGTTCTAGGCTAAATTCTCGGCCGGTAGCCATCT
CGAATCTCTCGTGAAGCCTTCATCTGAACGGTTGGCGGCCCGTCAAGC
CGATGACCATGGGTTCCTGATAGAGCTTGTGCCTGACCGGCCTTGGCG
GCATAGACGAGCTGAACACATCAGGTATGAACAGATCAGATATAAAGT
CGGATTGAGTCCTAGTACGAAGCAATCCGCCACCACCAAATCAAGCAA
CGAGCGACACGAATAACAATATCAATCGAATCGCAATGTATCAGCGCG
CTCTTCTCTTCTCTTTCTTCCTCGCCGCCGCCCGCGCGCACGAGGCCG
GTACCGTAACCGCAGAGAATCACCCTTCCCTGACCTGGCAGCAATGCT
CCAGCGGCGGTAGTTGTACCACGCAGAATGGAAAAGTCGTTATCGATG
CGAACTGGCGTTGGGTCCATACCACCTCTGGATACACCAACTGCTACA
CGGGCAATACGTGGGACACCAGTATCTGTCCCGACGACGTGACCTGCG
CTCAGAATTGTGCCTTGGATGGAGCGGATTACAGTGGCACCTATGGTG
TTACGACCAGTGGCAACGCCCTGAGACTGAACTTTGTCACCCAAAGCT
CAGGGAAGAACATTGGCTCGCGCCTGTACCTGCTGCAGGACGACACCA
CTTATCAGATCTTCAAGCTGCTGGGTCAGGAGTTTACCTTCGATGTCG
ACGTCTCCAATCTCCCTTGCGGGCTGAACGGCGCCCTCTACTTTGTGG
CCATGGACGCCGACGGCAATTTGTCCAAATACCCTGGCAACAAGGCAG
```

GCGCTAAGTATGGCACTGGTTACTGCGACTCTCAGTGCCCTCGGGATC
TCAAGTTCATCAACGGTCAGGTACGTCAGAAGTGATAACTAGCCAGCA
GAGCCCATGAATCATTAACTAACGCTGTCAAATACAGGCCAACGTTGA
AGGCTGGCAGCCGTCTGCCAACGACCCAAATGCCGGCGTTGGTAACCA
CGGTTCCTCGTGCGCTGAGATGGATGTCTGGGAAGCCAACAGCATCTC
TACTGCGGTGACGCCTCACCCATGCGACACCCCCGGCCAGACCATGTG
CCAGGGAGACGACTGTGGTGGAACCTACTCCTCCACTCGATATGCTGG
TACCTGCGACCCTGATGGCTGCGACTTCAATCCTTACCAGCCAGGCAA
CCACTCGTTCTACGGCCCCGGGAAGATCGTCGACACTAGCTCCAAATT
CACCGTCGTCACCCAGTTCATCACCGACGACGGGACACCCTCCGGCAC
CCTGACGGAGATCAAACGCTTCTACGTCCAGAACGGCAAGGTGATCCC
CCAGTCGGAGTCGACGATCAGCGGCGTCACCGGCAACTCAATCACCAC
CGAGTATTGCACGGCCCAGAAGGCAGCCTTCGGCGACAACACCGGCTT
CTTCACGCACGGCGGGCTTCAGAAGATCAGTCAGGCTCTGGCTCAGGG
CATGGTCCTCGTCATGAGCCTGTGGGACGATCACGCCGCCAACATGCT
CTGGCTGGACAGCACCTACCCGACTGATGCGACCCGGACACCCCTGG
CGTCGCGCGCGGTACCTGCCCCACGACCTCCGGCGTCCCGGCCGACGT
TGAGTCGCAGAACCCCAATTCATATGTTATCTACTCCAACATCAAGGT
CGGACCCATCAACTCGACCTTCACCGCCAACTAAGTAAGTAACGGGCA
CTCTACCACCGAGAGCTTCGTGAAGATACAGGGGTAGTTGGGAGATTG
TCGTGTACAGGGGACATGCGATGCTCAAAAATCTACATCAGTTTGCCA
ATTGAACCATGAAGAAAAGGGGGAGATCAAAGAAGTCTGTCAGAAGAG
AGGGGCTGTGGCAGCTTAAGCCTTGTTGTAGATCGTTCAGAGAAAAAA
AAAGTTTGCGTACTTATTATATTAGGTCGATCATTATCCGATTGACTC
CGTGACAAGAATTAAAAAGAGTACTGCTTGCTTGCCTATTTAAATTGT
TATATACGCCGTAGCGCTTGCGGACCACCCCTCACAGTATATCGGTTC
GCCTCTTCTTGTCTCTTCATCTCACATCACAGGTCCAGGTCCAGCCCG
GCCCGGTCCGGGTGCCATGCATGCACAGGGGGACTAATATATTAATCG
TGACCCTGTVCCTAAGCTAGGGTCCCTGCATTTTGAACCTGTGGACGT
CTG

The *T. reesei* cbh1 nucleic acid sequence is available in GenBank (Accession Number E00389), and has the following sequence:

(SEQ ID NO: 4)
AAGGTTAGCCAAGAACAATAGCCGATAAAGATAGCCTCATTAAACGGA
ATGAGCTAGTAGGCAAAGTCAGCGAATGTGTATATATAAAGGTTCGAG
GTCCGTGCCTCCCTCATGCTCTCCCCATCTACTCATCAACTCAGATCC
TCCAGGAGACTTGTACACCATCTTTTGAGGCACAGAAACCCAATAGTC
AACCGCGGACTGGCATCATGTATCGGAAGTTGGCCGTCATCACGGCCT
TCTTGGCCACAGCTCGTGCTCAGTCGGCCTGCACTCTCCAATCGGAGA
CTCACCCGCCTCTGACATGGCAGAAATGCTCGTCTGGTGGCACTTGCA
CTCAACAGACAGGCTCCGTGGTCATCGACGCCAACTGGCGCTGGACTC
ACGCTACGAACAGCAGCACGAACTGCTACGATGGCAACACTTGGAGCT
CGACCCTATGTCCTGACAACGAGACCTGCGCGAAGAACTGCTGTCTGG
ACGGTGCCGCCTACGCGTCCACGTACGGAGTTACCACGAGCGGTAACA
GCCTCTCCATTGGCTTTGTCACCCAGTCTGCGCAGAAGAACGTTGGCG
CTCGCCTTTACCTTATGGCGAGCGACACGACCTACCAGGAATTCACCC
TGCTTGGCAACGAGTTCTCTTTCGATGTTGATGTTTCGCAGCTGCCGT
AAGTGACTTACCATGAACCCCTGACGTATCTTCTTGTGGGCTCCCAGC
TGACTGGCCAATTTAAGGTGCGGCTTGAACGGAGCTCTCTACTTCGTG
TCCATGGACGCGGATGGTGGCGTGAGCAAGTATCCCACCAACAACGCT
GGCGCCAAGTACGGCACGGGGTACTGTGACAGCCAGTGTCCCCGCGAT
CTGAAGTTCATCAATGGCCAGGCCAACGTTGAGGGCTGGGAGCCGTCA
TCCAACAACGCAAACACGGGCATTGGAGGACACGGAAGCTGCTGCTCT
GAGATGGATATCTGGGAGGCCAACTCCATCTCCGAGGCTCTTACCCCC
CACCCTTGCACGACTGTCGGCCAGGAGATCTGCGAGGGTGATGGGTGC
GGCGGAACTTACTCCGATAACAGATATGGCGGCACTTGCGATCCCGAT
GGCTGCGACTGGAACCCATACCGCCTGGGCAACACCAGCTTCTACGGC
CCTGGCTCAAGCTTTACCCTCGATACCACCAAGAAATTGACCGTTGTC
ACCCAGTTCGAGACGTCGGGTGCCATCAACCGATACTATGTCCAGAAT
GGCGTCACTTTCCAGCAGCCCAACGCCGAGCTTGGTAGTTACTCTGGC
AACGAGCTCAACGATGATTACTGCACAGCTGAGGAGACAGAATTCGGC
GGATCTCTTTCTCAGACAAGGGCGGCCTGACTCAGTTCAAGAAGGCTA
CCTCTGGCGGCATGGTTCTGGTCATGAGTCTGTGGGATGATGTGAGTT
TGATGGACAAACATGCGCGTTGACAAAGAGTCAAGCAGCTGACTGAGA
TGTTACAGTACTACGCCAACATGCTGTGGCTGGACTCCACCTACCCGA
CAAACGAGACCTCCTCCACACCCGGTGCCGTGCGCGGAAGCTGCTCCA
CCAGCTCCGGTGTCCCTGCTCAGGTCGAATCTCAGTCTCCCAACGCCA
AGGTCACCTTCTCCAACATCAAGTTCGGACCCATTGGCAGCACCGGCA
ACCCTAGCGGCGGCAACCCTCCCGGCGGAAACCGTGGCACCACCACCA
CCCGCCGCCCAGCCACTACCACTGGAAGCTCTCCCGGACCTACCCAGT
CTCACTACGGCCAGTGCGGCGGTATTGGCTACAGCGGCCCCACGGTCT
GCGCCAGCGGCACAACTTGCCAGGTCCTGAACCCTTACTACTCTCAGT
GCCTGTAAAGCTCCGTGCGAAAGCCTGACGCACCGGTAGATTCTTGGT
GAGCCCGTATCATGACGGCGGCGGGAGCTACATGGCCCCGGGTGATTT
ATTTTTTTTGTATCTACTTCTGACCCTTTTCAAATATACGGTCAACTC
ATCTTTCACTGGAGATGCGGCCTGCTTGGTATTGCGATGTTGTCAGCT
TGGCAAATTGTGGCTTTCGAAAACACAAAACGATTCCTTAGTAGCCAT
GCATTTTAAGATAACGGAATAGAAGAAAGAGGAAATTAAAAAAAAAAA
AAAAACAAACATCCCGTTCATAACCCGTAGAATCGCCGCTCTTCGTGT
ATCCCAGTACCA

The *T. emersonii* cbh2 nucleic acid sequence is available in GenBank (Accession Number AF439936), and has the following sequence:

(SEQ ID NO: 5)
GACGGACCTGCACTTAGTCGGTAGGTTATGTATGTAGCTGGAGATTGG
GATAGGGAAGTTAGCTAATAGTCTACTTCGTGTGAGGGTTGATTTTGA
TGGTCGACAGTATTCGTTTCTTATACGCAGCGTCATGGATCTGTGTTT
CTGTCACATGTCGGGTGGATGGTTCCTGGACAGCAGCACACAAATGGT
GTTCTGTAGATAGGCGATACTCGGCAGGGGATTGTGCAGGGGATTGTA
TCGTAGATGGTTCTAGTAAAATAGATCCCGAGTATGGTTAGCTCTCAT
ACCTCGAGTNGATGAAGCACAATATGCTACGATATGCCAAGTAAAACT
CTATTGTATTCTGCAGCTAGCAATTGAAGAATCCGACATTCCCATTGT
CATCTAATCGGGCAGACATGTGCAAAGAGGGACGATTCGTGATCGAAG
TGCTCCAATCCATGGCGTAGGACCAGACAGCTCCATCCGATCTAGAGC
TATATGGAGCTCCTCGCAACTCCGACACTCCGCGAGACAGCTCTCACA
AGCACTATAAATATGGCCAAGAACCCTGCAGAACAGCTTCACTCTACA
GCCCGTTGAGCAGAACAAACAAAATATCACTCCAGAGAGAAAGCAACA
TGCGGAATCTTCTTGCTCTTGCACCGGCCGCGCTGCTTGTCGGCGCAG
CGGAAGCGCAACAATCCCTCTGGGGACAATGTGAGCAGCTCCTAAACG
TCTGTCTGAGGGATTATGTCTGACTGCTCAGGCGGCGGGAGTTCGTGG
ACTGGCGCGACGAGCTGTGCTGCTGGAGCGACGTGCAGCACAATCAAT
CCTTGTACGTCTGCTGAACGATAATCCTACATTGTTGACGTGCTAACT
GCGTAGACTACGCACAATGCGTTCCTGCAACGGCCACTCCGACCACGC
TGACGACAACGACAAAACCAACGTCCACCGGCGGCGCTGCTCCAACGA
CTCCTCCTCCGACAACGACTGGAACAACGACATCGCCCGTCGTCACCA
GGCCCGCGTCTGCCTCCGGCAACCCGTTCGAAGGCTACCAGCTCTACG
CCAATCCGTACTATGCGTCGGAGGTGATTAGTTTGGCAATTCCCTCGC
TGAGCAGCGAGCTGGTTCCCAAGGCGAGCGAGGTGGCCAAGGTGCCGT
CTTTCGTCTGGCTGTAAGTAAATTCCCCCAGGCTGTCATTTCCCCTTA
CTGATCTTGTCCAGCGACCAAGCCGCCAAGGTGCCCAGCATGGGCGAC
TATCTGAAAGACATCCAGTCGCAGAACGCAGCCGGCGCAGACCCCCCG
ATTGCAGGCATCTTTGTCGTCTACGACCTGCCTGACCGCGACTGCGCG
GCTGCAGCCAGCAATGGCGAGTTCTCCATCGCCAACAACGGCGTCGCC
CTGTACAAGCAGTACATCGACTCGATCCGCGAGCAGCTGACGACCTAT
TCAGATGTGCACACCATCCTGGTCATCGGTAGTTCCAGTCCTCTTCTG
TGATGTTGATGAAAAAAATACTGACTGACTCCTGCAGAACCCGACAGC
CTTGCGAACGTGGTCACCAACCTGAACGTGCCGAAATGCGCAAATGCC
CAGGACGCCTATCTCGAATGCATCAACTACGCCATCACCCAGCTCGAT
CTGCCAAACGTGGCCATGTATCTTGATGCTGGTGAGTCCTCACATACA
AGTGAATAAAAATAAAACTGATGCAGTGCAGGACACGCCGGATGGCTA
GGCTGGCAAGCCAACCTCGCCCCCGCCGCCCAGCTGTTTGCCTCGGTG
TACAAAAACGCCTCCTCTCCGGCATCCGTCCGCGGTCTCGCCACCAAC

GTCGCCAACTACAACGCCTGGTCGATCAGCCGGTGCCCGTCGTACACG
CAGGGCGACGCCAATTGCGACGAGGAGGATTACGTGAATGCCTTGGGG
CCGTTGTTCCAGGAACAGGGATTCCCGGCATATTTTATCATTGATACA
TGTAAGCTTTACCCCAGAACCCCTCCATAGAAGGTCAATCTAACGGTA
ATGTACAGCCCGCAATGGCGTCCGACCCACCAAGCAAAGCCAATGGGG
CGACTGGTGCAACGTCATCGGCACGGGCTTCGGCGTCCGGCCCACGAC
CGACACCGGCAATCCTCTCGAGGACGCTTTCGTCTGGGTCAAGCCCGG
TGGCGAGAGCGATGGCACGTCCAACACGACCTCTCCGCGGTACGACTA
CCACTGCGGGCTGAGCGATGCGCTGCAGCCGGCGCCGGAGGCGGGGAC
TTGGTTCCAGGTATGACGCGCCTTCGTATTAGCAATTACGATACATGT
GCATGCTGACCATGCGACAGGCGTACTTTGAGCAGTTGCTCACGAATG
CTAACCCGCTGTTCTGA

The *T. reesei* cbh2 nucleic acid sequence is available in GenBank (Accession Number M16190), and has the following sequence:

(SEQ ID NO: 6)
TCGAACTGACAAGTTGTTATATTGCCTGTGTACCAAGCGCGAATGTGG
ACAGGATTAATGCCAGAGTTCATTAGCCTCAAGTAGAGCCTATTTCCT
CGCCGGAAAGTCATCTCTCTTATTGCATTTCTGCCCTTCCCACTAACT
CAGGGTGCAGCGCAACACTACACGCAACATATACACTTTATTAGCCGT
GCAACAAGGCTATTCTACGAAAAATGCTACACTCCACATGTTAAAGGC
GCATTCAACCAGCTTCTTTATTGGGTAATATACAGCCAGGCGGGGATG
AAGCTCATTAGCCGCCACTCAAGGCTATACAATGTTGCCAACTCTCCG
GGCTTTATCCTGTGCTCCCGAATACCACATCGTGATGATGCTTCAGCG
CACGGAAGTCACAGACACCGCCTGTATAAAAGGGGGACTGTGACCCTG
TATGAGGCGCAACATGGTCTCACAGCAGCTCACCTGAAGAGGCTTGTA
AGATCACCCTCTGTGTATTGCACCATGATTGTCGGCATTCTCACCACG
CTGGCTACGCTGGCCACACTCGCAGCTAGTGTGCCTCTAGAGGAGCGG
CAAGCTTGCTCAAGCGTCTGGTAATTATGTGAACCCTCTCAAGAGACC
CAAATACTGAGATATGTCAAGGGGCCAATGTGGTGGCCAGAATTGGTC
GGGTCCGACTTGCTGTGCTTCCGGAAGCACATGCGTCTACTCCAACGA
CTATTACTCCCAGTGTCTTCCCGGCGCTGCAAGCTCAAGCTCGTCCAC
GCGCGCCGCGTCGACGACTTCTCGAGTATCCCCCACAACATCCCGGTC
GAGCTCCGCGACGCCTCCACCTGGTTCTACTACTACCAGAGTACCTCC
AGTCGGATCGGGAACCGCTACGTATTCAGGCAACCCTTTTGTTGGGGT
CACTCCTTGGGCCAATGCATATTACGCCTCTGAAGTTAGCAGCCTCGC
TATTCCTAGCTTGACTGGAGCCATGGCCACTGCTGCAGCAGCTGTCGC
AAAGGTTCCCTCTTTTATGTGGCTGTAGGTCCTCCCGGAACCAAGGCA
ATCTGTTACTGAAGGCTCATCATTCACTGCAGAGATACTCTTGACAAG
ACCCCTCTCATGGAGCAAACCTTGGCCGACATCCGCACCGCCAACAAG
AATGGCGGTAACTATGCCGGACAGTTTGTGGTGTATGACTTGCCGGAT

-continued

```
CGCGATTGCGCTGCCCTTGCCTCGAATGGCGAATACTCTATTGCCGAT
GGTGGCGTCGCCAAATATAAGAACTATATCGACACCATTCGTCAAATT
GTCGTGGAATATTCCGATATCCGGACCCTCCTGGTTATTGGTGAGTTT
AAACACCTGCCTCCCCCCCCCTTCCCTTCCTTTCCCGCCGGCATCTT
GTCGTTGTGCTAACTATTGTTCCCTCTTCCAGAGCCTGACTCTCTTGC
CAACCTGGTGACCAACCTCGGTACTCCAAAGTGTGCCAATGCTCAGTC
AGCCTACCTTGAGTGCATCAACTACGCCGTCACACAGCTGAACCTTCC
AAATGTTGCGATGTATTTGGACGCTGGCCATGCAGGATGGCTTGGCTG
GCCGGCAAACCAAGACCCGGCCGCTCAGCTATTTGCAAATGTTTACAA
GAATGCATCGTCTCCGAGAGCTCTTCGCGGATTGGCAACCAATGTCGC
CAACTACAACGGGTGGAACATTACCAGCCCCCATCGTACACGCAAGG
CAACGCTGTCTACAACGAGAAGCTGTACATCCACGCTATTGGACCTCT
TCTTGCCAATCACGGCTGGTCCAACGCCTTCTTCATCACTGATCAAGG
TCGATCGGGAAAGCAGCCTACCGGACAGCAACAGTGGGGAGACTGGTG
CAATGTGATCGGCACCGGATTTGGTATTCGCCCATCCGCAAACACTGG
GGACTCGTTGCTGGATTCGTTTGTCTGGGTCAAGCCAGGCGGCGAGTG
TGACGGCACCAGCGACAGCAGTGCGCCACGATTTGACTCCCACTGTGC
GCTCCCAGATGCCTTGCAACCGGCGCCTCAAGCTGGTGCTTGGTTCCA
AGCCTACTTTGTGCAGCTTCTCACAAACGCAAACCCATCGTTCCTGTA
AGGCTTTCGTGACCGGGCTTCAAACAATGATGTGCGATGGTGTGGTTC
CCGGTTGGCGGAGTCTTTGTCTACTTTGGTTGT
```

The present invention also provides for the use of an isolated polynucleotide comprising a nucleic acid at least about 70%, 75%, or 80% identical, at least about 90% to about 95% identical, or at least about 96%, 97%, 98%, 99% or 100% identical to any of SEQ ID NOs:1-6, or fragments, variants, or derivatives thereof.

In certain aspects, the present invention relates to a polynucleotide comprising a nucleic acid encoding a functional or structural domain of *T. emersonii, H. grisea, T. aurantiacus* or *T. reesei* Cbh1 or Cbh2. For example, the domains of *T. reesei* Cbh 1 include, without limitation: (1) a signal sequence, from amino acid 1 to 33 of SEQ ID NO: 17; (2) a catalytic domain (CD) from about amino acid 41 to about amino acid 465 of SEQ ID NO: 17; and (3) a cellulose binding module (CBM) from about amino acid 503 to about amino acid 535 of SEQ ID NO: 17. The domains of *T. reesei* Cbh 2 include, without limitation: (1) a signal sequence, from amino acid 1 to 33 of SEQ ID NO: 18; (2) a catalytic domain (CD) from about amino acid 145 to about amino acid 458 of SEQ ID NO: 18; and (3) a cellulose binding module (CBM) from about amino acid 52 to about amino acid 83 of SEQ ID NO: 18.

The present invention also encompasses an isolated polynucleotide comprising a nucleic acid that is 70%, 75%, or 80% identical, at least about 90% to about 95% identical, or at least about 96%, 97%, 98%, 99% or 100% identical to a nucleic acid encoding a *T. emersonii, H. grisea, T. aurantiacus* or *T. reesei* Cbh1 or Cbh2 domain, as described above.

The present invention also encompasses variants of the cbh1 or cbh 2 genes, as described above. Variants may contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments, *T. emersonii, H. grisea, T. aurantiacus*, and *T. reesei* cbh1 or cbh2 polynucleotide variants can be produced for a variety of reasons, e.g., to optimize codon expression for a particular host (e.g., change codons in the *T. emersonii* cbh1 mRNA to those preferred by a host such as the yeast *Saccharomyces cerevisiae*). Codon-optimized polynucleotides of the present invention are discussed further below.

The present invention also encompasses an isolated polynucleotide comprising a nucleic acid that is 70%, 75%, or 80% identical, at least about 90% to about 95% identical, or at least about 96%, 97%, 98%, 99% or 100% identical to a nucleic acid encoding a fusion protein, where nucleic acid comprises a (1) a first polynucleotide, where the first polynucleotide encodes for a *T. emersonii, H. grisea, T. aurantiacus*, or *T. reesei* Cbh1 or Cbh2, or domain, fragment, variant, or derivative thereof; and (2) a second polynucleotide, where the second polynucleotide encodes for a *T. emersonii, H. grisea, T. aurantiacus*, or *T. reesei* CBH1 or CBH2, or domain, fragment, variant, or derivative thereof.

In certain embodiments, the nucleic acid encoding a fusion protein comprises a first polynucleotide encoding for a *T. emersonii* cbh1, *H. grisea* cbh1, or *T. aurantiacusi* cbh1, *T. emersonii* cbh1 and a second polynucleotide encoding for the CBM domain of *T. reesei* cbh1 or *T. reesei* cbh2. In particular embodiments of the nucleic acid encoding a fusion protein, the first polynucleotide is *T. emersonii* cbh1 and the second polynucleotide encodes for a CBM from *T. reesei* Cbh1 or Cbh2. In further embodiments of the fusion protein, the first and second polynucleotides are in the same orientation, or the second polynucleotide is in the reverse orientation of the first polynucleotide. In additional embodiments, the first polynucleotide is either N-terminal or C-terminal to the second polynucleotide. In certain other embodiments, the first polynucleotide and/or the second polynucleotide are encoded by codon-optimized polynucleotides, for example, polynucleotides codon-optimized for *S. cerevisiae*. In particular embodiments of the nucleic acid encoding a fusion protein, the first polynucleotide is a codon-optimized *T. emersonii* cbh1 and the second polynucleotide encodes for a codon-optimized CBM from *T. reesei* Cbh1 or Cbh2.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 1-6, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of any of SEQ ID NOs:1-6, or any fragment or domain specified as described herein.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990) 6:237-245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of SEQ ID NOs:1-6, or domains, fragments, variants, or derivatives thereof.

The polynucleotide of the present invention may be in the form of RNA or in the form of DNA, which DNA includes cDNA, genomic DNA, and synthetic DNA. The DNA may be double stranded or single-stranded, and if single stranded may be the coding strand or non-coding (anti-sense) strand. The coding sequence which encodes the mature polypeptide may be identical to the coding sequence encoding SEQ ID NO:11-14 or 17-18 or may be a different coding sequence which coding sequence, as a result of the redundancy or degeneracy of the genetic code, encodes the same mature polypeptide as the DNA of any one of SEQ ID NOs:1-6.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NO:11-14 or 17-18.

The polynucleotide encoding for the mature polypeptide of SEQ ID NO:11-14 or 17-18 may include: only the coding sequence for the mature polypeptide; the coding sequence of any domain of the mature polypeptide; and the coding sequence for the mature polypeptide (or domain-encoding sequence) together with non-coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

In further aspects of the invention, nucleic acid molecules having sequences at least about 90%, 95%, 96%, 97%, 98% or 99% identical to the nucleic acid sequences disclosed herein, encode a polypeptide having Cbh functional activity. By "a polypeptide having Cbh functional activity" is intended polypeptides exhibiting activity similar, but not necessarily identical, to a functional activity of the Cbh polypeptides of the present invention, as measured, for example, in a particular biological assay. For example, a Cbh functional activity can routinely be measured by determining the ability of a Cbh polypeptide to hydrolyze cellulose, or by measuring the level of Cbh activity.

Of course, due to the degeneracy of the genetic code, one of ordinary skill in the art will immediately recognize that a large portion of the nucleic acid molecules having a sequence at least about 90%, 95%, 96%, 97%, 98%, or 99% identical to the nucleic acid sequence of any of SEQ ID NOs:1-6, or fragments thereof, will encode polypeptides "having Cbh functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having Cbh functional activity.

Fragments of the full length gene of the present invention may be used as a hybridization probe for a cDNA library to isolate the full length cDNA and to isolate other cDNAs which have a high sequence similarity to the cbh1 genes of the present invention, or a gene encoding for a protein with similar biological activity. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

In certain embodiments, a hybridization probe may have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of bacterial or fungal cDNA, genomic DNA or mRNA to determine which members of the library the probe hybridizes to.

The present invention further relates to polynucleotides which hybridize to the hereinabove-described sequences if there is at least about 70%, at least about 90%, or at least about 95% identity between the sequences. The present invention particularly relates to polynucleotides which hybridize under stringent conditions to the hereinabove-described polynucleotides. As herein used, the term "stringent conditions" means hybridization will occur only if there is at least about 95% or at least about 97% identity between the sequences. In certain aspects of the invention, the polynucleotides which hybridize to the hereinabove described polynucleotides encode polypeptides which either retain substantially the same biological function or activity as the mature polypeptide encoded by the DNAs of any of SEQ ID NOs:1-6.

Alternatively, polynucleotides which hybridize to the hereinabove-described sequences may have at least 20 bases, at least 30 bases, or at least 50 bases which hybridize to a polynucleotide of the present invention and which has an identity thereto, as hereinabove described, and which may or may not retain activity. For example, such polynucleotides may be employed as probes for the polynucleotide of any of SEQ ID NOs: 1-6, for example, for recovery of the polynucleotide or as a diagnostic probe or as a PCR primer.

Hybridization methods are well defined and have been described above. Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

For example, genes encoding similar proteins or polypeptides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (see, e.g., Maniatis, 1989). Moreover, the entire sequences can be used directly to synthesize DNA probes by methods known to the skilled artisan such as random primers DNA labeling, nick translation, or end-labeling techniques, or RNA probes using available in vitro transcription systems.

In certain aspects of the invention, polynucleotides which hybridize to the hereinabove-described sequences having at least 20 bases, at least 30 bases, or at least 50 bases which hybridize to a polynucleotide of the present invention may be employed as PCR primers. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. Generally two short segments of the instant sequences may be used in polymerase chain reaction (PCR) protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Therefore, the nucleic acid sequences and fragments thereof of the present invention may be used to isolate genes encoding homologous proteins from the same or other fungal species or bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, Mullis et al., U.S. Pat. No. 4,683, 202; ligase chain reaction (LCR) (Tabor, S. et al., Proc. Acad. Sci. USA 82, 1074, (1985)); or strand displacement amplification (SDA, Walker, et al., *Proc. Natl. Acad. Sci. U.S.A.,* 89, 392, (1992)).

The polynucleotides of the present invention also comprise nucleic acids encoding a *T. emersonii, H. grisea, T. aurantiacus,* and *T. reesei* Cbh1 and/or Cbh2, or domain, fragment, variant, or derivative thereof, fused in frame to a marker sequence which allows for detection of the polypeptide of the present invention. The marker sequence may be a yeast selectable marker selected from the group consisting of URA3, HIS3, LEU2, TRP1, LYS2, ADE2 or SMR1.

Codon Optimization

As used herein the term "codon optimized coding region" means a nucleic acid coding region that has been adapted for expression in the cells of a given vertebrate by replacing at least one, or more than one, or a significant number, of codons with one or more codons that are more frequently used in the genes of that vertebrate.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 4, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Ter | TGA Ter |
|   | TTG Leu (L) | TCG Ser (S) | TAG Ter | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example at the "Codon Usage Database," and these tables can be adapted in a number of ways. See Nakamura, Y., et al. "Codon usage tabulated from the international DNA sequence databases: status for the year 2000" Nucl. Acids Res. 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Total |   |   |   |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Total |   |   |   |
| Ile | AUU | 196893 | 30.1 |
| Ile | AUC | 112176 | 17.2 |
| Ile | AUA | 116254 | 17.8 |
| Total |   |   |   |
| Met | AUG | 136805 | 20.9 |
| Total |   |   |   |
| Val | GUU | 144243 | 22.1 |
| Val | GUC | 76947 | 11.8 |
| Val | GUA | 76927 | 11.8 |
| Val | GUG | 70337 | 10.8 |
| Total |   |   |   |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Total |   |   |   |
| Pro | CCU | 88263 | 13.5 |
| Pro | CCC | 44309 | 6.8 |
| Pro | CCA | 119641 | 18.3 |

TABLE 2-continued

Codon Usage Table for *Saccharomyces cerevisiae* Genes

| Amino Acid | Codon | Number | Frequency per hundred |
|---|---|---|---|
| Pro | CCG | 34597 | 5.3 |
| Total | | | |
| Thr | ACU | 132522 | 20.3 |
| Thr | ACC | 83207 | 12.7 |
| Thr | ACA | 116084 | 17.8 |
| Thr | ACG | 52045 | 8.0 |
| Total | | | |
| Ala | GCU | 138358 | 21.2 |
| Ala | GCC | 82357 | 12.6 |
| Ala | GCA | 105910 | 16.2 |
| Ala | GCG | 40358 | 6.2 |
| Total | | | |
| Tyr | UAU | 122728 | 18.8 |
| Tyr | UAC | 96596 | 14.8 |
| Total | | | |
| His | CAU | 89007 | 13.6 |
| His | CAC | 50785 | 7.8 |
| Total | | | |
| Gln | CAA | 178251 | 27.3 |
| Gln | CAG | 79121 | 12.1 |
| Total | | | |
| Asn | AAU | 233124 | 35.7 |
| Asn | AAC | 162199 | 24.8 |
| Total | | | |
| Lys | AAA | 273618 | 41.9 |
| Lys | AAG | 201361 | 30.8 |
| Total | | | |
| Asp | GAU | 245641 | 37.6 |
| Asp | GAC | 132048 | 20.2 |
| Total | | | |
| Glu | GAA | 297944 | 45.6 |
| Glu | GAG | 125717 | 19.2 |
| Total | | | |
| Cys | UGU | 52903 | 8.1 |
| Cys | UGC | 31095 | 4.8 |
| Total | | | |
| Trp | UGG | 67789 | 10.4 |
| Total | | | |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Total | | | |
| Gly | GGU | 156109 | 23.9 |
| Gly | GGC | 63903 | 9.8 |
| Gly | GGA | 71216 | 10.9 |
| Gly | GGG | 39359 | 6.0 |
| Total | | | |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence will can vary significantly using this method, however, the sequence always encodes the same polypeptide.

Codon-optimized sequences of the present invention include those as set forth in Table 3 below:

TABLE 3

Synthetic cellobiohydrolase (CBH) genes constructed

| Donor organism/ Gene | DNA sequence used | Accession number and amino acid sequence |
|---|---|---|
| *Humicola grisea* cbh1 | GAATTCATGAGAACCGCTAAGTTCGCTACCTTGGCTGCCTTGGTTGCCTCTGCTGCTGC TCAACAAGCCTGTTCCTTGACTACTGAACGTCACCCATCTTTGTCTTGGAACAAGTGTA CTGCTGGTGGTCAATGTCAAACTGTCCAAGCCTCCATCACTTTGGACTCTAATTGGAG ATGGACCCACCAAGTCTCTGGTAGTACTAACTGTTACACCGGTAATAAGTGGGACACT TCTATTTGTACTGACGCTAAGTCTTGTGCTCAAAATTGTTGTGTTGATGGTGCTGATTA CACCTCCACTTATGGTATTACCACCAACGGTGACTCTTTGTCCTTGAAGTTCGTTACTA AAGGTCAACATTCCACCAACGTCGGTTCTAGAACCTACTTAATGGACGGTGAAGACAA GTACCAAACCTTCGAATTGTTGGGTAATGAATTTACCTTCGATGTCGATGTGTCTAACA | Accession No.: CAA35159 MRTAKFATLAALVASAAAQQACSL TTERHPSLSWNKCTAGGQCQTVQA SITLDSNWRWTHQVSGSTNCYTGN KWDTSICTDAKSCAQNCCVDGADY TSTYGITTNGDSLSLKFVTKGQHSTN VGSRTYLMDGEDKYQTFELLGNEFT FDVDVSNIGCGLNGALYFVSMDAD |

TABLE 3-continued

Synthetic cellobiohydrolase (CBH) genes constructed

| Donor organism/ Gene | DNA sequence used | Accession number and amino acid sequence |
|---|---|---|
| | TCGGTTGTGGTTTGAACGGTGCTTTATACTTCGTTTCTATGGACGCCGACGGTGGTTTG TCTCGTTACCCAGGTAATAAGGCTGGTGCCAAGTATGGTACCGGTTACTGTGATGCTC AATGCCCAAGAGACATTAAGTTCATCAACGGTGAAGCTAACATTGAAGGTTGGACTG GTTCTACCAACGACCCAAACGCTGGCGCCGGTAGATACGGTACCTGTTGTTCCGAAAT GGACATTTGGGAAGCCAACAACATGGCTACTGCTTTTACTCCACACCCATGTACCATC ATTGGTCAATCCAGATGTGAAGGTGACTCCTGTGGCGGTACCTACTCCAACGAAAGAT ACGCTGGTGTTTGTGATCCAGACGGTTCTGACTTCAACTCCTACAGACAAGGTAACAA GACTTTCTATGGTAAGGGTATGACTGTCGATACCACCAAGAAGATCACCGTCGTCACC CAATTCTTGAAGGACGCTAACGGTGATTTAGGTGAAATTAAAAGATTCTACGTCCAAG ATGGTAAGATCATCCCAAACTCTGAATCTACCATTCCAGGTGTTGAAGGTAATTCCAT CACTCAAGACTGGTGTGACAGACAAAAGGTTGCCTTCGGTGATATTGACGACTTCAAC AGAAAGGGTGGTATGAAGCAAATGGGTAAGCTTTGGCCGGTCCAATGGTCTTGGTTA TGTCTATTTGGGACGATACGCTTCCAACATGTTGTGGTTGGACTCCACCTTCCCAGTT GATGCTGCTGGTAAGCCAGGTGCCGAAAGAGGTGCTTGTCCAACTACTTCCGGTGTCC CAGCTGAAGTTGAAGCCGAAGCTCCAAATTCTAACGTTGTCTTCTCTAACATCAGATT CGGTCCAATCGGTTCCACAGTCGCTGGTTTGCCAGGTGCTGGTAATGGTGGTAATAAC GGTGGTAACCCACCACCACCAACCACTACCACTTCTTCTGCCCCAGCTACTACCACCA CCGCTTCTGCTGGTCCAAAGGCTGGTAGATGGCAACAATGTGGTGGTATTGGTTTCAC CGGTCCAACCCAATGTGAAGAACCATACATCTGTACCAAGTTGAACGACTGGTACTCT CAATGTTTATAACTCGAG (SEQ ID NO: 7) | GGLSRYPGNKAGAKYGTGYCDAQC PRDIKFINGEANIEGWTGSTNDPNAG AGRYGTCCSEMDIWEANNMATAFT PHPCTIIGQSRCEGDSCGGTYSNERY AGVCDPDGCDFNSYRQGNKTFYGK GMTVDTTKKITVVTQFLKDANGDL GEIKRFYVQDGKIIPNSESTIPGVEGN SITQDWCDRQKVAFGDIDDFNRKGG MKQMGKALAGPMVLVMSIWDDHA SNMLWLDSTFPVDAAGKPGAERGA CPTTSGVPAEVEAEAPNSNVVFSNIR FGPIGSTVAGLPGAGNGGNNGGNPP PPTTTTSSAPATTTTASAGPKAGRW QQCGGIGFTGPTQCEEPYICTKLND WYSQCL (SEQ ID NO: 11) |
| Thermoascus aurantiacus cbh1 | GAATTCATGTACCAAAGAGCTCTATTGTTCTCCTTCTTCTTGGCCGCCGCTAGAGCTCA TGAAGCCGGTACTGTCACCGCCGAAAACCACCCATCCTTGACTTGGCAACAATGTTCC TCTGGTGGTTCTTGTACTACTCAAAACGGGAAGGTTGTTATTGACGCTAACTGGAGAT GGGTTCACACTACCTCCGGTTACACCAACTGTTACACTGGTAACACTTGGGATACTTCC ATCTGTCCAGACGACGTTACCTGTGCTCAAAACTGTTTGGACGGTGCTGACTACTC CGGTACTTACGGTGTCACTACTTCTGGCAACGCGTTGAGATTGAACTTCGTCACCCAA TCTTCTGGTAAGAACATCGGTTCTAGATTGTACTTGTTGCAAGACGATACTACTTACCA AATCTTCAAGTTGTTGGGTCAAGAGTTCACTTTCGACGTTGATGTTTCCAACTTGCCTT GTGGTTTGAACGGTGCTTTGTACTTCGTTGCTATGGACGCCGACGGTAACTTATCCAAG TACCCAGGTAACAAGGCCGGTGCCAAGTACGGTACCGGTTACTGTGATTCTCAATGTC CAAGAGACCTAAAATTCATTAACGGTCAAGCTAACGTCGAAGGTTGGCAACCATCTGC TAACGATCCAAACGCCGGTGTCGGTAATCACGGTTCCTCCTGTGCTGAAATGGACGTT TGGGAAGCTAACTCTATCTCCACCGCCGTCACTCCACATCCATGTGATACCCCAGGTC AAACCATGTGTCAAGGTGATGATTGCGGTGGTACCTACTCTTCCACTAGATACGCTGG TACCTGTGACACCGACGGTTGTGATTTCAACCCATACCAACCAGGTAACCACTCTTTCT ACGGTCCAGGTAAGATTGTCGATACTTCTTCAAGTTCACTGTTGTCACTCAATTCATT ACCGACGATGGTACCCATCTGGTACCCTAACTGAAATTAAGAGATTCTACGTCCAAA ACGGTAAAGTCATTCCAACAATCCGAAAGCACCATTTCCGGTGTTACCGGTAACTCCAT CACCACTGAATACTGTACCGCTCAAAAGGCCGCCTTTGACAACACCGGTTTCTTCACC CATGGTGGTTTGCAAAAGATTTCTCAAGCCTTGGCTCAAGGTATGGTTTTGGTCATGTC CTTGTGGGATGACCACGCTGCTAACATGTTGTGGTTGGATTCTACTTACCCAACTGACG CTGATCCAGACACCCCAGGTGTTGCTAGAGGTACTTGTCCAACCACTTCTGGTGTTCCA GCTGACGTCGAATCTCAAAACCCTAACTCTTACGTTATCTACTCTAACATCAAGGTGG GTCCAATTAACTCCACCTTCACTGCTAACTAACTCGAG (SEQ ID NO: 8) | Accession No.: AAL16941 MYQRALLFSFFLAAARAHEAGTVT AENHPSLTWQQCSSGGSCTTQNGK VVIDANWRWVHTTSGYTNCYTGNT WDTSICPDDVTCAQNCALDGADYS GTYGVTTSGNALRLNFVTQSSGKNI GSRLYLLQDDTTYQIFKLLGQEFTFD VDVSNLPCGLNGALYFVAMDADGN LSKYPGNKAGAKYGTGYCDSQCPR DLKFINGQANVEGWQPSANDPNAG VGNHGSSCAEMDVWEANSISTAVTP HPCDTPGQTMCQGDDCGGTYSSTR YAGTCDTDGCDFNPYQPGNHSFYGP GKIVDTSSKFTVVTQFITDDGTPSGT LTEIKRFYVQNGKVIPQSESTISGVT GNSITTEYCTAQKAAFDNTGFFTHG GLQKISQALAQGMVLVMSLWDDHA ANMLWLDSTYPTDADPDTPGVARG TCPTTSGVPADVESQNPNSYVIYSNI KVGPINSTFTAN (SEQ ID NO: 12) |
| Talaromyces emersonii cbh1 | GAATTCATGCTAAGAAGAGCTTTACTATTGAGCTCTTCTGCTATCTTGGCCGTTAAGGC TCAACAAGCCGGTACCGCTACTGCTGAAAACCACCCTCCATTGACCTGGCAAGAATGT ACCGCTCCAGGTTCTTGTACCACCCAAAACGGTGCTGTCGTCTTGGACGCTAACTGGA GATGGGTCCACGACGTCAACGGTTACACTAACTGTTACACCGGTAACACTTGGGACCC AACTTACTGTCCAGACGACGAAACTTGCGCTCAAAACTGTGCCTTGGACGGTGCTGAC TACGAAGGTACTTACGGTGTTACCTCCTCTGGTTCTTCCTTGAAGTTGAACTTCGTCAC TGGTTCTAACGTCGGTTCCAGATTGTATTTGTTGCAAGATGACTCCACTTACCAAATCT TCAAGTTGTTGAACAGAGAATTTTCTTTCGACGTCGATGTGTCCAACTTGCCTTGTGGT TTGAACGGTGCTCTATACTTCGTTGCTATGGACGCTGATGGTGGTGTTTCCAAGTACCC AAACAACAAGGCTGGTGCCAAATACGGTACTGGTTACTGTGACTCAATGTCCACGT GACTTGAAGTTTATTGATGGTGAAGCTAATGTCGAAGGTTGGCAACCATCTTCTAACA ACGCTAACACTGGCATCGGTGACCACGGTTCTTGCTGTGCCGAAATGGACGTTTGGGA AGCCAACTCCATTTCCAACGCCGTCACTCCACACCCATGTGACACTCCAGGTCAAACT ATGTGTTCCGGCGATGACTGTGGTGGTACTTACTCTAACGATAGATACGCTGGTACCT GTGATCCAGACGGTTGCGACTTCAATCCATACAGAATGGGTAACACTTCCTTTTACGG TCCAGGCAAGATCATCGACACTACTAAGCCATTCACTGTTGTCACCCAATTCTTGACC GACGATGGTACTGATACCGGTACTTTGTCCGAAATCAAGAGATTCTACATCCAAAACT CTAACGTCATCCCACAACCAAATTCCGACATCTCTGGTGTCACTGGTAACTCCATTACC GAATTTTGTACCGCCCAAAAGCAAGCTTTCGGTACACCGACGACTTCTCTCAAC ACGGTGGTTTGGCTAAGATGGGTGCTGCTATGCAAGGTATGGTTTTGGTCATGTC TTTGTGGGACTACGCTGCTCAAATGTTGTGGTTGGACTCCGATTACCCAACCGAT GCCGACCCAACCACCCCTGGTATCGCTAGAGGTACCTGTCCAACTGACTCTGGTGTTC CATCTGACGTCGAATCCCAATCTCCAAACTCCTACGTCACTTACTCCAACATTAAATT GGTCCAATCAACTCCACTTTCACTGCTTCTTAACTCGAG (SEQ ID NO: 9) | Accession No.: AAL89553 MLRRALLLSSSAILAVKAQQAGTAT AENHPPLTWQECTAPGSCITQNGAV VLDANWRWVHDVNGYTNCYTGNT WDPTYCPDDETCAQNCALDGADYE GTYGVTSSGSSLKLNFVTGSNVGSR LYLLQDDSTYQIFKLLNREFSFDVDV SNLPCGLNGALYFVAMDADGGVSK YPNNKAGAKYGTGYCDSQCPRDLK FIDGEANVEGWQPSSNNANTGIGDH GSCCAEMDVWEANSISNAVTPHPCD TPGQTMCSGDDCGGTYSNDRYAGT CDPDGCDFNPYRMGNTSFYGPGKII DTTKPFTVVTQFLTDDGTDTGTLSEI KRFYIQNSNVIPQPNSDISGVTGNSIT TEFCTAQKQAFGDTDDFSQHGGLA KMGAAMQQGMVLVMSLWDDYAA QMLWLDSDYPTDADPTTPGIARGTC PTDSGVPSDVESQSPNSYVTYSNIKF GPINSTFTAS (SEQ ID NO: 13) |

TABLE 3-continued

Synthetic cellobiohydrolase (CBH) genes constructed

| Donor organism/ Gene | DNA sequence used | Accession number and amino acid sequence |
|---|---|---|
| Talaromyces emersonii cbh2 | GAATTCATGCGTAACTTGTTGGCCTTGGCTCCAGCCGCTTTGTTGGTTGGTGCTGCCGA AGCTCAACAATCCTTGTGGGGTCAATGCGGTGGTTCCTCCTGGACTGGTGCAACTTCCT GTGCCGCTGGTGCCACCTGTTCCACCATTAACCCATACTACGCTCAATGTGTTCCAGCC ACTGCCACTCCAACTACCTTGACTACCACCACTAAGCCAACCTCCACCGGTGGTGCTG CTCCAACCACTCCACCACCAACTACTACCGGTACTACCACCTCTCCAGTCGTCACCAG ACCTGCCTCCGCCTCCGGTAATCCATTCGAAGGTTATCAATTGTACGCTAACCCTTACT ACGCTTCTGAAGTCATTTCCTTGGCTATCCCAAGCTTCTCCGAGTTGGTCCCAAAG GCCTCCGAAGTTGCTAAGGTCCCTTCATTTGTCTGGTTAGATCAAGCTGCCAAGGTTCC ATCTATGGGTGATTACTTGAAGGATATTCAATCTCAAACGCTGCTGGTGCTGATCCA CCAATCGCCGGTATTTTCGTTGTTTACGATTTGCCAGATAGAGACTGTGCCGCCGCTGC TTCTAACGGTGAATTTTCTATCGCCAACAACGGTGTCGCTTTATACAAACAATATATCG ATTCCATTAGAGAACAATTAACCACTTACTCCGACGTCCATACCATCTTGGTTATCGAA CCAGACTCTTTGGCTAACGTTGTCACTAACTTGAACGTTCCAAAATGTGCTAACGCTCA AGATGCTTACTTGGAATGTATCAACTACGCTATTACCCAATTGGACTTGCCAAACGTT GCTATGTACTTGGACGCTGGTCATGCTGGTTGGGTTGGCAACCAACTTGGCCC CAGCTGCTCAATTATTCGCTTCTGTTTACAAGAACGCCTCTTCCCCAGCCTCTGTTAGA GGTTTGGCTACCAACGTGGCTAACTACAACGCCTGGTCCATTTCTAGATGTCCATCCTA CACTCAAGGTGACGCTAACTGTGATGAAGAAGATTACGTTAACGCTTTGGGTCCATTG TTCCAAGAACAAGGTTTCCCAGCTTACTTCATCATCGACACTTCCCGTAACGGTGTCGA ACCAACTAAGCAATCTCAATGGGGTGACTGGTGTAACGTTATTGGTACCGGTTTCGGT GTTAGACCAACCACCGACACTGGTAACCCATTGGAAGACGCTTTCGTTTGGGTCAAGC CAGGTGGTGAATCCGACGGTACCTCCAACACTACTAGCCCACGTTACGATTACCACTG TGGTTTGTCTGACGCTTTGCAACCAGCTCCAGAAGCTGGTACCTGGTTCCAAGCCTACT TCGAACAATTGTTGACTAACGCCAACCCATTGTTCTAACTCGAG<br>(SEQ ID NO: 10) | Accession No.: AAL78165<br>MRNLLALAPAALLVGAAEAQQSLW GQCGGSSWTGATSCAAGATCSTINP YYAQCVPATATPTTLTTTTKPTSTG GAAPTPPPTTTGTTTSPVVTRPASA SGNPFEGYQLYANPYYASEVISLAIP SLSSELVPKASEVAKVPSFVWLDQA AKVPSMGDYLKDIQSQNAAGADPPI AGIFVVYDLPDRDCAAAASNGEFSI ANNGVALYKQYIDSIREQLTTYSDV HTILVIEPDSLANVVTNLNVPKCAN AQDAYLECINYAITQLDLPNVAMYL DAGHAGWLGWQANLAPAAQLFAS VYKNASSPASVRGLATNVANYNAW SISRCPSYTQGDANCDEEDYVNALG PLFQEQGFPAYFIIDTSRNGVRPTKQ SQWGDWCNVIGTGFGVRPTTDTGN PLEDAFVWVKPGGESDGTSNTTSPR YDYHCGLSDALQPAPEAGTWFQAY FEQLLTNANPLF<br>(SEQ ID NO: 14) |
| Trichoderma reesei cbh1 | <u>ATGGTCTCCTTCACCTCCC</u>TGCTGGCCGGCGTTGCCGCTATCTCTGGTGTCCTAGCAGC CCCTGCCGCAGAAGTTGAACCTGTCGCAGTTGAGAAACGTGAGGCCGAAGCAGAAGC TCAATCGCTTGTACCCTACAATCCGAAACTCACCCACCATTGACCTGGCAAAGTGT TCTAGCGGTGGAACTTGTACTCAACAAACTGGTTCTGTTGTTATCGACGCTAACTGGA GATGGACACACGCCACTAACTCTTCTAACAATGTTACGACGGTAACACTTGGTCTTC CACTTTATGTCCAGATAACGAAACTTGTGCTAAGAATTGCTGTTTGGACGGTGCCGCC TACGCTTCTACCTACGGTGTTACCACCTCCGGTAACTCCTTGTCTATTGGTTTCGTCACT CAATCCGCTCAAAAGAACGTTGGTGCTAGATTGTACTTGATGGCTTCTGACACTACTT ATCAAGAATTTACTTTGTTGGGTAACGAATTTCTTTCGATGTTGACGTTTCCCAATTG CCATGTGGCTTGAACGGTGCTTTGTACTTTGTCTATGGATGCTGACGGTGGTGTTTC TAAGTACCCAACTAACACTGCCGGTCGTAAGTACGGTACTGGTTACTGTGATTCTCAA TGTCCACGTGACTTGAAGTTCATTAACGGTCAAGCCAACGTCGAAGGTTGGGAACCAT CCTCCAACAACGCTAACACCGGTATCGGTGGTCACGGTTCCTGTTGTTCCGAAATGGA CATCTGGGAAGCTAACATCTCTGAAGCTTTGACACACCCACATCCAATGTACCGTCA GGTCAAGAAATTTGTGAAGGTGATGGATGTGGTGGAACCTACTCTGATAACAGATACG GTGGTACTTGTGACCCAGACGGTTGTGACTGGAACCCATACAGATTGGGTAACACTTC TTTCTATGGTCCAGGTTCTTCTTTCACCTTGGATACCACCAAGAAGTTGACTGTTGTTA CCCAATTCGAAACTTCTGGTGCTATCAACAGATACGTTCAAAACGGTGTCACCTT CCAACAACCAAACGCTGAATTGGGTTCTTACTCTGGTAATGAATTGAACGACGACTAC TGTACCGCTGAAGAAGCTGAATTTGGTGGTTCCTCTTTCTCCGACAAGGGTGGTTTGAC CCAATTCAAGAAGGCTACCTCCGGTGGTATGGTTTTGGTTATGTCCTTGTGGGATGATT ACTACGCAAACATGTTATGGTTGACAGTACTTACCCAACTAACGAAACTTCCTCTAC TCCAGGTGCTGTCAGAGGTTCCTGTTCTACCTCTTCGGTGTTCCAGCTCAAGTTGAAT CTCAATCTCCAAACGCTAAGGTCACTTTCTCCAACATCAAGTTCGGTCCAATCGGTTCC ACTGGTAATCCATCTGGTGAAACCCTCCAGGTGGTAACAGAGGTACTACCACTACTC GTAGGCCAGCTACTACAACTGGTTCTTCCCAGGCCCAACCCAATCCCACTACGGTCA ATGTGGTGGTATCGGTTACTCTGGTCCAACCGTCTGCGCTTCTGGTACTACCTGTCAAG TTTTAAAC<u>CCATACTACTCTCAATGTTTGTAA</u><br>(SEQ ID NO: 15) | Accession No.: CAA49596<br>MVSFTSLLAGVAAISGVLAAPAAEV EPVAVEKREAEAEAQSACTLQSETH PPLTWQKCSSGGTCTQQTGSVVIDA NWRWTHATNSSTNCYDGNTWSSTL CPDNETCAKNCCLDGAAYASTYGV TTSGNSLSIGFVTQSAQKNVGARLY LMASDTTYQEFTLLGNEFSFDVDVS QLPCGLNGALYFVSMDADGGVSKY PTNTAGAKYGTGYCDSQCPRDLKFI NGQANVEGWEPSSNNANTGIGGHG SCCSEMDIWEANSISEALTPHPCTTV GQEICEGDGCGGTYSDNRYGGTCDP DGCDWNPYRLGNTSFYGPGSSFTLD TTKKLTVVTQFETSGAINRYVQNG VTPQQPNAELGSYSGNELNDDYCTA EEAEFGGSSFSDKGGLTQFKKATSG GMVLVMSLWDDYYANMLWLDSTY PTNETSSTPGAVRGSCSTSSGVPAQV ESQSPNAKVTFSNIKFGPIGSTGNPSG GNPPGGNRGTTTTRRPATTTGSSPGP TQSHYGQCGGIGYSGPTVCASGTTC QVLNPYYSQCL<br>(SEQ ID NO: 17)<br>Secretion signal: 1-33<br>catalytic domain: 41-465 cellulose-binding domain: 503-535 |
| Trichoderma reesei cbh2 | <u>ATGGTCTCCTTCACCTCCC</u>TGCTGGCCGGCGTTGCCGCTATCTCTGGTGTCCTAGCAGC CCCTGCCGCAGAAGTTGAACCTGTCGCAGTTGAGAAACGTGAGGCCGAAGCAGAAGC TGTCCCATTAGAAGAAACAAGCCTGCTCCTCTGTTTGGGGTCAATGTGGTGGTCAA AACTGGTCTGGTCCAACTTGTTGTGCTTCCGGTTCTACCTGTGTTTACTCCAACGACTA CTATTCCCAATGTTTGCCAGGTGCTGCTTCCTCCTCTTCAACTAGAGCTGCTTCTAC AACTTCTAGGGTCTCCCCAACCACTTCCAGATCTCTTCTGCTACTCCACCACCAGGTT CTACTACCACTAGAGTTCCACCAGTCGGTTCCGGTACTGCTACTTACTCTGGTAACCCT TTCGTCGGTGTTACTCCATGGGCTAACGCTTACTACGCTTCTGAAGTTCTTCTTGGCT ATCCCATCTTTGACTGGTGCTATGGCTACCGCTGCTGCTGTCAAAGTTCCATC CTTCATGTGGTTGGACACCTTGGACAAACCCATTAATGGAACAAACCTTGGCAGAC ATAAGGACTGCTAACAAGAACGGCGGTAACTACGCTGGTCAATTTGTTGTGTACGACT TGCCAGACAGAGACTGTGCTGCTTTGGCTTCCAACGGTGAATACTCCATCGCTGACGG TGGTGTCGCAAAGTACAAGAACTACATTGATACCATTAGACAAATCGTTTTGGTCGAA TCTGACATCAGAACCTTGTTAGTCATCGAACCAGATTCTTTAGCCAATTTAGTCACCAA CTTGGGTACTCCAAAGTGTGCTAACGCTCAATCTGCCTACTTAGAATGTATCAATTATG CAGTTACCCAATTGAACTTGCCAAACGTTGCTATGTACTTGGACGCTGGTCACGCCGG TTGGTTGGGTTGGCCAGCTAACCAAGACCCAGCCGCTCAATTATTCGCCAACGTTTAC AAGAATGCCTCTTCCCTAGAGCTTGCGTGGTTGGCTACTAACGTCGCTAACTACAA | Accession No.: AAA34210<br>MIVGILTTLATLATLAASVPLEERQA CSSVWGQCGGQNWSGPTCCASGST CVYSNDYYSQCLPGAASSSSSTRAA STTSRVSPTTSRSSSATPPPGSTTTRV PPVGSGTATYSGNPFVGVTPWANA YYASEVSSLAIPSLTGAMATAAAAV AKVPSFMWLDTLDKTPLMEQTLADI RTANKNGGNYAGQFVVYDLPDRDC AALASNGEYSIADGGVAKYKNYIDT IRQIVLVEYSDIRTLLVIEPDSLANLVT NLGTPKCANQSAYLECINYAVTQL NLPNVAMYLDAGHAGWLGWPANQ DPAAQLFANVYKNASSPRALRGLAT NVANYNGWNITSPPSYTQGNAVYN EKLYIHAIGRLLANHGWSNAFFITDQ GRSGKQPTGQQQWGDWCNVIGTGF GIRPSANTGDSLLDSFVWVKPGGEC |

TABLE 3-continued

Synthetic cellobiohydrolase (CBH) genes constructed

| Donor organism/ Gene | DNA sequence used | Accession number and amino acid sequence |
|---|---|---|
| | CGGTTGGAACATCACTTCTCCACCATCTTACACCCAAGGTAACGCTGTTTACAACGAA<br>AAGTTGTACATTCACGCTATCGGTCCATTATTGGCTAACCATGGTTGGTCTAACGCCTT<br>CTTCATCACCGACCAAGGTAGATCCGGTAAACAACCAACTGGTCAACAACAATGGGG<br>TGATTGGTGTAACGTCATCGGTACTGGTTTCGGTATCAGACCATCCGCTAACACTGGT<br>GATTCCTTGTTGGATTCCTTCGTCTGGGTTAAGCCAGGTGGTGAATGTGATGGCACCTC<br>TGATTCCTCTGCTCCAAGATTCGATTCCCACTGCGCCTTGCCAGACGCTTTGCAACCAG<br>CCCCACAAGCTGGTGCATGGTTCCAAGCTTACTTTGTCCAATTGTTGACCAAC<u>GCTAAC<br>CCATCTTTCTTGTAA</u><br>(SEQ ID NO: 16) | DGTSDSSAPRFDSHCALPDALQPAA<br>QAGAWFQAYFVQLLTNANPSFL<br>(SEQ ID NO: 18) |
| Xyn2 secretion signal + spacer | gaattcttaattaaAAACAAAATGGTCTCCTTCACCTCCCTGCTGGCCGGCGTTGCCGC<br>TATCTCTGGTGTCCTAGCAGCCCCTGCCGCAGAAGTTGAACCTGTCGCAGTTGAGAAAC<br>GTGAGGCCGAAGCAGAAGCTcccgggactc<br>(SEQ ID NO: 19) | Mvsftsllagvaaisgvlaapaaev<br>epvavekreaeaea<br>(SEQ ID NO: 20) |

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the Vector NTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function of the Entelechon back translation tool. Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, an entire polypeptide sequence, or fragment, variant, or derivative thereof is codon optimized by any of the methods described herein. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as *Saccharomyces cerevisiae*, in place of a codon that is normally used in the native nucleic acid sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

The codon-optimized coding regions can be versions encoding a Cbh1 or Cbh2 from *T. emersonii, H. grisea, T. aurantiacus, T. reesei*, or domains, fragments, variants, or derivatives thereof.

Codon optimization is carried out for a particular vertebrate species by methods described herein, for example, in certain embodiments codon-optimized coding regions encoding polypeptides of *T. emersonii, H. grisea, T. aurantiacus* or *T. reesei* Cbh1 or Cbh2, or domains, fragments, variants, or derivatives thereof are optimized according to yeast codon usage, e.g., *Saccharomyces cerevisiae*. In particular, the present invention relates to codon-optimized coding regions encoding polypeptides of *T. emersonii, H. grisea, T. aurantiacus* or *T. reesei* Cbh1 or Cbh2, or domains, variants, or derivatives thereof which have been optimized according to yeast codon usage, for example, *Saccharomyces cerevisiae* codon usage. Also provided are polynucleotides, vectors, and other expression constructs comprising codon-optimized coding regions encoding polypeptides of *T. emersonii, H. grisea, T. aurantiacus* or *T. reesei* Cbh1 or Cbh2, or domains, fragments, variants, or derivatives thereof, and various methods of using such polynucleotides, vectors and other expression constructs.

In certain embodiments described herein, a codon-optimized coding region encoding any of SEQ ID NOs:11-14 or 17-18, or domain, fragment, variant, or derivative thereof, is optimized according to codon usage in yeast (*Saccharomyces cerevisiae*). Alternatively, a codon-optimized coding region encoding any of SEQ ID NOs:11-14 or 17-18 may be optimized according to codon usage in any plant, animal, or microbial species.

Polypeptides of the Invention

The present invention further relates to the expression of *T. emersonii, H. grisea, T. aurantiacus* or *T. reesei* Cbh1 or Cbh2 polypeptides in a host cell, such as *Saccharomyces cerevisiae*. The sequences of *T. emersonii, H. grisea, T. aurantiacus* or *T. reesei* Cbh1 or Cbh2 polypeptides are set forth above and summarized in the table below:

| Organism and Protein | SEQ ID NO: |
| --- | --- |
| *H. grisea* Cbh1 | 11 |
| *T. aurantiacus* Cbh1 | 12 |
| *T. emersonii* Cbh1 | 13 |
| *T. emersonii* Cbh2 | 14 |
| *T. reesei* Cbh1 | 17 |
| *T. reesei* Cbh2 | 18 |

The present invention further encompasses polypeptides which comprise, or alternatively consist of, an amino acid sequence which is at least about 80%, 85%, 90%, 95%, 96%, 97%, 98%, 99% identical to, for example, the polypeptide sequence shown in SEQ ID NOs: 11-14 or 17-18, and/or domains, fragments, variants, or derivative thereof, of any of these polypeptides (e.g., those fragments described herein, or domains of any of SEQ ID NOs: 11-14 or 17-18).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence of SEQ ID NOs: 11-14 or 17-18 can be determined conventionally using known computer programs. As discussed above, a method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Also as discussed above, manual corrections may be made to the results in certain instances.

In certain embodiments, the polypeptide of the present invention encompasses a fusion protein comprising a first polypeptide, where the first polypeptide is a *T. emersonii* Cbh1, *H. grisea* Cbh1, or *T. aurantiacusi* Cbh1, *T. emersonii* Cbh2, *T. reesei* Cbh1 *T. reesei* Cbh2, or domain, fragment, variant, or derivative thereof, and a second polypeptide, where the second polypeptide is a *T. emersonii* Cbh1, *H. grisea* Cbh1, or *T. aurantiacusi* Cbh1, *T. emersonii* Cbh2, *T. reesei* Cbh1 or *T. reesei* Cbh2, or domain, fragment, variant, or derivative thereof. In particular embodiments the first polypeptide is *T. emersonii* Cbh1 and the second polynucleotide is a CBM from *T. reesei* Cbh1 or Cbh2. In further embodiments of the fusion protein, the first and second polypeptide are in the same orientation, or the second polypeptide is in the reverse orientation of the first polypeptide. In additional embodiments, the first polypeptide is either N-terminal or C-terminal to the second polypeptide. In certain other embodiments, the first polypeptide and/or the second polypeptide are encoded by codon-optimized polynucleotides, for example, polynucleotides codon-optimized for *S. cerevisiae*. In particular embodiments, the first polynucleotide is a codon-optimized *T. emersonii* cbh1 and the second polynucleotide encodes for a codon-optimized CBM from *T.* reesei Cbh1 or Cbh2. In certain other embodiments, the first polypeptide and the second polypeptide are fused via a linker sequence.

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least 80%, 85%, 90%, 95%, 96%, 97%, 98%, 99% similar to the polypeptide of any of SEQ ID NOs: 11-14 or 17-18, and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

The present invention further relates to a domain, fragment, variant, derivative, or analog of the polypeptide of any of SEQ ID NOs: 11-14 or 17-18.

Fragments or portions of the polypeptides of the present invention may be employed for producing the corresponding full-length polypeptide by peptide synthesis, therefore, the fragments may be employed as intermediates for producing the full-length polypeptides.

Fragments of Cbh polypeptides of the present invention encompass domains, proteolytic fragments, deletion fragments and in particular, fragments of *T. emersonii, H. grisea, T. aurantiacus* or *T. reesei* Cbh1 or Cbh2 polypeptides which retain any specific biological activity of the Cbh1 or Cbh2 protein. Polypeptide fragments further include any portion of the polypeptide which comprises a catalytic activity of the Cbh1 or Cbh2 protein.

The variant, derivative or analog of the polypeptide of any of SEQ ID NOs: 11-14 or 17-18, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants, derivatives and analogs are deemed to be within the scope of those skilled in the art from the teachings herein.

The polypeptides of the present invention further include variants of the polypeptides. A "variant' of the polypeptide can be a conservative variant, or an allelic variant. As used herein, a conservative variant refers to alterations in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. Allelic variants, though possessing a slightly different amino acid sequence than those recited above, will still have the same or similar biological functions associated with the *T. emersonii, H. grisea, T. aurantiacus* or *T. reesei* Cbh1 or Cbh2 protein.

The allelic variants, the conservative substitution variants, and members of the CBH1 or CBH2 protein family, will have an amino acid sequence having at least 75%, at least 80%, at least 90%, at least 95% amino acid sequence identity with a *T. emersonii, H. grisea, T. aurantiacus* or *T. reesei* Cbh1 or Cbh2 amino acid sequence set forth in any one of SEQ ID NOs:11-14 or 17-18. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N terminal, C terminal or internal extensions, deletions, or insertions into the peptide sequence shall not be construed as affecting homology.

Thus, the proteins and peptides of the present invention include molecules comprising the amino acid sequence of SEQ ID NOs: 11-14 or 17-18 or fragments thereof having a consecutive sequence of at least about 3, 4, 5, 6, 10, 15, 20, 25, 30, 35 or more amino acid residues of the *T. emersonii, H. grisea, T. aurantiacus* or *T. reesei* Cbh 1 or Cbh2 polypeptide sequence; amino acid sequence variants of such sequences wherein at least one amino acid residue has been inserted N- or C terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to rabbit, rat, porcine, bovine, ovine, equine and non-human primate species, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants may be generated to improve or alter the characteristics of the CBH polypeptides. For instance, one or more amino acids can be deleted from the N-terminus or C-terminus of the secreted protein without substantial loss of biological function.

Thus, the invention further includes *T. emersonii, H. grisea, T. aurantiacus* or *T. reesei* Cbh1 or Cbh2 polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306-1310

(1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081-1085 (1989).) The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the *T. emersonii, H. grisea, T. aurantiacus* or *T. reesei* Cbh1 or Cbh2 polypeptide, but retaining essential properties thereof. Generally, derivatives and analogs are overall closely similar, and, in many regions, identical to the *T. emersonii, H. grisea, T. aurantiacus* or *T. reesei* Cbh1 or Cbh2 polypeptides. The term "derivative" and "analog" when referring to *T. emersonii, H. grisea, T. aurantiacus* or *T. reesei* Cbh1 or Cbh2 polypeptides of the present invention include any polypeptides which retain at least some of the activity of the corresponding native polypeptide, e.g., the exoglucanase activity, or the activity of the its catalytic domain.

Derivatives of *T. emersonii, H. grisea, T. aurantiacus* or *T. reesei* Cbh1 or Cbh2 polypeptides of the present invention, are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins.

An analog is another form of a *T. emersonii, H. grisea, T. aurantiacus* or *T. reesei Cbh*1 or Cbh2 polypeptide of the present invention. An "analog" also retains substantially the same biological function or activity as the polypeptide of interest, i.e., functions as a cellobiohydrolase. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

Heterologous Expression of Cbh Polypeptides in Host Cells

In order to address the limitations of the previous systems, the present invention provides *T. emersonii, H. grisea, T. aurantiacus* or *T. reesei* Cbh1 or Cbh2 polypeptide, or domain, variant, or derivative thereof that can be effectively and efficiently utilized in a consolidated bioprocessing system.

One aspect of the invention is thus related to the efficient production of saccharolytic enzymes (cellulases and hemicellulases) to aid in the digestion of cellulose and generation of ethanol.

A "saccharolytic enzyme" is also referred to as a cellulase, and can correspond to any enzyme involved in cellulase digestion, metabolism and/or hydrolysis, including an endoglucananse, exoglucanase, or β-glucosidase. An exoglucanase can be, for example, a cellobiohydrolase.

In particular, the invention relates to the production of Cbh1 in a host organism. In certain embodiments, this host organism is yeast, such as *Saccharomyces cerevisiae*.

In certain embodiments of the present invention, a host cell comprising a vector which encodes and expresses *T. emersonii* CBH1 that is utilized for consolidated bioprocessing is co-cultured with additional host cells expressing one or more additional endoglucanases, cellobiohydrolases and/or β-glucosidases. In other embodiments of the invention, a host cell transformed with *T. emersonii* CBH1 is transformed with and expresses one or more heterologous endoglucanases, cellobiohydrolases or β-glucosidases. The endoglucanase, cellobiohydrolase and/or β-glucosidase can be any suitable endoglucanase, cellobiohydrolase and β-glucosidase derived from, for example, a fungal or bacterial source.

In certain embodiments of the invention, the endoglucanase(s) can be an endoglucanase I or an endoglucanase II isoform, paralogue or orthologue. In another embodiment, the endoglucanase expressed by the host cells of the present invention can be recombinant endo-1,4-β-glucanase. In certain embodiments of the present invention, the endoglucanase is an endoglucanase I from *Trichoderma reesei*.

In certain embodiments of the present invention the β-glucosidase is derived from *Saccharomycopsis fibuligera*. In certain embodiments, the β-glucosidase is a β-glucosidase I or a β-glucosidase II isoform, paralogue or orthologue. In certain other embodiments, the β-glucosidase expressed by the cells of the present invention can be recombinant β-glucanase I from a *Saccharomycopsis fibuligera* source.

In certain embodiments of the invention, the cellobiohydrolase(s) can be a cellobiohydrolase I and/or a cellobiohydrolase II isoform, paralogue or orthologue. In certain embodiments of the present invention the cellobiohydrolases are cellobiohydrolase I and II from *Trichoderma reesei*. In other embodiments, the cellobiohydrolases can be encoded by the polynucleotide sequences of SEQ ID NOs:15 and/or 16.

The transformed host cells or cell cultures, as described above, are measured for endoglucanase, cellobiohydrolase and/or β-glucosidase protein content. Protein content can be determined by analyzing the host (e.g., yeast) cell supernatants. In certain embodiments, the high molecular weight material is recovered from the yeast cell supernatant either by acetone precipitation or by buffering the samples with disposable de-salting cartridges. The analysis methods include the traditional Lowry method or protein assay method according to BioRad's manufacturer's protocol. Using these methods, the protein content of saccharolytic enzymes can be estimated.

The transformed host cells or cell cultures, as described above, can be further analyzed for hydrolysis of cellulase (e.g., by a sugar detection assay), for cellulase activity or cellulose utilization ((e.g., by measuring the individual cellulase (endoglucanase, cellobiohydrolase or β-glucosidase)) activity or by measuring total cellulase activity). Endoglucanase activity can be measured based on a reduction in cellulosic substrate viscosity and/or an increase in reducing ends determined by a reducing sugar assay. Cellobiohydrolase activity can be measured, for example, by using insoluble cellulosic substrates such as the amorphous substrate phosphoric acid swollen cellulose (PASC) or microcrystalline cellulose (Avicel) and determining the extent of the substrate's hydrolysis. β-glucosidase activity can be measured by a variety of assays, e.g., using cellobiose.

A total cellulase activity, which includes the activity of endoglucanase, cellobiohydrolase and β-glucosidase, will hydrolyze crystalline cellulose synergistically. Total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; and yeast plasmids. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Representative examples of such promoters are as follows:

| Gene | Organism | Systematic name | Reason for use/benefits |
|---|---|---|---|
| PGK1 | S. cerevisiae | YCR012W | Strong constitutive promoter |
| ENO1 | S. cerevisiae | YGR254W | Strong constitutive promoter |
| TDH3 | S. cerevisiae | YGR192C | Strong constitutive promoter |
| TDH2 | S. cerevisiae | YJR009C | Strong constitutive promoter |
| TDH1 | S. cerevisiae | YJL052W | Strong constitutive promoter |
| ENO2 | S. cerevisiae | YHR174W | Strong constitutive promoter |
| GPM1 | S. cerevisiae | YKL152C | Strong constitutive promoter |
| TPI1 | S. cerevisiae | YDR050C | Strong constitutive promoter |

Additional the E. coli, lac or trp, and other promoters known to control expression of genes in prokaryotic or lower eukaryotic cells. The expression vector also contains a ribosome binding site for translation initiation and a transcription terminator. The vector may also include appropriate sequences for amplifying expression, or may include additional regulatory regions.

In addition, the expression vectors may contain one or more selectable marker genes to provide a phenotypic trait for selection of transformed host cells such as URA3, HIS3, LEU2, TRP1, LYS2 or ADE2, dihydrofolate reductase or neomycin (G418) resistance for eukaryotic cell culture, or tetracycline or ampicillin resistance in E. coli.

The vector containing the appropriate DNA sequence as herein, as well as an appropriate promoter or control sequence, may be employed to transform an appropriate host to permit the host to express the protein.

Thus, in certain aspects, the present invention relates to host cells containing the above-described constructs. The host cell can be a higher eukaryotic cell, such as a mammalian cell, or a lower eukaryotic cell, such as a yeast cell, e.g., Saccharomyces cerevisiae, or the host cell can be a prokaryotic cell, such as a bacterial cell.

As representative examples of appropriate hosts, there may be mentioned: bacterial cells, such as E. coli, Streptomyces, Salmonella typhimurium; thermophilic or mesophilic bacteria; fungal cells, such as yeast; and plant cells, etc. The selection of an appropriate host is deemed to be within the scope of those skilled in the art from the teachings herein.

Appropriate fungal hosts include yeast. In certain aspects of the invention the yeast is Saccharomyces cervisiae, Kluveromyces lactus, Kluveromyces marxianus, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus and Schwanniomyces occidentalis.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In one aspect of this embodiment, the construct further comprises regulatory sequences, including, for example, a promoter, operably associated to the sequence. Large numbers of suitable vectors and promoters are known to those of skill in the art, and are commercially available. The following vectors are provided by way of example.

Yeast: Yeast vectors include those of five general classes, based on their mode of replication in yeast, YIp (yeast integrating plasmids), YRp (yeast replicating plasmids), YCp (yeast replicating plasmids with centromere (CEN) elements incorporated), YEp (yeast episomal plasmids), and YLp (yeast linear plasmids). With the exception of the YLp plasmids, all of these plasmids can be maintained in *E. coli* as well as in *Saccharomyces cerevisiae* and thus are also referred to as yeast shuttle vectors. In certain aspects, these plasmids contain two types of selectable genes: plasmid-encoded drug-resistance genes and cloned yeast genes, where the drug resistant gene is typically used for selection in bacterial cells and the cloned yeast gene is used for selection in yeast. Drug-resistance genes include ampicillin, kanamycin, tetracycline, neomycin and sulfometuron methyl. Cloned yeast genes include HIS3, LEU2, LYS2, TRP1, URA3, TRP1 and SMR1. pYAC vectors may also be utilized to clone large fragments of exogenous DNA on to artificial linear chromosomes.

In certain aspects of the invention, YCp plasmids, which have high frequencies of transformation and increased stability to due the incorporated centromere elements, are utilized. In certain other aspects of the invention, YEp plasmids, which provide for high levels of gene expression in yeast, are utilized. In additional aspects of the invention, YRp plasmids are utilized.

In certain embodiments, the vector comprises a (1) a first polynucleotide, where the first polynucleotide encodes for a *T. emersonii*, *H. grisea*, *T. aurantiacus*, or *T. reesei* Cbh1 or Cbh2, or domain, fragment, variant, or derivative thereof; and (2) a second polynucleotide, where the second polynucleotide encodes for a *T. emersonii*, *H. grisea*, *T. aurantiacus*, or *T. reesei* CBH1 or CBH2, or domain, fragment, variant, or derivative thereof.

In certain additional embodiments, the vector comprises a first polynucleotide encoding for a *T. emersonii* cbh1, *H. grisea* cbh1, or *T. aurantiacusi* cbh1, *T. emersonii* cbh1 and a second polynucleotide encoding for the CBM domain of *T. reesei* cbh1 or *T. reesei* cbh2. In particular embodiments, the vector comprises a first polynucleotide and a second polynucleotide, where the first polynucleotide is *T. emersonii* cbh1 and the second polynucleotide encodes for a CBM from *T. reesei* Cbh1 or Cbh2. In further embodiments, the first and second polynucleotides are in the same orientation, or the second polynucleotide is in the reverse orientation of the first polynucleotide. In additional embodiments, the first polynucleotide is either N-terminal or C-terminal to the second polynucleotide. In certain other embodiments, the first polynucleotide and/or the second polynucleotide are encoded by codon-optimized polynucleotides, for example, polynucleotides codon-optimized for *S. cerevisiae*. In additional embodiments, the first polynucleotide is a codon-optimized *T. emersonii* cbh1 and the second polynucleotide encodes for a codon-optimized CBM from *T. reesei* Cbh1 or Cbh2.

In particular embodiments, the vector of the present invention is a plasmid selected from the group consisting of pRDH101, pRDH103-112, pRDH118-121, pRDH123-129 and pDLG116-118. Diagrams of these plasmids are found in FIGS. 1-25.

Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223 3, pKK233-3, pDR540, pRIT5 (Pharmacia).

However, any other plasmid or vector may be used as long as they are replicable and viable in the host.

Promoter regions can be selected from any desired gene. Particular named yeast promoters include the constitute promoter ENO1, the PGK1 promoter, the TEF1 promoter and the HXT7 promoter. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Introduction of the construct into a host yeast cell, e.g., *Saccharomyces cerevisiae*, can be effected by lithium acetate transformation, spheroplast transformation, or transformation by electroporation, as described in Current Protocols in Molecular Biology, 13.7.1-13.7.10.

Introduction of the construct in other host cells can be effected by calcium phosphate transfection, DEAE-Dextran mediated transfection, or electroporation. (Davis, L., et al., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Following creation of a suitable host cell and growth of the host cell to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Yeast cell, e.g., *Saccharomyces cerevisiae*, employed in expression of proteins can be manipulated as follows. The Cbh polypeptides can be recovered and purified from recombinant cell cultures by methods including spheroplast preparation and lysis, cell disruption using glass beads, and cell disruption using liquid nitrogen.

Various mammalian cell culture systems can also be employed to express recombinant protein. Expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences.

Additional methods include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The Cbh polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Cbh polypeptides are provided in an isolated form, and, in certain aspects, are substantially purified. A recombinantly produced version of a Cbh polypeptide, including the secreted polypeptide, can be substantially purified using techniques described herein or otherwise known in the art, such as, for example, by the one-step method described in Smith and Johnson, *Gene* 67:31-40 (1988). Cbh polypeptides also can be purified from natural, synthetic or recombinant sources using techniques described herein or otherwise known in the art.

The Cbh polypeptides of the present invention may be in the form of the secreted protein, including the mature form, or may be a part of a larger protein, such as a fusion protein. It is often advantageous to include an additional amino acid sequence which contains secretory or leader sequences, pro-sequences, sequences which aid in purification, such as multiple histidine residues, or an additional sequence for stability during recombinant production.

Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the host production host. Methods for choosing appropriate signal sequences are well known in the art (see for example EP 546049; WO 9324631). The secretion signal DNA or facilitator may be located between the expression-controlling DNA and the instant gene or gene fragment, and in the same reading frame with the latter.

EXAMPLES

Materials and Methods

Media and Strain Cultivation

*Escherichia coli* strain DH5α (Invitrogen), or NEB 5 alpha (New England Biolabs) was used for plasmid transformation and propagation. Cells were grown in LB medium (5 g/L yeast extract, 5 g/L NaCl, 10 g/L tryptone) supplemented with ampicillin (100 mg/L), kanamycin (50 mg/L), or zeocin (20 mg/L). When zeocin selection was desired LB was adjusted to pH 7.0. Also, 15 g/L agar was added when solid media was desired.

Yeast strains were routinely grown in YPD (10 g/L yeast extract, 20 g/L peptone, 20 g/L glucose), YPC (10 g/L yeast extract, 20 g/L peptone, 20 g/L cellobiose), or YNB+glucose (6.7 g/L Yeast Nitrogen Base without amino acids, and supplemented with appropriate amino acids for strain, 20 g/L glucose) media with either G418 (250 mg/L unless specified) or zeocin (20 mg/L unless specified) for selection. 15 g/L agar was added for solid media.

Molecular Methods

Standard protocols were followed for DNA manipulations (Sambrook et al. 1989). PCR was performed using Phusion polymerase (New England Biolabs) for cloning, and Taq polymerase (New England Biolabs) for screening transformants, and in some cases Advantage Polymerase (Clontech) for PCR of genes for correcting auxotrophies. Manufacturers guidelines were followed as supplied. Restriction enzymes were purchased from New England Biolabs and digests were set up according to the supplied guidelines. Ligations were performed using the Quick ligation kit (New England Biolabs) as specified by the manufacturer. Gel purification was performed using either Qiagen or Zymo research kits, PCR product and digest purifications were performed using Zymo research kits, and Qiagen midi and miniprep kits were used for purification of plasmid DNA.

Yeast Transformation

A protocol for electrotransformation of yeast was developed based on Cho, K. M.; Yoo, Y. J.; Kang, H. S. "delta-Integration of endo/exo-glucanase and beta-glucosidase genes into the yeast chromosomes for direct conversion of cellulose to ethanol" *Enzyme And Microbial Technology,* 25: 23-30, (1999) and Ausubel, F. M.; Brent, R.; Kingston, R.; Moore, D.; Seidman, J.; Smith, J.; Struhl, K. Current Protocols in Molecular Biology. USA: John Wiley and Sons, Inc. 1994. Linear fragments of DNA are created by restriction enzyme digestion utilizing unique restriction sites within the plasmid. The fragments are purified by precipitation with 3M sodium acetate and ice cold ethanol, subsequent washing with 70% ethanol, and resuspension in USB dH2O (DNAse and RNAse free, sterile water) after drying in a 70° C. vacuum oven.

Yeast cells, e.g., *Saccharomyces cerevisiae*, for transformation are prepared by growing to saturation in 5 mL YPD cultures. 4 mL of the culture is sampled, washed 2× with cold distilled water, and resuspended in 640 µL cold distilled water. 80 µL of 100 mM Tris-HCl, 10 mM EDTA, pH 7.5 (10×TE buffer—filter sterilized) and 80 µL of 1M lithium acetate, pH 7.5 (10×liAc—filter sterilized) is added and the cell suspension is incubated at 30° C. for 45 minutes with gentle shaking. 20 µL of 1M DTT is added and incubation continues for 15 minutes. The cells are then centrifuged, washed once with cold distilled water, and once with electroporation buffer (1M sorbitol, 20 mM HEPES), and finally resuspended in 267 µL electroporation buffer.

For electroporation, 10 µg of linearized DNA (measured by estimation on gel) is combined with 50 µL of the cell suspension in a sterile 1.5 mL microcentrifuge tube. The mixture is then transferred to a 0.2 cm electroporation cuvette, and a pulse of 1.4 kV (200Ω, 25 µF) is applied to the sample using, e.g., the Biorad Gene Pulser device. 1 mL of YPD with 1M sorbitol adjusted to pH 7.0 (YPDS) is placed in the cuvette and the cells are allowed to recover for ~3 hrs. 100-200 µL cell suspension are spread out on YPDS agar plates with appropriate selection, which are incubated at 30° C. for 3-4 days until colonies appear.

Measurement of Cellulase Activity

CBH activity was detected using the substrate 4-Methylumbelliferyl-β-D-lactoside (MULac). Assays were carried out by mixing 504 of yeast supernatant with 50 µL of a 4 mM MUlac substrate solution made in 50 mM citrate buffer pH 5.5. The reaction was allowed to proceed for 30 minutes and then stopped with 1M Na2CO3. The fluorescence in each well was read in a microtiter plate reader (ex. 355 nm and em. 460 nm).

Activity on PASC and Avicel were measured using the protocol described in Den Haan et al. (2006). Briefly, yeast supernatants were incubated with cellulose at 4° C. to bind the cellulase. The cellulose was then filtered from the yeast supernatant, resuspended in citrate buffer and sodium azide, and incubated at 37° C. Accumulation of sugar was measured in the reaction by sampling and performing a phenol-sulfuric acid assay.

An Avicel conversion assay was also used to measure the cellulolytic activity of yeast strains expressing CBHs. 2% Avicel cellulose in 50 mM Na-acetate, pH 5.0 is suspended and mixed well to make the suspension homogenous. The homogenous suspension is pipetted to the tubes (0.5 ml each). 0.5 ml of sample is added to each tube on the substrate. The samples can be: enzyme in buffer, yeast culture filtrate, inactivated yeast culture filtrate (to detect the background sugars from cultivation media) or buffer for blank. The tubes are incubated at 35° C. with shaking (1000 rpm). The samples (100 μl) are then removed after a pre-determined hydrolysis time, e.g., 0 h, 4 h, 24 h and 48 h, into separate tubes and spun down. 50 μl of supernatant is added to 100 μl of DNS reagent into a microplate. This mixture is then heated at 99° C. for 5 minutes. The absorbance is measured at 595 nm. The glucose equivalent formed (reducing sugars) is analyzed using DNS calibration by glucose standard.

The Dinitrosalicylic Acid Reagent Solution (DNS), 1% includes the following 3,5-dinitrosalicylic acid: 10 g; Sodium sulfite: 0.5 g; Sodium hydroxide: 10 g; water to 1 liter. The DNS is calibrated by glucose (using glucose samples with conc. 0, 1, 2, 3, 4, 5 and 6 g/l, the slope [S] is calculated, for DNS from May 8, 2007 S=0.0669). The DNS solution can be stored at 4° C. for several months.

Cellulase activity is also measured by the resorufin-cellobioside assay (MarkerGene Fluorecent Cellulase Assay Kit, MGT Inc.).

Example 1

Cloning of Codon-Optimized cbh Genes and their Expression in *Saccharomyces cerevisiae*

Cellobiohydrolase (cbh) genes from various fungal organisms (as indicated in Table 4 below) were codon-optimized for expression in the yeast *Saccharomyces cerevisiae*. The software package "synthetic gene designer" (Wu, G., et al., *The Synthetic Gene Designer: A flexible web platform to explore sequence manipulation for heterologous expression. Protein Expr Purif.* 47(2):441-5 (2006) applying the CAI codon usage table suggested by Carbone et al. 2003 was utilized to generate an initial sequence that had a codon adaptation index (CAI) of 1.0, where three-letter sequences encoding for individual amino acid codons were replaced with those three-letter sequences known to be most frequently used in *S. cerevisiae* for the corresponding amino acid codons.

The initial codon-optimized sequence generated by this software was then further modified. In particular, the software was utilized to identify certain stretches of sequence (e.g., sequences with 4, 5, 6, 7, 8, 9, or 10 contiguous A's or T's), and replace these sequences with three-letter sequences corresponding to the second most frequently utilized three-letter sequences in *S. cerevisiae*.

In addition, for molecular cloning purposes, the website software was used to similarly replace certain restriction enzyme, including PacI, AscI, BamHI, BglII, EcoRI and XhoI.

Finally other DNA software (DNAman) was used to check the DNA sequence for direct repeats, inverted repeats and mirror repeats with lengths of 10 bases or longer. These sequences were modified by manually replacing codons with "second best" codons. These steps resulted in a CAI of approximately 0.8 to 0.85. A summary of these cbh1 genes, the Accession Number of the corresponding encoded amino acid sequence, and the codon bias index are summarized below:

TABLE 4

Codon-optimized cellobiohydrolase (CBH) genes

| Donor organism | Gene name | Accession number | Codon bias index |
|---|---|---|---|
| *Humicola grisea* | cbh1 | CAA35159 | 0.80 |
| *Thermoascus aurantiacus* | cbh1 | AAL83303 | 0.83 |

TABLE 4-continued

Codon-optimized cellobiohydrolase (CBH) genes

| Donor organism | Gene name | Accession number | Codon bias index |
|---|---|---|---|
| *Talaromyces emersonii* | cbh1 | AAL89553 | 0.80 |
| *Talaromyces emersonii* | cbh2 | AAL78165 | 0.78 |

The codon-optimized cbh's listed in Table 4 above were cloned into the yeast expression vector YEpENO-BBH (ENO1 promoter/terminator). Initially, the synthetic cbh genes were cloned onto the plasmid pUC57. These four vectors were digested with EcoRI and XhoI to excise the cbh genes which were subsequently cloned into an EcoRI and XhoI digested YEpENO-BBH. The yeast expression vector YEpENO-BBH was created to facilitate heterologous expression under control of the *S. cerevisiae* enolase 1 (ENO1) gene promoter and terminator and to ease combination of gene cassettes as the expression cassette form this vector could be excised with a BamHI, BglII digest. YEpENO1 (Den Haan, R. et al., "Functional expression of cellobiohydrolases in *Saccharomyces cerevisiae* towards one-step conversion of cellulose to ethanol," *Enzyme and Microbial Technology*, 40:1291-1299 (2007)) contains the YEp352 backbone with the ENO1 gene promoter and terminator sequences cloned into the BamHI and HindIII sites. This plasmid was digested with BamHI and the overhang filled in with Klenow polymerase and dNTPs to remove the BamHI site. The plasmid was re-ligated to generate YEpENO-B.

Using the same method, the BglII and then the HindIII sites were subsequently destroyed to create YEpENO-BBHtemplate. YEpENO-BBHtemplate was used as template for a PCR reaction with primers ENOBB-left (5'-GATCGGATC-CCAATTAATGTGAGTTACCTCA-3' SEQ ID NO: 21) and ENOBB-right (5'-GTACAAGCTTAGATCTCCTATGCG-GTGTGAAATA-3' SEQ ID NO: 22) in which the ENO1 cassette was amplified together with a 150 by flanking region upstream and 220 bp downstream. This product was digested with BamHI and HindIII and the over hangs filled in by treatment with Klenow polymerase and dNTPs and cloned between the two PvuII sites on yENO1 effectively replacing the original ENO1 cassette and generating YEpENO-BBH.

This created the plasmids pRDH103 (with Hgcbh1), pRDH104 (with Tacbh1), pRDH105 (with Tecbh1) and pRDH106 (with Tecbh2) with the cbh encoding genes placed under transcriptional control of the ENO1 promoter and terminator.

Sequences of *T. reesei* cbh1 and cbh2 were similarly codon-optimized and cloned into the YEpENO-BBH vector as described above.

A 1494 bp fragment encoding the *T. reesei* cbh2 gene was amplified from the plasmid pBZD_10631_20641, with primers sCBH1/2-L (5'-GACTGAATTCATAATGGTCTCCT-TCACCTCC-3' SEQ ID NO: 23) and sCBH2 R (5'-CAGTCTCGAGTTACAAGAAAGATGGGTTAGC-3' SEQ ID NO: 24), digested with EcoRI and XhoI and cloned into the EcoRI and XhoI sites of pJC1 (La Grange, D. C., et al., "Expression of a *Trichoderma reesei* β-xylanase gene (XYN2) in *Saccharomyces cerevisiae*," Applied and Environmental Microbiology 62:1036-1044 (1996); Crous et al. 1995; Current Genetics 28:467-473) placing it under transcriptional control of *S. cerevisiae* phosphoglycerate kinase 1 (PGK1) gene promoter and terminator. This plasmid was designated pRDH107. Subsequently the expression cassettes from pRDH103, pRDH104 and pRDH105 were excised with BamHI and BglII digestion and cloned into the BamHI site of pRDH107 to yield pRDH118, pRDH120, pRDH108 and pRDH109, respectively. pRDH109 contains the same expression cassettes as pRDH108 but in pRDH108 the gene expression cassettes are in the reverse orientation relative to each other. These plasmids and their basic genotypes are summarized in Table 5 below:

TABLE 5

Plasmids used in this example. (ENO1$_{P/T}$ = Enolase 1 gene promoter/terminator; PGK1$_{P/T}$ = phosphoglycerate kinase 1 gene promoter & terminator; T.r. = *Trichoderma reesei*; H.g. = *Humicola grisea*; T.a. = *Thermoascus aurantiacus*; T.e. = *Talaromyces emersonii*, BGL1 = β-glucosidase 1 from *Saccharomycopsis fibuligera*)

| Strain/Plasmid | Genotype | Source/Reference |
|---|---|---|
| Yeast strain: | | |
| *Saccharomyces cerevisiae* Y294 | α leu2-3, 112 ura3-52 his3 trp1-289 | ATCC 201160 |
| Plasmids: | | |
| pBKD1-BGLI | bla KanMX PGK1$_P$-S.f. bgl1-PGK1$_T$ | |
| pBKD2-sEGI | bla KanMX ENO1$_P$-sT.r. eg1-ENO1$_T$ | |
| pBKD1-BGLI-sEGI | bla KanMX ENO1$_P$-sT.r. eg1-ENO1$_T$ & PGK1$_P$-S.f. bgl1-PGK1$_T$ | |
| YEpENO-BBH | bla URA3 ENO1$_{PT}$ | |
| pJC1 | bla URA3 PGK$_{PT}$ | La grange et al. (1996) |
| pRDH103 | bla URA3 ENO1$_P$-sH.g.cbh1-ENO1$_T$ | |
| pRDH104 | bla URA3 ENO1$_P$-sT.a.cbh1-ENO1$_T$ | |
| pRDH105 | bla URA3 ENO1$_P$-sT.e.cbh1-ENO1$_T$ | |
| pRDH106 | bla URA3 ENO1$_P$-sT.e.cbh2-ENO1$_T$ | |
| pRDH107 | bla URA3 PGK1$_P$-sT.r.cbh2-PGK1$_T$ | |
| pRDH108 | bla URA3 PGK1$_P$-sT.r.cbh2-PGK1$_T$ & ENO1$_P$-sT.e.cbh1-ENO1$_T$ | |
| pRDH118 | bla URA3 PGK1$_P$-sT.r.cbh2-PGK1$_T$ & ENO1$_P$-sH.g.cbh1-ENO1$_T$ | |
| pRDH120 | bla URA3 PGK1$_P$-sT.r.cbh2-PGK1$_T$ & ENO1$_P$-sT.a.cbh1-ENO1$_T$ | |

Subsequently, these constructs were utilized to transform *S. cerevisiae* strain Y294 as listed above. The transformed Y294 strains were made autoselective by disruption of the FUR1 gene (transformation & disruption events were confirmed by PCR analysis). Subsequently these strains as well as a reference strain and the strain expressing the *T. reesei* cbh1 (original coding sequence) were assayed for CBH activity with the adsorption reaction sugar detection protocol. The detailed protocol can be found in Den Haan et al., "Functional expression of cellobiohydrolases in *Saccharomyces cerevisiae* towards one-step conversion of cellulose to ethanol," *Enzyme Microb. Technol.* 40: 1291-1299 (2007).

The plasmid constructs containing the various cbh genes constructed are summarized in Table 5, along with data on the status of the yeast transformants and auto-selectivity thereof (transformation & disruption events were confirmed by PCR analysis). Some of these strains, together with a reference strain, were assayed for Cbh activity and dry weight determination.

As shown in Table 6, below, the synthetic *Humicola grisea* cbh1, *Thermoascus aurantiacus* cbh1, *Talaromyces emersonii* cbh1 and cbh2 yield higher specific activities than *Trichoderma reesei* cbh1, with *T. emersonii* cbh1 yielding a specific activity about ten fold higher than *T. reesei* cbh1 when Avicel is used as a cellulosic substrate. This is a significant improvement over previously-created cellulose degrading *S. cerevisiae* strains.

Example 2

Cloning of cbh Combination Constructs and their Expression in *Saccharomyces cerevisiae*

Additional combination constructs and strain completion are summarized as follows in Table 6.

Four constructs combining the *H. grisea* cbh1 and *T. aurantiacus* cbh1 with the synthetic *T reesei* cbh2 were assayed. This was done to capitalize on the greater activity of these cbh1's on avicel as was found earlier. The plasmids with combinations of cellulases were constructed by cloning the relevant gene cassette (ENOp-cbh-ENOt) from the YEp-ENO-BBH based plasmid as a BamHI-BglII fragment into the unique BamHI site of the pJC1 based plasmid(s).

Assays were conducted on strains containing the plasmids pRDH118, pRDH119, pRDH120, pRDH121 on PASC and Avicel cellulosic substrates. Assay results obtained are given in Table 6 below:

TABLE 6

Synthetic CBH genes cloned into yeast expression vectors, transformed to *S. cerevisiae* Y294 and assayed. (ENO1p/t = Enolase 1 gene promoter & terminator; PGK1p/t = phosphoglycerate kinase 1 gene promoter & terminator; ADH2p/t = Alcohol dehydrogenase 2 gene promoter & terminator; T.r. = *Trichoderma reesei*; H.g. = *Humicola grisea*; T.a. = *Thermoascus aurantiacus*; T.e. = *Talaromyces emersonii*)

| Plasmid | Expression Cassette(s) | Transformed to Y294 | FUR1 disrupted | Act. (PASC) (mU/gDCW) | Act. (Avicel) (mU/gDCW) |
|---|---|---|---|---|---|
| yENO1 | ENO1p/t | ✓ | ✓ | 2.68 ± 1.1 | 2.99 ± 0.7 |
| pDLG77 | ADH2p/t-T.r.cbh1 $^a$ro = expression cassettes are in the reverse orientation (native) | ✓ | ✓ | | 8.8 ± 2.4 |
| pRDH101 | ENO1p/t-sT.r.cbh1 | ✓ | ✓ | nc | 6.5 ± 1.4 |
| pRDH103 | ENO1p/t-sH.g.cbh1 | ✓ | ✓ | 32.82 ± 6.5 | 34.85 ± 2.0 |
| pRDH104 | ENO1p/t-sT.a.cbh1 | ✓ | ✓ | 38.56 ± 5.9 | 38.15 ± 4.1 |
| pRDH105 | ENO1p/t-sT.e.cbh1 | ✓ | ✓ | 75.60 ± 13.1 | 21.42 ± 6.1 |
| pRDH106 | ENO1p/t-sT.e.cbh2 | ✓ | ✓ | 27.48 ± 10.0 | 14.09 ± 4.3 |
| pRDH107 | PGK1p/t-sT.r.cbh2 | ✓ | ✓ | 82.73 ± 3.3 | 33.8 ± 3.3 |
| pRDH108 | PGK1p/t-sT.r.cbh2 & ENO1p/t-sT.e.cbh1(ro)$^a$ | ✓ | ✓ | 174.35 ± 6.5 | 40.5 ± 4.9 |
| pRDH109 | PGK1p/t-sT.r.cbh2 & ENO1p/t-sT.e.cbh1 | ✓ | ✓ | 180.09 ± 4.9 | 67.3 ± 4.2 |
| pRDH110 | PGK1p/t-sT.e.cbh2 | ✓ | ✓ | 11.43 ± 2.0 | 13.6 ± 4.6 |

TABLE 6-continued

Synthetic CBH genes cloned into yeast expression vectors, transformed to *S. cerevisiae* Y294 and assayed. (ENO1p/t = Enolase 1 gene promoter & terminator; PGK1p/t = phosphoglycerate kinase 1 gene promoter & terminator; ADH2p/t = Alcohol dehydrogenase 2 gene promoter & terminator; T.r. = *Trichoderma reesei*; H.g. = *Humicola grisea*; T.a. = *Thermoascus aurantiacus*; T.e. = *Talaromyces emersonii*)

| Plasmid | Expression Cassette(s) | Transformed to Y294 | FUR1 disrupted | Act. (PASC) (mU/gDCW) | Act. (Avicel) (mU/gDCW) |
|---|---|---|---|---|---|
| pRDH111 | PGK1p/t-sT.e.cbh2 & ENO1p/t-sT.e.cbh1 | ✓ | nc | nc | nc |
| pRDH112 | PGK1p/t-sT.e.cbh2 & ENO1p/t-sT.e.cbh1(ro) | ✓ | ✓ | nc | 35.99 ± 5.4 |
| pRDH117 | ENO1p/t-sT.e.cbh1 & ENO1p/t-sT.e.cbh2 | ✓ | ✓ | 151.17 ± 7.73 | 36.09 ± 4.42 |
| pRDH118 | PGK1p/t-sT.r.cbh2 & ENO1p/t-sH.g.cbh1 | ✓ | ✓ | nc | 106.2 ± 6.8 |
| pRDH119 | PGK1p/t-sT.r.cbh2 & ENO1p/t-sH.g.cbh1(ro) | ✓ | ✓ | nc | 92.0 ± 2.9 |
| pRDH120 | PGK1p/t-sT.r.cbh2 & ENO1p/t-sT.a.cbh1 | ✓ | ✓ | nc | 32.7 ± 5.7 |
| pRDH121 | PGK1p/t-sT.r.cbh2 & ENO1p/t-sT.a.cbh1(ro) | ✓ | ✓ | nc | 46.5 ± 4.5 |
| pDLG116 | ENO1p/t-XS-sT.e.cbh1 | ✓ | ✓ | nc | 21.1 ± 3.1 |
| pDLG117[c] | ENO1p/t-XS-CBM-sT.e.cbh1 | ✓ | ✓ | nc | 50.4 ± 22.4 |

[a] ro = expression cassettes are in the reverse orientation
[b] nc = not complete
[c] = N terminal attached CBM from *T. reesei* cbh2 (cel6A)

Strains expressing the combination of synthetic T.r.cbh2 and T.e.cbh1 yielded higher activity levels on PASC than measured for the individual genes. The activity seemed to be additive and not synergistic on this substrate and it will be interesting to see whether greater synergy is observed on a crystalline substrate. The cbh1 from *T. emersonii* yielded a level of 21.42±6.1 mU/gDCW on avicel.

The combination of the *H. grisea* cbh1 and *T. reesei* cbh2 with the Y294+pRDH118::fur1 strain, with Avicel as the cellulosic substrate, yielded 106.2±6.8 mU/gDCW.

Equivalent YBE strains having integrated bgl1 and eg1 genes are analyzed for growth on cellulosic substrates.

Example 3

Cloning and Expression of *T. emersonii* cbh1 Fusion Constructs and their Expression in *Saccharomyces cerevisiae*

The native *T. emersonii* CBH1 does not have a cellulose binding module (CBM), however when expressed in *S. cerevisiae* it showed the best specific activity.

As described further below, a fusion construct of CBM from *T. reesei* Cbh2 and linker to the *T. emersonii* CBH1 was created. In the first construct the *T. reesei* cbh2 sequence encoding for the CBM domain was fused at the N-terminal side of the *T. emersonii* cbh1 and the second construct the *T. reesei* cbh1 encoding for the CBM was fused to the C terminal side of the *T. emersonii* CBH1. Both of these constructs also contain the *T. reesei* xyn2 secretion signal sequence to direct the *T. emersonii* CBH1 to the extracellular medium. A third construct only replaces the native secretion signal with the *T. reesei* xyn2 secretion signal.

An *S. cerevisiae* FUR1-disrupted Y294 strain was transformed with the following constructs: (1) pDLG117 (*T. emersonii* cbh1 with N-terminal CBM [from T.r.cbh2], T.r.xyn2 secretion signal); (2) pDLG116 (*T. emersonii* cbh1 with T.r.xyn2 secretion signal); and (3) yENO1 (Negative control strain).

The adsorption-reaction-sugar detection assay was performed as described above. The results attained are presented in FIG. 26. CBH activity for the pDLG117 construct was 51.2±6.6 mU/gDCW, for the pDLG116 construct was 17.3±1.4 mU/gDCW, and for the yENO1 negative control was 3.6±0.1 mU/gDCW.

The attachment of the N-terminal CBM to the *T. emersonii* cbh1 did not have a detrimental effect on the secretion of the protein. The CBM also allowed better adsorption of the recombinant CBH to the avicel substrate leading to better assayed activity. Furthermore, as shown in FIG. 27, the pDLG117 and pDLG116 plasmids did not have a detrimental effect on growth of the cell, as measured by dry cell weight.

TABLE 7

Further combinations of cellulases for expression in *S. cerevisiae*
(ENO1p/t = Enolase 1 gene promoter & terminator; PGK1p/t = phosphoglycerate kinase 1 gene promoter & terminator; s = synthetic; Tr = *Trichoderma reesei*; Te = *Talaromyces emersonii*; NCBM = N-terminally attached carbohydrate binding moiety and linker region from sTrcbh2; CCBM = C-terminally attached carbohydrate binding moiety and linker region from sTrcbh1).

| Plasmid Name | Expression cassette(s) | Transformed to *S. cerevisiae* Y294 | FUR1 disrupted | Transformed to *S. cerevisiae* YBE | FUR1 disrupted |
|---|---|---|---|---|---|
| pRDH123 | PGK1p/t-sTrcbh2 & ENO1p/t-NCBM-sTecbh1 | ✓ | ✓ | ✓ | ✓ |

TABLE 7-continued

Further combinations of cellulases for expression in *S. cerevisiae*
(ENO1p/t = Enolase 1 gene promoter & terminator; PGK1p/t = phosphoglycerate kinase 1 gene promoter & terminator; s = synthetic; Tr = *Trichoderma reesei*; Te = *Talaromyces emersonii*; NCBM = N-terminally attached carbohydrate binding moiety and linker region from sTrcbh2; CCBM = C-terminally attached carbohydrate binding moiety and linker region from sTrcbh1).

| Plasmid Name | Expression cassette(s) | Transformed to *S. cerevisiae* Y294 | FUR1 disrupted | Transformed to *S. cerevisiae* YBE | FUR1 disrupted |
|---|---|---|---|---|---|
| pRDH124 | PGK1p/t-sTrcbh2 & ENO1p/t-NCBM-sTecbh1 [RO]* | ✓ | ✓ | ✓ | ✓ |
| pRDH125 | PGK1p/t-sTrcbh2 & ENO1p/t-CCBM-sTecbh1 | ✓ | ✓ | ✓ | ✓ |
| pRDH126 | PGK1p/t-sTrcbh2 & ENO1p/t-CCBM-sTecbh1 [RO] | ✓ | | ✓ | ✓ |
| pRDH127 | PGK1p/t-CCBM-sTecbh1 | ✓ | ✓ | | |
| pRDH128 | ENO1p/t-NCBM-sTecbh1 & PGK1p/t-CCBM-sTecbh1 | ✓ | ✓ | ✓ | ✓ |
| pRDH129 | ENO1p/t-NCBM-sTecbh1 & PGK1p/t-CCBM-sTecbh1 [RO] | ✓ | ✓ | ✓ | ✓ |

*The gene expression cassettes on this plasmid are in the reverse orientation relative to each other The constructs above are used to transform *S. cerevisiae* Y294 and YBE strains as described above. Cbh1 activity is measured according to assays described above.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A polynucleotide encoding a cellobiohydrolase polypeptide which comprises an amino acid sequence at least 90% identical to the amino acid sequence of SEQ ID NO: 13, wherein said polypeptide has a functional cellobiohydrolase activity, wherein said polynucleotide comprises a codon-optimized nucleic acid sequence that encodes said cellobiohydrolase polypeptide;

(a) wherein about 16 phenylalanine codons of the codon-optimized nucleic acid sequence are TTT;

wherein about 26 leucine codons of the codon-optimized nucleic acid sequence are TTA;

wherein about 15 isoleucine codons of the codon-optimized nucleic acid sequence are ATT;

wherein about 10 methionine codons of the codon-optimized nucleic acid sequence are ATG;

wherein about 24 valine codons of the codon-optimized nucleic acid sequence are GTT;

wherein about 39 serine codons of the codon-optimized nucleic acid sequence are TCT;

wherein about 25 proline codons of the codon-optimized nucleic acid sequence are CCT;

wherein about 44 threonine codons of the codon-optimized nucleic acid sequence are ACT;

wherein about 34 alanine codons of the codon-optimized nucleic acid sequence are GCT;

wherein about 20 tyrosine codons of the codon-optimized nucleic acid sequence are TAT;

wherein about 1 of the 5 histidine codons of the codon-optimized nucleic acid sequence are CAT;

wherein about 20 glutamine codons of the codon-optimized nucleic acid sequence are CAA;

wherein about 30 asparagine codons of the codon-optimized nucleic acid sequence are AAT;

wherein about 13 lysine codons of the codon-optimized nucleic acid sequence are AAA;

wherein about 15 of the 41 aspartic acid codons of the codon-optimized nucleic acid sequence are GAT;

wherein about 12 glutamic acid codons of the codon-optimized nucleic acid sequence are GAA;

wherein about 18 cysteine codons of the codon-optimized nucleic acid sequence are TGT;

wherein about 8 tryptophan codons of the codon-optimized nucleic acid sequence are TGG;

wherein about 10 arginine codons of the codon-optimized nucleic acid sequence are CGT; and
wherein about 45 glycine codons of the codon-optimized nucleic acid sequence are GGT; and
(b) wherein the codon adaptation index (CAI) of the codon-optimized nucleic acid sequence is about 0.8 to about 1.0.

2. The polynucleotide of claim 1, wherein the amino acid sequence of the cellobiohydrolase polypeptide is at least 95% sequence identical to the amino acid sequence of SEQ ID NO: 13.

3. The polynucleotide of claim 1, wherein
at least 4, 5, 6, 7, 8, 9, or 10 contiguous A or T nucleic acid residues of the codon-optimized nucleic acid sequence are further replaced with different residues such that the resulting codons are codons with the second highest frequency for that amino acid in *Saccharomyces cerevisiae*.

4. The polynucleotide of claim 1, wherein the codon-optimized nucleic acid sequence is further codon-optimized by replacing nucleotides to eliminate one or more restriction sites within the sequence, wherein the resulting codons are codons with the second highest frequency for the corresponding amino acids in *Saccharomyces cerevisiae*.

5. The polynucleotide of claim 4, wherein the one or more restriction enzyme sites are selected from the group consisting of PacI, AscI, BamHI, BglII, EcoRI and XhoI.

6. The polynucleotide of claim 1, wherein the codon-optimized nucleic acid sequence is further codon-optimized by replacing one or more direct repeats, inverted repeats and mirror repeats with lengths of 10 bases or longer within the sequence with different residues such that the resulting codons are codons with the second highest frequency for the corresponding amino acid in *Saccharomyces cerevisiae*.

7. The polynucleotide of claim 1, wherein the codon-optimized nucleic acid sequence encodes amino acids 7-455 of SEQ ID NO: 13.

8. The polynucleotide of claim 7, wherein the codon-optimized nucleic acid sequence comprises nucleotides 19 to 1379 of SEQ ID NO: 9.

9. The polynucleotide of claim 1, wherein the codon-optimized nucleic acid sequence encodes amino acids 1-455 of SEQ ID NO: 13.

10. The polynucleotide of claim 9, wherein the codon-optimized nucleic acid sequence comprises nucleotides 1 to 1379 of SEQ ID NO: 9.

11. The polynucleotide of claim 1, wherein the polynucleotide is operably linked with a nucleic acid that encodes a secretion signal peptide.

12. The polynucleotide of claim 11, wherein the secretion signal peptide comprises amino acids 1-18 of SEQ ID NO: 13.

13. The polynucleotide of claim 11, wherein the secretion signal peptide comprises a *T. reesei* xyn2 secretion signal.

14. The polynucleotide of claim 13, wherein the *T. reesei* xyn2 secretion signal is the xyn2 secretion signal of SEQ ID NO: 19.

15. The polynucleotide of claim 1, wherein the codon-optimized nucleic acid sequence is operably linked with a heterologous nucleic acid sequence.

16. The polynucleotide of claim 15, wherein the heterologous nucleic acid sequence and the codon-optimized nucleic acid sequence encode a fusion protein, wherein said fusion protein comprises a heterologous polypeptide encoded by the heterologous nucleic acid sequence and the cellobiohydrolase polypeptide encoded by the codon-optimized nucleic acid sequence.

17. The polynucleotide of claim 16, wherein the heterologous polypeptide and the polypeptide are fused together via a linker.

18. The polynucleotide of claim 16, wherein the heterologous polypeptide is encoded by a nucleic acid sequence selected from the group consisting of SEQ ID NOs: 1-6.

19. The polynucleotide of claim 16, wherein the heterologous polypeptide is encoded by a nucleic acid sequence selected from the group consisting of SEQ ID NOs: 7-10.

20. A polynucleotide encoding a cellobiohydrolase polypeptide, wherein said polypeptide has a functional cellobiohydrolase activity, wherein said polynucleotide comprises a codon-optimized nucleic acid sequence at least 90% sequence identical to the nucleic acid sequence of SEQ ID NO: 9; wherein the codon-optimized nucleic acid sequence encodes the amino acid sequence of SEQ ID NO: 13;
wherein about 4 of the 16 phenylalanine codons of the codon-optimized nucleic acid sequence are TTT and about 3 of the phenylalanine codons are TTC;
wherein about 7 of the 26 leucine codons of the codon-optimized nucleic acid sequence are TTA, about 7 of the leucine codons are TTG, about 3 of the leucine codons are CTT, about 1 of the leucine codons are CTC, about 4 of the leucine codons are CTA, and about 3 of the leucine codons are CTG;
wherein about 5 of the 15 isoleucine codons of the codon-optimized nucleic acid sequence are ATT, about 3 of the isoleucine codons are ATC, and about 3 of the isoleucine codons are ATA;
wherein about 2 of the 10 methionine codons of the codon-optimized nucleic acid sequence are ATG;
wherein about 5 of the 24 valine codons of the codon-optimized nucleic acid sequence are GTT, about 3 of the valine codons are GTG, about 3 of the valine codons are GTA, and about 2 of the valine codons are GTC;
wherein about 9 of the 39 serine codons of the codon-optimized nucleic acid sequence are TCT, about 6 of the serine codons are TCC, about 7 of the serine codons are TCA, about 3 of the serine codons are TCG, about 6 of the serine codons are AGT, and about 4 of the serine codons are AGC;
wherein about 4 of the 25 proline codons of the codon-optimized nucleic acid sequence are CCT, about 2 of the proline codons are CCC, about 5 of the proline codons are CCA, and about 1 of the proline codons are CCG;
wherein about 9 of the 44 threonine codons of the codon-optimized nucleic acid sequence are ACT, about 6 of the threonine codons are ACC, about 8 of the threonine codons are ACA, and about 4 of the threonine codons are ACG;
wherein about 7 of the 34 alanine codons of the codon-optimized nucleic acid sequence are GCT, about 4 of the alanine codons are GCC, about 6 of the alanine codons are GCA, and about 2 of the alanine codons are GCG;
wherein about 4 of the 20 tyrosine codons of the codon-optimized nucleic acid sequence are TAT and about 3 of the tyrosine codons are TAC;
wherein about 1 of the 5 histidine codons of the codon-optimized nucleic acid sequence are CAT;
wherein about 6 of the 20 glutamine codons of the codon-optimized nucleic acid sequence are CAA and about 2 of the glutamine codons are CAG;
wherein about 11 of the 30 asparagine codons of the codon-optimized nucleic acid sequence are AAT and about 7 of the asparagine codons are AAC;

wherein about 5 of the 13 lysine codons of the codon-optimized nucleic acid sequence are AAA and about 4 of the lysine codons are AAG;

wherein about 15 of the 41 aspartic acid codons of the codon-optimized nucleic acid sequence are GAT and about 8 of the aspartic acid codons are GAC;

wherein about 6 of the 12 glutamic acid codons of the codon-optimized nucleic acid sequence are GAA and about 2 of the glutamic acid codons are GAG;

wherein about 2 of the 18 cysteine codons of the codon-optimized nucleic acid sequence are TGT and about 1 of the cysteine codons are TGC;

wherein about 1 of the 8 tryptophan codons of the codon-optimized nucleic acid sequence are TGG;

wherein about 1 of the 10 arginine codons of the codon-optimized nucleic acid sequence are CGT, about 2 of the arginine codons are AGA, and about 1 of the arginine codons are AGG; and wherein about 11 of the 45 glycine codons of the codon-optimized nucleic acid sequence are GGT, about 4 of the glycine codons are GGC, about 5 of the glycine codons are GGA, and about 3 of the glycine codons are GGG.

21. The polynucleotide of claim 20, wherein the codon-optimized nucleic acid sequence is at least 95% sequence identical to the nucleic acid sequence of SEQ ID NO: 9.

22. The polynucleotide of claim 20, wherein
at least 4, 5, 6, 7, 8, 9, or 10 contiguous A or T nucleic acid residues of the codon-optimized nucleic acid sequence are further replaced with different residues such that the resulting codons are codons with the second highest frequency for that amino acid in *Saccharomyces cerevisiae*.

23. The polynucleotide of claim 20, wherein the codon optimized nucleic acid sequence is further codon-optimized by replacing nucleotides to eliminate one or more restriction sites within the sequence, wherein the resulting codons are codons with the second highest frequency for the corresponding amino acids in *Saccharomyces cerevisiae*.

24. The polynucleotide of claim 23, wherein the one or more restriction enzyme sites are selected from the group consisting of PacI, AscI, BamHI, BglII, EcoRI and XhoI.

25. The polynucleotide of claim 20, wherein the codon-optimized nucleic acid sequence is further codon-optimized by replacing one or more direct repeats, inverted repeats and mirror repeats with lengths of 10 bases or longer within the sequence with different residues such that the resulting codons are codons with the second highest frequency for the corresponding amino acids in *Saccharomyces cerevisiae*.

26. The polynucleotide of claim 20, wherein the codon-optimized nucleic acid sequence encodes amino acids 7-455 of SEQ ID NO: 13.

27. The polynucleotide of claim 26, wherein the codon-optimized nucleic acid sequence comprises nucleotides 19 to 1379 of SEQ ID NO: 9.

28. The polynucleotide of claim 20, wherein the codon-optimized nucleic acid sequence encodes amino acids 1-455 of SEQ ID NO: 13.

29. The polynucleotide of claim 28, wherein the codon-optimized nucleic acid sequence comprises nucleotides 1 to 1379 of SEQ ID NO: 9.

30. The polynucleotide of claim 20, wherein the polynucleotide is operably linked with a nucleic acid that encodes a secretory signal peptide.

31. The polynucleotide of claim 30, wherein the secretion signal peptide comprises amino acids 1-18 of SEQ ID NO: 13.

32. The polynucleotide of claim 30, wherein the secretion signal peptide comprises a *T. reesei* xyn2 secretion signal.

33. The polynucleotide of claim 20, wherein the codon-optimized nucleic acid sequence is operably linked with a heterologous nucleic acid sequence.

34. The polynucleotide of claim 33, wherein the heterologous nucleic acid sequence and the codon-optimized nucleic acid sequence encode a fusion protein, wherein said fusion protein comprises a heterologous polypeptide encoded by the heterologous nucleic acid sequence and the cellobiohydrolase polypeptide encoded by the codon-optimized nucleic acid sequence.

35. The polynucleotide of claim 34, wherein the heterologous polypeptide and the polypeptide are fused together via a linker.

36. The polynucleotide of claim 34, wherein the heterologous polypeptide is encoded by a nucleic acid sequence selected from the group consisting of SEQ ID NOs: 1-6.

37. The polynucleotide of claim 34, wherein the heterologous polypeptide is encoded by a nucleic acid sequence selected from the group consisting of SEQ ID NOs: 7-10.

38. A vector encoding a cellobiohydrolase polypeptide which comprises an amino acid sequence at least 90% identical to the amino acid sequence of SEQ ID NO: 13, wherein said polypeptide has functional cellobiohydrolase activity, wherein said vector comprises a first polynucleotide having a codon-optimized nucleic acid sequence which encodes the cellobiohydrolase polypeptide;

(a) wherein about 16 phenylalanine codons of the codon-optimized nucleic acid sequence are TTT;

wherein about 26 leucine codons of the codon-optimized nucleic acid sequence are TTA;

wherein about 15 isoleucine codons of the codon-optimized nucleic acid sequence are ATT;

wherein about 10 methionine codons of the codon-optimized nucleic acid sequence are ATG;

wherein about 24 valine codons of the codon-optimized nucleic acid sequence are GTT;

wherein about 39 serine codons of the codon-optimized nucleic acid sequence are TCT;

wherein about 25 proline codons of the codon-optimized nucleic acid sequence are CCT;

wherein about 44 threonine codons of the codon-optimized nucleic acid sequence are ACT;

wherein about 34 alanine codons of the codon-optimized nucleic acid sequence are GCT;

wherein about 20 tyrosine codons of the codon-optimized nucleic acid sequence are TAT;

wherein about 1 of the 5 histidine codons of the codon-optimized nucleic acid sequence are CAT;

wherein about 20 glutamine codons of the codon-optimized nucleic acid sequence are CAA;

wherein about 30 asparagine codons of the codon-optimized nucleic acid sequence are AAT;

wherein about 13 lysine codons of the codon-optimized nucleic acid sequence are AAA;

wherein about 15 of the 41 aspartic acid codons of the codon-optimized nucleic acid sequence are GAT;

wherein about 12 glutamic acid codons of the codon-optimized nucleic acid sequence are GAA;

wherein about 18 cysteine codons of the codon-optimized nucleic acid sequence are TGT;

wherein about 8 tryptophan codons of the codon-optimized nucleic acid sequence are TGG;

wherein about 10 arginine codons of the codon-optimized nucleic acid sequence are CGT; and wherein about 45 glycine codons of the codon-optimized nucleic acid sequence are GGT; and (b) wherein the codon adaptation index (CAI) of the codon-optimized nucleic acid sequence is about 0.8 to about 1.0.

39. The vector of claim 38, wherein the first polynucleotide is the polynucleotide of SEQ ID NO: 9.

40. The vector of claim 38, further comprising a second polynucleotide.

41. The vector of claim 40, wherein the second polynucleotide is selected from the group consisting of the polynucleotides of SEQ ID NOs: 1-6.

42. The vector of claim 40, wherein the second polynucleotide is selected from the group consisting of the polynucleotides of SEQ ID NOs: 7-10 and 15-16.

43. The vector of claim 40, wherein the second polynucleotide encodes a functional cellobiohydrolase 1 (Cbh1) domain or a structural variant of a Cbh1 domain.

44. The vector of claim 40, wherein the first polynucleotide and the second polynucleotide are operably linked by a linker.

45. The vector of claim 40, wherein the second polynucleotide is either in the forward or in the reverse orientation to the first polynucleotide.

46. The vector of claim 38, which is a plasmid.

47. The vector of claim 46, which is a yeast episomal plasmid.

48. The vector of claim 47, which is a yeast integrating plasmid.

49. A host cell comprising the polynucleotide of claim 1.

50. The host cell of claim 49, wherein the host cell is a yeast host cell.

51. The host cell of claim 50, wherein the yeast organism is selected from the group consisting of Saccharomyces cervisiae, Kluveromyces lactus, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus and Schwanniomyces occidentalis.

52. The host cell of claim 49, wherein the host cell is a thermophilic or mesophilic bacterial organism.

53. The host cell of claim 49 wherein the host cell expresses one or more polypeptides having cellobiohydrolase activity.

54. The host cell of claim 51, wherein the yeast is Saccharomyces cerevisiae.

55. The host cell of claim 49, further comprising one or more heterologously expressed endoglucanase polypeptides.

56. The host cell of claim 49, further comprising one or more heterologously expressed β-glucosidase polypeptides.

57. The host cell of claim 49, further comprising one or more heterologously expressed exoglucanase polypeptides.

58. The host cell of claim 49, further comprising at least one or more heterologously expressed endoglucanase polypeptides and/or at least one or more heterologously expressed β-glucosidase polypeptides and/or at least one or more heterologously expressed exoglucanase polypeptides.

59. The host cell of claim 55, wherein the endoglucanase polypeptide is a T. reesei Eg1.

60. The host cell of claim 56, wherein the β-glucosidase polypeptide is S. fibuligera Bgl1.

61. The host cell of claim 59, wherein a gene encoding the T. reesei Eg1 has been integrated into the yeast genome.

62. A host cell comprising the vector of claim 38.

63. The host cell of claim 60, wherein a gene encoding the S. fibuligera Bgl1 has been integrated into the yeast genome.

* * * * *

SEQUENCE LISTING

```
<160> NUMBER OF SEQ ID NOS: 20

<210> SEQ ID NO 1
<211> LENGTH: 1704
<212> TYPE: DNA
<213> ORGANISM: Talaromyces emersonii

<400> SEQUENCE: 1
ctcagactca aacactccat cagcagcttc gaaagcggtc tttttgctat catcatgctt      60
cgacgggctc ttcttctatc ctcttccgcc atccttgctg tcaaggcaca gcaggccggc     120
acggcgacgg cagagaacca cccgcccctg acatggcagg aatgcaccgc ccctgggagc     180
tgcaccaccc agaacggggc ggtcgttctt gatgcgaact ggcgttgggt gcacgatgtg     240
aacggataca ccaactgcta cacgggcaat acctgggacc ccacgtactg ccctgacgac     300
gaaacctgcg cccagaactg tgcgctggac ggcgcggatt acgagggcac ctacggcgtg     360
acttcgtcgg gcagctcctt gaaactcaat ttcgtcaccg ggtcgaacgt cggatcccgt     420
ctctacctgc tgcaggacga ctcgacctat cagatcttca gcttctgaa ccgcgagttc     480 agctttgacg tcgatgtctc caatcttccg tgcggattga acggcgctct gtactttgtc     540
gccatggacg ccgacggcgg cgtgtccaag tacccgaaca acaaggctgg tgccaagtac     600
ggaaccgggt attgcgactc ccaatgccca cgggacctca gttcatcga cggcgaggcc     660 aacgtcgagg gctggcagcc gtcttcgaac aacgccaaca ccggaattgg cgaccacggc     720
tcctgctgtg cggagatgga tgtctgggaa gcaaacagca tctccaatgc ggtcactccg     780
```

```
caccegtgcg acacgccagg ccagacgatg tgctctggag atgactgcgg tggcacatac      840
tctaacgatc gctacgcggg aacctgcgat cctgacggct gtgacttcaa cccttaccgc      900
atgggcaaca cttctttcta cgggcctggc aagatcatcg ataccaccaa gcccttcact      960
gtcgtgacgc agttcctcac tgatgatggt acggatactg gaactctcag cgagatcaag     1020
cgcttctaca tccagaacag caacgtcatt ccgcagccca actcggacat cagtggcgtg     1080
accggcaact cgatcacgac ggagttctgc actgctcaga agcaggcctt tggcgacacg     1140
gacgacttct ctcagcacgg tggcctggcc aagatgggag cggccatgca gcagggtatg     1200
gtcctggtga tgagtttgtg ggacgactac gccgcgcaga tgctgtggtt ggattccgac     1260
tacccgacgg atgcggaccc cacgacccct ggtattgccc gtggaacgtg tccgacggac     1320
tcgggcgtcc catcggatgt cgagtcgcag agccccaact cctacgtgac ctactcgaac     1380
attaagtttg gtccgatcaa ctcgaccttc accgcttcgt gagtcttggt tacatttgaa     1440
gtagacggaa gtagctctgc gatggaactg gcatatggag aagaccacac aaaactgcat     1500
cgaagaaaag agggggaaa agagaaaagc aaagttattt agtttgaaaa tgaaactacg     1560
ctcgttttta ttcttgaaaa tcgccactct tgcctttttt ttcttttttc tttttatttt     1620
ttttcctttt gaaatcttca atttaaatgt acatattgtt aaatcaaatc aagtaaatat     1680
acttgaaaaa aaaaaaaaaa aaaa                                            1704

<210> SEQ ID NO 2
<211> LENGTH: 2046
<212> TYPE: DNA
<213> ORGANISM: Humicola grisea

<400> SEQUENCE: 2
gccgtgacct tgcgcgcttt gggtggcggt ggcgagtcgt ggacggtgct tgctggtcgc       60
cggccttccc ggcgatccgc gtgatgagag ggccaccaac ggcgggatga tgctccatgg      120
ggaacttccc catggagaag agagagaaac ttgcggagcc gtgatctggg gaaagatgct      180
ccgtgtctcg tctatataac tcgagtctcc ccgagccctc aacaccacca gctctgatct      240
caccatcccc atcgacaatc acgcaaacac agcagttgtc gggccattcc ttcagacaca      300
tcagtcaccc tccttcaaaa tgcgtaccgc caagttcgcc accctcgccg cccttgtggc      360
ctcggccgcc gcccagcagg cgtgcagtct caccaccgag aggcaccctt ccctctcttg      420
gaacaagtgc accgccggcg gccagtgcca gaccgtccag gcttccatca ctctcgactc      480
caactggcgc tggactcacc aggtgtctgg ctccaccaac tgctacacgg caacaagtg      540
ggatactagc atctgcactg atgccaagtc gtgcgctcag aactgctgcg tcgatggtgc      600
cgactacacc agcacctatg gcatcaccac caacggtgat ccctgagcc tcaagttcgt      660
caccaagggc cagcactcga ccaacgtcgg ctcgcgtacc tacctgatgg acggcgagga      720
caagtatcag agtacgttct atcttcagcc ttctcgcgcc ttgaatcctg gctaacgttt      780
acacttcaca gccttcgagc tcctcggcaa cgagttcacc ttcgatgtcg atgtctccaa      840
catcggctgc ggtctcaacg gcgccctgta cttcgtctcc atggacgccg atggtggtct      900
cagccgctat cctggcaaca aggctggtgc caagtacggt accggctact gcgatgctca      960
gtgccccgt gacatcaagt tcatcaacgg cgaggccaac attgagggct ggaccggctc     1020
caccaacgac cccaacgccg cgcgggccg ctatggtacc tgctgctctg agatggatat     1080
ctgggaagcc aacaacatgg ctactgcctt cactcctcac ccttgcacca tcattggcca     1140
```

-continued

```
gagccgctgc gagggcgact cgtgcggtgg cacctacagc aacgagcgct acgccggcgt    1200
ctgcgacccc gatggctgcg acttcaactc gtaccgccag ggcaacaaga ccttctacgg    1260
caagggcatg accgtcgaca ccaccaagaa gatcactgtc gtcacccagt cctcaagga    1320
tgccaacggc gatctcggcg agatcaagcg cttctacgtc caggatggca agatcatccc    1380
caactccgag tccaccatcc ccggcgtcga gggcaattcc atcacccagg actggtgcga    1440
ccgccagaag gttgcctttg cgacattga cgacttcaac cgcaagggcg gcatgaagca    1500
gatgggcaag gccctcgccg gccccatggt cctggtcatg tccatctggg atgaccacgc    1560
ctccaacatg ctctggctcg actcgacctt ccctgtcgat gccgctggca gcccggcgc    1620
cgagcgcggt gcctgcccga ccacctcggg tgtccctgct gaggttgagg ccgaggcccc    1680
caacagcaac gtcgtcttct ccaacatccg cttcggcccc atcggctcga ccgttgctgg    1740
tctccccggc gcgggcaacg gcggcaacaa cggcggcaac ccccgcccc ccaccaccac    1800
cacctcctcg gctccggcca ccaccaccac cgccagcgct ggccccaagg ctggccgctg    1860
gcagcagtgc ggcggcatcg gcttcactgg cccgaccccag tgcgaggagc cctacatttg    1920
caccaagctc aacgactggt actctcagtg cctgtaaatt ctgagtcgct gactcgacga    1980
tcacggccgg ttttttgcatg aaaggaaaca acgaccgcg ataaaaatgg agggtaatga    2040
gatgtc                                                               2046
```

<210> SEQ ID NO 3
<211> LENGTH: 3459
<212> TYPE: DNA
<213> ORGANISM: Thermoascus aurantiacus

<400> SEQUENCE: 3

```
gaattctaga cctttatcct ttcatccgac cagacttccc ttttgacct tggcgccctg      60
ttgactacct acctacctag gtagtaacgt cgtcgaccct cttgaatgat ccttgtcaca    120
ctgcaaacat ccgaaaacat acggcaaaag atgattgggc atggatgcag agacatcga    180
atgagggctt agaaggaaat gaaaacctgg gaccaggacg ctaggtacga tgaaatccgc    240
caatggtgaa actttaagtc gtgcctacag cacaggctct gtgaagattg cgctgttcag    300
acttaatctt ctcatcacag tccaagtctt tatgaaaagg aaaagagag ggaagagcgc     360
tatttcgagc tgttggcctc atagggagac agtcgagcat accagcggta tcgacgttag    420
actcaaccaa gaataatgac gagaataaac acagaagtca accttgaact ggatagcagg    480
gttccagcag cagatagtta cttgcataaa gacaactccc cgagggctct ctgcatacac    540
caggatgttc cggaattatt cactgctcgt ttccgacgtg gcgtcagtga tccgtctcca    600
cagaactcta cctgggaata cccaggggga ggaatctgca agtaagaact taataccaat    660
ccccgggggct gccgaggtga atcgaatctc ccgcgggaaa ttaaacccat acgatgtttt    720
tgcaccacat gcatgcttag cacgatttct ccgcaaggga gtcacagaga aagacatatt    780
tcgcatacta ctgtgactct gcagagttac atatcactca ggatacattg cagatcattg    840
tccgggcatc aaaaatggac ctgcaggatc aacggcccga caaaacacaa gtggctaaag    900
ctgggggatg cccgaaaccc tctggtgcaa tatcatttga tggatgttcc ccccgcattt    960
ctaagacatc gacggatcgg cccgcatact aatccttta tcaaccaaaa gttccactcg    1020
actagagaaa aaaaggcca aggcactag ttgcagtcgg atactggtct tttcgccgtc    1080
caacaccttc atccatgatc cccttagcca ccaatgcccc acataataca tgttgacata    1140
ggtacgtagc tctgttatcc aatcggatcc gaacctcttt aacggacccc tcctacacac    1200
```

```
cttatcctaa cttcagaaga ctgttgccca ttggggattg aggaggtccg ggtcgcagga    1260
tgcgttctag gctaaattct cggccggtag ccatctcgaa tctctcgtga agccttcatc    1320
tgaacggttg gcggcccgtc aagccgatga ccatgggttc ctgatagagc ttgtgcctga    1380
ccggccttgg cggcatagac gagctgaaca catcaggtat gaacagatca gatataaagt    1440
cggattgagt cctagtacga agcaatccgc caccaccaaa tcaagcaacg agcgacacga    1500
ataacaatat caatcgaatc gcaatgtatc agcgcgctct tctcttctct ttcttcctcg    1560
ccgccgcccg cgcgcacgag gccggtaccg taaccgcaga gaatcaccct tccctgacct    1620
ggcagcaatg ctccagcggc ggtagttgta ccacgcagaa tggaaaagtc gttatcgatg    1680
cgaactggcg ttgggtccat accacctctg atacaccaa ctgctacacg gcaatacgt     1740 gggacaccag tatctgtccc gacgacgtga cctgcgctca gaattgtgcc ttggatggag    1800
cggattacag tggcacctat ggtgttacga ccagtggcaa cgccctgaga ctgaactttg    1860
tcacccaaag ctcagggaag aacattggct cgcgcctgta cctgctgcag gacgacacca    1920
cttatcagat cttcaagctg ctgggtcagg agtttacctt cgatgtcgac gtctccaatc    1980
tcccttgcgg gctgaacggc gccctctact ttgtggccat ggacgccgac ggcaatttgt    2040
ccaaataccc tggcaacaag gcaggcgcta agtatggcac tggttactgc gactctcagt    2100
gccctcggga tctcaagttc atcaacggtc aggtacgtca gaagtgataa ctagccagca    2160
gagcccatga atcattaact aacgctgtca aatacaggcc aacgttgaag gctggcagcc    2220
gtctgccaac gacccaaatg ccggcgttgg taaccacggt tcctcgtgcg ctgagatgga    2280
tgtctgggaa gccaacagca tctctactgc ggtgacgcct cacccatgcg acaccccgg    2340 ccagaccatg tgccagggag acgactgtgg tggaacctac tcctccactc gatatgctgg    2400
tacctgcgac cctgatggct gcgacttcaa tccttaccag ccaggcaacc actcgttcta    2460
cggcccgggg aagatcgtcg acactagctc caaattcacc gtcgtcaccc agttcatcac    2520
cgacgacggg acaccctccg gcaccctgac ggagatcaaa cgcttctacg tccagaacgg    2580
caaggtgatc ccccagtcgg agtcgacgat cagcggcgtc accggcaact caatcaccac    2640
cgagtattgc acggcccaga aggcagcctt cggcgacaac accggcttct tcacgcacgg    2700
cgggcttcag aagatcagtc aggctctggc tcagggcatg gtcctcgtca tgagcctgtg    2760
ggacgatcac gccgccaaca tgctctggct ggacagcacc tacccgactg atgcggaccc    2820
ggacacccct ggcgtcgcgc gcggtacctg ccccacgacc tccggcgtcc cggccgacgt    2880
tgagtcgcag aaccccaatt catatgttat ctactccaac atcaaggtcg acccatcaa    2940 ctcgaccttc accgccaact aagtaagtaa cgggcactct accaccgaga gcttcgtgaa    3000
gatacagggg tagttgggag attgtcgtgt acagggggaca tgcgatgctc aaaaatctac    3060
atcagtttgc caattgaacc atgaagaaaa gggggagatc aaagaagtct gtcagaagag    3120
aggggctgtg gcagcttaag ccttgttgta gatcgttcag agaaaaaaaa agtttgcgta    3180
cttattatat taggtcgatc attatccgat tgactccgtg acaagaatta aaaagagtac    3240
tgcttgcttg cctatttaaa ttgttatata cgccgtagcg cttgcggacc accctcaca    3300 gtatatcggt tcgcctcttc ttgtctcttc atctcacatc acaggtccag gtccagcccg    3360
gcccggtccg ggtgccatgc atgcacaggg ggactaatat attaatcgtg accctgtvcc    3420
taagctaggg tccctgcatt ttgaacctgt ggacgtctg                           3459
```

<210> SEQ ID NO 4

<211> LENGTH: 2220
<212> TYPE: DNA
<213> ORGANISM: Trichoderma reesei

<400> SEQUENCE: 4

```
aaggttagcc aagaacaata gccgataaag atagcctcat taaacggaat gagctagtag      60
gcaaagtcag cgaatgtgta tatataaagg ttcgaggtcc gtgcctccct catgctctcc     120
ccatctactc atcaactcag atcctccagg agacttgtac accatctttt gaggcacaga     180
aacccaatag tcaaccgcgg actggcatca tgtatcggaa gttggccgtc atcacggcct     240
tcttggccac agctcgtgct cagtcggcct gcactctcca atcggagact cacccgcctc     300
tgacatggca gaaatgctcg tctggtggca cttgcactca acagacaggc tccgtggtca     360
tcgacgccaa ctggcgctgg actcacgcta cgaacagcag cacgaactgc tacgatggca     420
acacttggag ctcgacccta tgtcctgaca acgagacctg cgcgaagaac tgctgtctgg     480
acggtgccgc ctacgcgtcc acgtacggag ttaccacgag cggtaacagc ctctccattg     540
gctttgtcac ccagtctgcg cagaagaacg ttggcgctcg cctttacctt atggcgagcg     600
acacgaccta ccaggaattc accctgcttg gcaacgagtt ctctttcgat gttgatgttt     660
cgcagctgcc gtaagtgact taccatgaac ccctgacgta tcttcttgtg ggctcccagc     720
tgactggcca atttaaggtg cggcttgaac ggagctctct acttcgtgtc catggacgcg     780
gatggtggcg tgagcaagta tcccaccaac aacgctggcg ccaagtacgg cacggggtac     840
tgtgacagcc agtgtccccg cgatctgaag ttcatcaatg ccaggccaa cgttgagggc     900
tgggagccgt catccaacaa cgcaaacacg ggcattggag acacggaag ctgctgctct     960
gagatggata tctgggaggc caactccatc tccgaggctc ttaccccca cccttgcacg    1020
actgtcggcc aggagatctg cgagggtgat gggtgcggcg gaacttactc cgataacaga    1080
tatggcggca cttgcgatcc cgatggctgc gactggaacc cataccgcct gggcaacacc    1140
agcttctacg gccctggctc aagctttacc ctcgatacca ccaagaaatt gaccgttgtc    1200
acccagttcg agacgtcggg tgccatcaac cgatactatg tccagaatgg cgtcactttc    1260
cagcagccca cgccgagct tggtagttac tctggcaacg agctcaacga tgattactgc    1320
acagctgagg agacagaatt cggcggatct cttttctcaga caagggcggc ctgactcagt    1380
tcaagaaggc tacctctggc ggcatggttc tggtcatgag tctgtgggat gatgtgagtt    1440
tgatggacaa acatgcgcgt tgacaaagag tcaagcagct gactgagatg ttacagtact    1500
acgccaacat gctgtggctg gactccacct acccgacaaa cgagacctcc tccacacccg    1560
gtgccgtgcg cggaagctgc tccaccagct ccggtgtccc tgctcaggtc gaatctcagt    1620
ctcccaacgc caaggtcacc ttctccaaca tcaagttcgg acccattggc agcaccggca    1680
accctagcgg cggcaaccct cccggcggaa accgtggcac caccaccacc cgccgcccag    1740
ccactaccac tggaagctct cccggaccta cccagtctca ctacggccag tgcggcggta    1800
ttggctacag cggccccacg gtctgcgcca gcggcacaac ttgccaggtc ctgaaccctt    1860
actactctca gtgcctgtaa agctccgtgc gaaagcctga cgcaccggta gattcttggt    1920
gagcccgtat catgacggcg gcgggagcta catggcccg ggtgatttat tttttttgta    1980
tctacttctg acccttttca aatatacggt caactcatct ttcactggag atgcggcctg    2040
cttggtattg cgatgttgtc agcttggcaa attgtggctt tcgaaaacac aaaacgattc    2100
cttagtagcc atgcatttta agataacgga atagaagaaa gaggaaatta aaaaaaaaa    2160
aaaaacaaac atcccgttca taacccgtag aatcgccgct cttcgtgtat cccagtacca    2220
```

<210> SEQ ID NO 5
<211> LENGTH: 2369
<212> TYPE: DNA
<213> ORGANISM: Talaromyces emersonii
<220> FEATURE:
<221> NAME/KEY: misc_feature
<222> LOCATION: (298)..(298)
<223> OTHER INFORMATION: n is a, c, g, or t

<400> SEQUENCE: 5

```
gacggacctg cacttagtcg gtaggttatg tatgtagctg gagattggga tagggaagtt      60
agctaatagt ctacttcgtg tgagggttga ttttgatggt cgacagtatt cgtttcttat     120
acgcagcgtc atggatctgt gtttctgtca catgtcgggt ggatggttcc tggacagcag     180
cacacaaatg gtgttctgta gataggcgat actcggcagg ggattgtgca ggggattgta     240
tcgtagatgg ttctagtaaa atagatcccg agtatggtta gctctcatac ctcgagtnga     300
tgaagcacaa tatgctacga tatgccaagt aaaactctat tgtattctgc agctagcaat     360
tgaagaatcc gacattccca ttgtcatcta atcgggcaga catgtgcaaa gagggacgat     420
tcgtgatcga agtgctccaa tccatggcgt aggaccagac agctccatcc gatctagagc     480
tatatggagc tcctcgcaac tccgacactc cgcgagacag ctctcacaag cactataaat     540
atggccaaga accctgcaga acagcttcac tctacagccc gttgagcaga caaacaaaa      600
tatcactcca gagagaaagc aacatgcgga atcttcttgc tcttgcaccg ccgcgctgc      660
ttgtcggcgc agcggaagcg caacaatccc tctggggaca atgtgagcag ctcctaaacg     720
tctgtctgag ggattatgtc tgactgctca ggcggcggga gttcgtggac tggcgcgacg     780
agctgtgctg ctggagcgac gtgcagcaca atcaatcctt gtacgtctgc tgaacgataa     840
tcctacattg ttgacgtgct aactgcgtag actacgcaca atgcgttcct gcaacggcca     900
ctccgaccac gctgacgaca acgacaaaac caacgtccac cggcggcgct gctccaacga     960
ctcctcctcc gacaacgact ggaacaacga catcgcccgt cgtcaccagg cccgcgtctg    1020
cctccggcaa cccgttcgaa ggctaccagc tctacgccaa tccgtactat gcgtcggagg    1080
tgattagttt ggcaattccc tcgctgagca gcgagctggt tccaaggcg  agcgaggtgg    1140
ccaaggtgcc gtctttcgtc tggctgtaag taaattcccc caggctgtca tttccccta     1200
ctgatcttgt ccagcgacca agccgccaag gtgcccagca tgggcgacta tctgaaagac    1260
atccagtcgc agaacgcagc cggcgcagac cccccgattg caggcatctt tgtcgtctac    1320
gacctgcctg accgcgactg cgcggctgca gccagcaatg gcgagttctc catcgccaac    1380
aacggcgtcg ccctgtacaa gcagtacatc gactcgatcc gcgagcagct gacgacctat    1440
tcagatgtgc acaccatcct ggtcatcggt agttccagtc ctcttctgtg atgttgatga    1500
aaaaaatact gactgactcc tgcagaaccc gacagccttg cgaacgtggt caccaacctg    1560
aacgtgccga atgcgcaaa  tgcccaggac gcctatctcg aatgcatcaa ctacgccatc    1620
acccagctcg atctgccaaa cgtggccatg tatcttgatg ctggtgagtc ctcacataca    1680
agtgaataaa aataaaactg atgcagtgca ggacacgccg gatggctagg ctggcaagcc    1740
aacctcgccc ccgccgccca gctgtttgcc tcggtgtaca aaaacgcctc ctctccggca    1800
tccgtccgcg gtctcgccac caacgtcgcc aactacaacg cctggtcgat cagccggtgc    1860
ccgtcgtaca cgcagggcga cgccaattgc gacgaggagg attacgtgaa tgccttgggg    1920
ccgttgttcc aggaacaggg attcccggca tattttatca ttgatacatg taagctttac    1980
```

```
cccagaaccc ctccatagaa ggtcaatcta acggtaatgt acagcccgca atggcgtccg   2040
acccaccaag caaagccaat ggggcgactg gtgcaacgtc atcggcacgg gcttcggcgt   2100
ccggcccacg accgacaccg gcaatcctct cgaggacgct ttcgtctggg tcaagcccgg   2160
tggcgagagc gatggcacgt ccaacacgac ctctccgcgg tacgactacc actgcgggct   2220
gagcgatgcg ctgcagccgg cgccggaggc ggggacttgg ttccaggtat gacgcgcctt   2280
cgtattagca attacgatac atgtgcatgc tgaccatgcg acaggcgtac tttgagcagt   2340
tgctcacgaa tgctaacccg ctgttctga                                     2369
```

<210> SEQ ID NO 6
<211> LENGTH: 2193
<212> TYPE: DNA
<213> ORGANISM: Trichoderma reesei

<400> SEQUENCE: 6

```
tcgaactgac aagttgttat attgcctgtg taccaagcgc gaatgtggac aggattaatg     60
ccagagttca ttagcctcaa gtagagccta tttcctcgcc ggaaagtcat ctctcttatt    120
gcatttctgc ccttcccact aactcagggt gcagcgcaac actacacgca acatatacac    180
tttattagcc gtgcaacaag gctattctac gaaaaatgct acactccaca tgttaaaggc    240
gcattcaacc agcttcttta ttgggtaata tacagccagg cggggatgaa gctcattagc    300
cgccactcaa ggctatacaa tgttgccaac tctccgggct ttatcctgtg ctcccgaata    360
ccacatcgtg atgatgcttc agcgcacgga agtcacagac accgcctgta taaaggggg    420 actgtgaccc tgtatgaggc gcaacatggt ctcacagcag ctcacctgaa gaggcttgta    480
agatcaccct ctgtgtattg caccatgatt gtcggcattc tcaccacgct ggctacgctg    540
gccacactcg cagctagtgt gcctctagag gagcggcaag cttgctcaag cgtctggtaa    600
ttatgtgaac cctctcaaga gacccaaata ctgagatatg tcaggggcc aatgtggtgg    660 ccagaattgg tcgggtccga cttgctgtgc ttccggaagc acatgcgtct actccaacga    720
ctattactcc cagtgtcttc ccggcgctgc aagctcaagc tcgtccacgc gcgccgcgtc    780
gacgacttct cgagtatccc ccacaacatc ccggtcgagc tccgcgacgc ctccacctgg    840
ttctactact accagagtac ctccagtcgg atcgggaacc gctacgtatt caggcaaccc    900
ttttgttggg gtcactcctt gggccaatgc atattcgcc tctgaagtta gcagcctcgc    960
tattcctagc ttgactggag ccatggccac tgctgcagca gctgtcgcaa aggttccctc   1020
ttttatgtgg ctgtaggtcc tcccggaacc aaggcaatct gttactgaag gctcatcatt   1080
cactgcagag atactcttga caagacccct ctcatggagc aaaccttggc cgacatccgc   1140
accgccaaca gaatggcgg taactatgcc ggacagtttg tggtgtatga cttgccggat   1200
cgcgattgcg ctgcccttgc ctcgaatggc gaatactcta ttgccgatgg tggcgtcgcc   1260
aaatataaga actatatcga caccattcgt caaattgtcg tggaatattc cgatatccgg   1320
accctcctgg ttattggtga gtttaaacac ctgcctcccc cccccttcc cttcctttcc    1380 cgccggcatc ttgtcgttgt gctaactatt gttccctctt ccagagcctg actctcttgc   1440
caacctggtg accaacctcg gtactccaaa gtgtgccaat gctcagtcag cctaccttga   1500
gtgcatcaac tacgccgtca cacagctgaa ccttccaaat gttgcgatgt atttggacgc   1560
tggccatgca ggatggcttg gctgccggc aaaccaagac ccggccgctc agctatttgc    1620
aaatgtttac aagaatgcat cgtctccgag agctcttcgc ggattggcaa ccaatgtcgc   1680
caactacaac gggtggaaca ttaccagccc ccatcgtac acgcaaggca acgctgtcta   1740
```

```
caacgagaag ctgtacatcc acgctattgg acctcttctt gccaatcacg gctggtccaa    1800
cgccttcttc atcactgatc aaggtcgatc gggaaagcag cctaccggac agcaacagtg    1860
gggagactgg tgcaatgtga tcggcaccgg atttggtatt cgcccatccg caaacactgg    1920
ggactcgttg ctggattcgt ttgtctgggt caagccaggc ggcgagtgtg acggcaccag    1980
cgacagcagt gcgccacgat ttgactccca ctgtgcgctc ccagatgcct gcaaccggc     2040 gcctcaagct ggtgcttggt tccaagccta ctttgtgcag cttctcacaa acgcaaaccc    2100
atcgttcctg taaggctttc gtgaccgggc ttcaaacaat gatgtgcgat ggtgtggttc    2160
ccggttggcg gagtctttgt ctactttggt tgt                                 2193

<210> SEQ ID NO 7
<211> LENGTH: 1590
<212> TYPE: DNA
<213> ORGANISM: Humicola grisea

<400> SEQUENCE: 7
gaattcatga gaaccgctaa gttcgctacc ttggctgcct tggttgcctc tgctgctgct      60
caacaagcct gttccttgac tactgaacgt cacccatctt tgtcttggaa caagtgtact     120
gctggtggtc aatgtcaaac tgtccaagcc tccatcactt tggactctaa ttggagatgg     180
acccaccaag tctctggtag tactaactgt tacaccggta ataagtggga cacttctatt     240
tgtactgacg ctaagtcttg tgctcaaaat tgttgtgttg atggtgctga ttacacctcc     300
acttatggta ttaccaccaa cggtgactct tgtccttga agttcgttac taaaggtcaa      360
cattccacca acgtcggttc tagaacctac ttaatggacg gtgaagacaa gtaccaaacc     420
ttcgaattgt tgggtaatga atttaccttc gatgtcgatg tgtctaacat cggttgtggt     480
ttgaacggtg ctttatactt cgtttctatg gacgccgacg gtggtttgtc tcgttaccca     540
ggtaataagg ctggtgccaa gtatggtacc ggttactgtg atgctcaatg cccaagagac     600
attaagttca tcaacggtga agctaacatt gaaggttgga ctggttctac caacgaccca     660
aacgctggcg ccggtagata cggtacctgt tgttccgaaa tggacatttg gaagccaac      720 aacatggcta ctgcttttac tccacaccca tgtaccatca ttggtcaatc cagatgtgaa     780
ggtgactcct gtggcggtac ctactccaac gaaagatacg ctggtgtttg tgatccagac     840
ggttgtgact caactcccta cagacaaggt aacaagactt tctatggtaa gggtatgact     900
gtcgatacca ccaagaagat caccgtcgtc acccaattct tgaaggacgc taacggtgat     960
ttaggtgaaa ttaaaagatt ctacgtccaa gatggtaaga tcatcccaaa ctctgaatct    1020
accattccag tgttgaagg taattccatc actcaagact ggtgtgacag acaaaaggtt     1080
gccttcggtg atattgacga cttcaacaga aagggtggta tgaagcaaat gggtaaggct    1140
ttggccggtc caatggtctt ggttatgtct atttgggacg atcacgcttc caacatgttg    1200
tggttggact ccaccttccc agttgatgct gctggtaagc caggtgccga agagggtgct    1260
tgtccaacta cttccggtgt cccagctgaa gttgaagccg aagctccaaa ttctaacgtt    1320
gtcttctcta acatcagatt cggtccaatc ggttccacag tcgctggttt gccaggtgct    1380
ggtaatggtg gtaataacgg tggtaaccca ccaccaccaa ccactaccac ttcttctgcc    1440
ccagctacta ccaccaccgc ttctgctggt ccaaaggctg gtagatggca acaatgtggt    1500
ggtattggtt tcaccggtcc aacccaatgt gaagaaccat acatctgtac caagttgaac    1560
gactggtact ctcaatgttt ataactcgag                                     1590
```

<210> SEQ ID NO 8
<211> LENGTH: 1383
<212> TYPE: DNA
<213> ORGANISM: Thermoascus aurantiacus

<400> SEQUENCE: 8

```
gaattcatgt accaaagagc tctattgttc tccttcttct tggccgccgc tagagctcat     60
gaagccggta ctgtcaccgc cgaaaaccac ccatccttga cttggcaaca atgttcctct    120
ggtggttctt gtactactca aaacgggaag gttgttattg acgctaactg agatgggtt     180
cacactacct ccggttacac caactgttac actggtaaca cttgggatac ttccatctgt    240
ccagacgacg ttacctgtgc tcaaaactgt gctttggacg tgctgactga ctccggtact    300
tacggtgtca ctacctctgg caacgcgttg agattgaact tcgtcaccca atcttctggt    360
aagaacatcg gttctagatt gtacttgttg caagacgata ctacttacca aatcttcaag    420
ttgttgggtc aagagttcac tttcgacgtt gatgtttcca acttgccttg tggtttgaac    480
ggtgctttgt acttcgttgc tatggacgcc gacggtaact tatccaagta cccaggtaac    540
aaggccggtg ccaagtacgg taccggttac tgtgattctc aatgtccaag agacctaaaa    600
ttcattaacg gtcaagctaa cgtcgaaggt tggcaaccat ctgctaacga tccaaacgcc    660
ggtgtcggta atcacggttc ctcctgtgct gaaatggacg tttgggaagc taactctatc    720
tccaccgccg tcactccaca tccatgtgat accccaggtc aaaccatgtg tcaaggtgat    780
gattgtggtg gtacctactc ttccactaga tacgctggta cctgtgacac cgacggttgt    840
gatttcaacc cataccaacc aggtaaccac tcttttctacg gtccaggtaa gattgtcgat    900
acttcttcta gttcactgt tgtcactcaa ttcattaccg acgatggtac cccatctggt    960
acccctaactg aaattaagag attctacgtc caaaacggta agtcattcc acaatccgaa   1020
agcaccattt ccggtgttac cggtaactcc atcaccactg aatactgtac cgctcaaaag   1080
gccgcctttg acaaccaccgg tttcttcacc catggtggtt tgcaaaagat ttctcaagcc   1140
ttggctcaag gtatggtttt ggtcatgtcc ttgtgggatg accacgctgc taacatgttg   1200
tggttggatt ctacttaccc aactgacgct gatccagaca ccccaggtgt tgctagaggt   1260
acttgtccaa ccacttctgg tgttccagct gacgtcgaat ctcaaaaccc taactcttac   1320
gttatctact ctaacatcaa ggtgggtcca attaactcca ccttcactgc taactaactc   1380
gag                                                                  1383
```

<210> SEQ ID NO 9
<211> LENGTH: 1379
<212> TYPE: DNA
<213> ORGANISM: Talaromyces emersonii

<400> SEQUENCE: 9

```
gaattcatgc taagaagagc tttactattg agctcttctg ctatcttggc cgttaaggct     60
caacaagccg gtaccgctac tgctgaaaac caccctccat tgacctggca agaatgtacc    120
gctccaggtt cttgtaccac ccaaaacggt gctgtcgtct tggacgctaa ctggagatgg    180
gtccacgact caacggtta cactaactgt tacaccggta cacctgggga cccaacttac    240
tgtccagacg acgaaacttg cgctcaaaac tgtgccttgg acggtgctga ctacgaaggt    300
acttacggtg ttacctcctc tggttcttcc ttgaagttga acttcgtcac tggttctaac    360
gtcggttcca gattgtattt gttgcaagat gactccactt accaaatctt caagttgttg    420
aacagagaat tttctttcga cgtcgatgtg tccaacttgc cttgtggttt gaacggtgct    480
```

```
ctatacttcg ttgctatgga cgctgatggt ggtgtttcca agtacccaaa caacaaggct      540
ggtgccaaat acggtactgg ttactgtgac tctcaatgtc cacgtgactt gaagtttatt      600
gatggtgaag ctaatgtcga aggttggcaa ccatcttcta acaacgctaa cactggcatc      660
ggtgaccacg gttcttgctg tgccgaaatg gacgtttggg aagccaactc catttccaac      720
gccgtcactc cacacccatg tgacactcca ggtcaaacta tgtgttccgg cgatgactgt      780
ggtggtactt actctaacga tagatacgct ggtacctgtg atccagacgg ttgcgacttc      840
aatccataca gaatgggtaa cacttccttt tacggtccag gcaagatcat cgacactact      900
aagccattca ctgttgtcac ccaattcttg accgacgatg gtactgatac cggtactttg      960
tccgaaatca gagattcta catccaaaac tctaacgtca tcccacaacc aaattccgac     1020
atctctggtg tcactggtaa ctccattacc accgaatttt gtaccgccca aaagcaagct     1080
ttcggtgaca ccgacgactt ctctcaacac ggtggtttgg ctaagatggg tgctgctatg     1140
caacaaggta tggttttggt catgtctttg tgggacgact acgctgctca aatgttgtgg     1200
ttggactccg attacccaac cgatgccgac ccaaccaccc ctggtatcgc tagaggtacc     1260
tgtccaactg actctggtgt tccatctgac gtcgaatccc aatctccaaa ctcctacgtc     1320
acttactcca acattaaatt ggtccaatca actccacttt cactgcttct taactcgag      1379

<210> SEQ ID NO 10
<211> LENGTH: 1392
<212> TYPE: DNA
<213> ORGANISM: Talaromyces emersonii

<400> SEQUENCE: 10
gaattcatgc gtaacttgtt ggccttggct ccagccgctt tgttggttgg tgctgccgaa       60
gctcaacaat ccttgtgggg tcaatgcggt ggttcctcct ggactggtgc aacttcctgt      120
gccgctggtg ccacctgttc caccattaac ccatactacg ctcaatgtgt tccagccact      180
gccactccaa ctaccttgac taccaccact aagccaacct ccaccggtgg tgctgctcca      240
accactccac caccaactac taccggtact accacctctc cagtcgtcac cagacctgcc      300
tccgcctccg gtaatccatt cgaaggttat caattgtacg ctaaccctta ctacgcttct      360
gaagtcattt ccttggctat cccatctttg agctccgagt tggtcccaaa ggcctccgaa      420
gttgctaagg tccttcatt tgtctggtta gatcaagctg ccaaggttcc atctatgggt      480
gattacttga aggatattca atctcaaaac gctgctggtg ctgatccacc aatcgccggt      540
attttcgttg tttacgattt gccagataga gactgtgccg ccgctgcttc taacggtgaa      600
ttttctatcg ccaacaacgg tgtcgcttta tacaaacaat atatcgattc cattagagaa      660
caattaacca cttactccga cgtccatacc atcttggtta tcgaaccaga ctctttggct      720
aacgttgtca ctaacttgaa cgttccaaaa tgtgctaacg ctcaagatgc ttacttggaa      780
tgtatcaact acgctattac ccaattggac ttgccaaacg ttgctatgta cttggacgct      840
ggtcacgccg gttggttggg ttggcaagcc aacttggccc cagctgctca attattcgct      900
tctgtttaca gaacgcctc ttccccagcc tctgttagag gtttggctac caacgtggct      960
aactacaacg cctggtccat ttctagatgt ccatcctaca ctcaaggtga cgctaactgt     1020
gatgaagaag attacgttaa cgctttgggt ccattgttcc aagaacaagg tttcccagct     1080
tacttcatca tcgacactc ccgtaacggt gtcagaccaa ctaagcaatc tcaatggggt     1140
gactggtgta acgttattgg taccggtttc ggtgttagac caaccaccga cactggtaac     1200
```

```
ccattggaag acgctttcgt ttgggtcaag ccaggtggtg aatccgacgg tacctccaac    1260
actactagcc cacgttacga ttaccactgt ggtttgtctg acgctttgca accagctcca    1320
gaagctggta cctggttcca agcctacttc gaacaattgt tgactaacgc caacccattg    1380
ttctaactcg ag                                                        1392

<210> SEQ ID NO 11
<211> LENGTH: 525
<212> TYPE: PRT
<213> ORGANISM: Humicola grisea

<400> SEQUENCE: 11

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
                20                  25                  30

Ser Trp Asn Lys Cys Thr Ala Gly Gly Gln Cys Gln Thr Val Gln Ala
            35                  40                  45

Ser Ile Thr Leu Asp Ser Asn Trp Arg Trp Thr His Gln Val Ser Gly
        50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
                100                 105                 110

Phe Val Thr Lys Gly Gln His Ser Thr Asn Val Gly Ser Arg Thr Tyr
            115                 120                 125

Leu Met Asp Gly Glu Asp Lys Tyr Gln Thr Phe Glu Leu Leu Gly Asn
        130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
                180                 185                 190

Ala Gln Cys Pro Arg Asp Ile Lys Phe Ile Asn Gly Glu Ala Asn Ile
            195                 200                 205

Glu Gly Trp Thr Gly Ser Thr Asn Asp Pro Asn Ala Gly Ala Gly Arg
        210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
                260                 265                 270

Gly Val Cys Asp Pro Asp Gly Cys Asp Phe Asn Ser Tyr Arg Gln Gly
            275                 280                 285

Asn Lys Thr Phe Tyr Gly Lys Gly Met Thr Val Asp Thr Thr Lys Lys
        290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
                325                 330                 335
```

-continued

```
Glu Ser Thr Ile Pro Gly Val Glu Gly Asn Ser Ile Thr Gln Asp Trp
            340                 345                 350

Cys Asp Arg Gln Lys Val Ala Phe Gly Asp Ile Asp Asp Phe Asn Arg
        355                 360                 365

Lys Gly Gly Met Lys Gln Met Gly Lys Ala Leu Ala Gly Pro Met Val
    370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
            420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Gly Asn Asn
    450                 455                 460

Gly Gly Asn Pro Pro Pro Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495

Cys Gly Gly Ile Gly Phe Thr Gly Pro Thr Gln Cys Glu Glu Pro Tyr
            500                 505                 510

Ile Cys Thr Lys Leu Asn Asp Trp Tyr Ser Gln Cys Leu
        515                 520                 525

<210> SEQ ID NO 12
<211> LENGTH: 456
<212> TYPE: PRT
<213> ORGANISM: Thermoascus aurantiacus

<400> SEQUENCE: 12

Met Tyr Gln Arg Ala Leu Leu Phe Ser Phe Phe Leu Ala Ala Ala Arg
1               5                   10                  15

Ala His Glu Ala Gly Thr Val Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Thr Ser Gly Tyr
    50                  55                  60

Thr Asn Cys Tyr Thr Gly Asn Thr Trp Asp Thr Ser Ile Cys Pro Asp
65                  70                  75                  80

Asp Val Thr Cys Ala Gln Asn Cys Ala Leu Asp Gly Ala Asp Tyr Ser
                85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
    130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Asn Leu Ser Lys Tyr Pro
                165                 170                 175

Gly Asn Lys Ala Gly Ala Lys Tyr Gly Thr Gly Tyr Cys Asp Ser Gln
            180                 185                 190
```

Cys Pro Arg Asp Leu Lys Phe Ile Asn Gly Gln Ala Asn Val Glu Gly
            195                 200                 205

Trp Gln Pro Ser Ala Asn Asp Pro Asn Ala Gly Val Gly Asn His Gly
    210                 215                 220

Ser Ser Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Thr Asp Gly Cys Asp Phe Asn Pro Tyr Gln Pro Gly Asn His
            275                 280                 285

Ser Phe Tyr Gly Pro Gly Lys Ile Val Asp Thr Ser Ser Lys Phe Thr
    290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Asp Asn Thr Gly Phe Phe Thr
    355                 360                 365

His Gly Gly Leu Gln Lys Ile Ser Gln Ala Leu Ala Gln Gly Met Val
    370                 375                 380

Leu Val Met Ser Leu Trp Asp Asp His Ala Ala Asn Met Leu Trp Leu
385                 390                 395                 400

Asp Ser Thr Tyr Pro Thr Asp Ala Asp Pro Asp Thr Pro Gly Val Ala
                405                 410                 415

Arg Gly Thr Cys Pro Thr Thr Ser Gly Val Pro Ala Asp Val Glu Ser
            420                 425                 430

Gln Asn Pro Asn Ser Tyr Val Ile Tyr Ser Asn Ile Lys Val Gly Pro
    435                 440                 445

Ile Asn Ser Thr Phe Thr Ala Asn
    450                 455

<210> SEQ ID NO 13
<211> LENGTH: 455
<212> TYPE: PRT
<213> ORGANISM: Talaromyces emersonii

<400> SEQUENCE: 13

Met Leu Arg Arg Ala Leu Leu Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn

```
                100             105             110
Phe Val Thr Gly Ser Asn Val Gly Ser Arg Leu Tyr Leu Leu Gln Asp
            115                 120                 125

Asp Ser Thr Tyr Gln Ile Phe Lys Leu Leu Asn Arg Glu Phe Ser Phe
        130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser
    450                 455

<210> SEQ ID NO 14
<211> LENGTH: 459
<212> TYPE: PRT
<213> ORGANISM: Talaromyces emersonii

<400> SEQUENCE: 14

Met Arg Asn Leu Leu Ala Leu Ala Pro Ala Ala Leu Leu Val Gly Ala
1               5                   10                  15
```

```
Ala Glu Ala Gln Gln Ser Leu Trp Gly Gln Cys Gly Gly Ser Ser Trp
             20                  25                  30

Thr Gly Ala Thr Ser Cys Ala Ala Gly Ala Thr Cys Ser Thr Ile Asn
 35                  40                  45

Pro Tyr Tyr Ala Gln Cys Val Pro Ala Thr Ala Thr Pro Thr Thr Leu
 50                  55                  60

Thr Thr Thr Thr Lys Pro Thr Ser Thr Gly Gly Ala Ala Pro Thr Thr
65                  70                  75                  80

Pro Pro Pro Thr Thr Thr Gly Thr Thr Thr Ser Pro Val Val Thr Arg
                 85                  90                  95

Pro Ala Ser Ala Ser Gly Asn Pro Phe Glu Gly Tyr Gln Leu Tyr Ala
             100                 105                 110

Asn Pro Tyr Tyr Ala Ser Glu Val Ile Ser Leu Ala Ile Pro Ser Leu
         115                 120                 125

Ser Ser Glu Leu Val Pro Lys Ala Ser Glu Val Ala Lys Val Pro Ser
     130                 135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                 165                 170                 175

Ala Gly Ile Phe Val Val Tyr Asp Leu Pro Asp Arg Asp Cys Ala Ala
             180                 185                 190

Ala Ala Ser Asn Gly Glu Phe Ser Ile Ala Asn Asn Gly Val Ala Leu
         195                 200                 205

Tyr Lys Gln Tyr Ile Asp Ser Ile Arg Glu Gln Leu Thr Thr Tyr Ser
     210                 215                 220

Asp Val His Thr Ile Leu Val Ile Glu Pro Asp Ser Leu Ala Asn Val
225                 230                 235                 240

Val Thr Asn Leu Asn Val Pro Lys Cys Ala Asn Ala Gln Asp Ala Tyr
                 245                 250                 255

Leu Glu Cys Ile Asn Tyr Ala Ile Thr Gln Leu Asp Leu Pro Asn Val
             260                 265                 270

Ala Met Tyr Leu Asp Ala Gly His Ala Gly Trp Leu Gly Trp Gln Ala
         275                 280                 285

Asn Leu Ala Pro Ala Ala Gln Leu Phe Ala Ser Val Tyr Lys Asn Ala
     290                 295                 300

Ser Ser Pro Ala Ser Val Arg Gly Leu Ala Thr Asn Val Ala Asn Tyr
305                 310                 315                 320

Asn Ala Trp Ser Ile Ser Arg Cys Pro Ser Tyr Thr Gln Gly Asp Ala
                 325                 330                 335

Asn Cys Asp Glu Glu Asp Tyr Val Asn Ala Leu Gly Pro Leu Phe Gln
             340                 345                 350

Glu Gln Gly Phe Pro Ala Tyr Phe Ile Ile Asp Thr Ser Arg Asn Gly
         355                 360                 365

Val Arg Pro Thr Lys Gln Ser Gln Trp Gly Asp Trp Cys Asn Val Ile
     370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
                 405                 410                 415

Ser Asn Thr Thr Ser Pro Arg Tyr Asp Tyr His Cys Gly Leu Ser Asp
             420                 425                 430

Ala Leu Gln Pro Ala Pro Glu Ala Gly Thr Trp Phe Gln Ala Tyr Phe
```

```
                    435                 440                 445
Glu Gln Leu Leu Thr Asn Ala Asn Pro Leu Phe
            450                 455

<210> SEQ ID NO 15
<211> LENGTH: 1608
<212> TYPE: DNA
<213> ORGANISM: Trichoderma reesei

<400> SEQUENCE: 15
atggtctcct tcacctccct gctggccggc gttgccgcta tctctggtgt cctagcagcc      60
cctgccgcag aagttgaacc tgtcgcagtt gagaaacgtg aggccgaagc agaagctcaa     120
tccgcttgta ccctacaatc cgaaactcac ccaccattga cctggcaaaa gtgttctagc     180
ggtggaactt gtactcaaca aactggttct gttgttatcg acgctaactg agatggaca      240 cacgccacta actcttctac caactgttac gacggtaaca cttggtcttc cactttatgt     300
ccagataacg aaacttgtgc taagaattgc tgtttggacg gtgccgccta cgcttctacc     360
tacggtgtta ccacctccgg taactccttg tctattggtt cgtcactca atccgctcaa      420 aagaacgttg gtgctagatt gtacttgatg cttctgaca ctacttatca agaatttact      480
ttgttgggta acgaattttc tttcgatgtt gacgtttccc aattgccatg tggcttgaac     540
ggtgctttgt actttgtctc tatggatgct gacggtggtg tttctaagta cccaactaac     600
actgccggtg ctaagtacgg tactggttac tgtgattctc aatgtccacg tgacttgaag     660
ttcattaacg gtcaagccaa cgtcgaaggt tgggaaccat cctccaacaa cgctaacacc     720
ggtatcggtg gtcacggttc ctgttgttcc gaaatggaca tctgggaagc taacagtatt     780
tctgaagctt tgacaccaca cccatgcacc actgtcggtc aagaaatttg tgaaggtgat     840
ggatgtggtg gaacctactc tgataacaga tacggtggta cttgtgaccc agacggttgt     900
gactggaacc catacagatt gggtaacact tctttctatg gtccaggttc ttctttcacc     960
ttggatacca ccaagaagtt gactgttgtt acccaattcg aaacttctgg tgctatcaac    1020
agatactacg ttcaaaacgg tgtcaccttc aacaaccaa cgctgaatt gggttcttac    1080 tctggtaatg aattgaacga cgactactgt accgctgaag aagctgaatt tggtggttcc    1140
tctttctccg acaagggtgg tttgacccaa ttcaagaagg ctacctccgg tggtatggtt    1200
ttggttatgt ccttgtggga tgattactac gcaaacatgt tatggttaga cagtacttac    1260
ccaactaacg aaacctcctc tactccaggt gctgtcagag ttcctgttc tacctcttct     1320 ggtgttccag ctcaagttga atctcaatct ccaaacgcta aggtcacttt ctccaacatc    1380
aagttcggtc aatcggttc cactggtaat ccatctggtg aaaccctcc aggtggtaac     1440 agaggtacta ccactactcg taggccagct actacaactg ttcttcccc aggcccaacc    1500 caatcccact acggtcaatg tggtggtatc ggttactctg gtccaaccgt ctgtgcttct    1560
ggtactacct gtcaagtttt aaacccatac tactctcaat gtttgtaa                 1608

<210> SEQ ID NO 16
<211> LENGTH: 1479
<212> TYPE: DNA
<213> ORGANISM: Trichoderma reesei

<400> SEQUENCE: 16
atggtctcct tcacctccct gctggccggc gttgccgcta tctctggtgt cctagcagcc      60
cctgccgcag aagttgaacc tgtcgcagtt gagaaacgtg aggccgaagc agaagctgtc     120
```

-continued

```
ccattagaag aaagacaagc ctgctcctct gtttgggtc aatgtggtgg tcaaaactgg      180
tctggtccaa cttgttgtgc ttccggttct acctgtgttt actccaacga ctactattcc     240
caatgtttgc caggtgctgc ttcctcttcc tcttcaacta gagctgcttc tacaacttct     300
agggtctccc caaccacttc cagatcctct tctgctactc caccaccagg ttctactacc     360
actagagttc caccagtcgg ttccggtact gctacttact ctggtaaccc tttcgtcggt     420
gttactccat gggctaacgc ttactacgct tctgaagttt cttctttggc tatcccatct     480
ttgactggtg ctatggctac cgctgctgct gctgtcgcca agttccatc cttcatgtgg      540
ttggacacct tggacaaaac tccattaatg aacaaacct tggcagacat aaggactgct      600
aacaagaacg gcggtaacta cgctggtcaa tttgttgtgt acgacttgcc agacagagac     660
tgtgctgctt ggcttccaa cggtgaatac tccatcgctg acggtggtgt cgccaagtac      720
aagaactaca ttgataccat tagacaaatc gttgtcgaat actctgacat cagaaccttg     780
ttagtcatcg aaccagattc tttagccaat ttagtcacca acttgggtac tccaaagtgt    840
gctaacgctc aatctgccta cttagaatgt atcaattatg cagttaccca attgaacttg     900
ccaaacgttg ctatgtactt ggacgctggt cacgccggtt ggttgggttg ccagctaac      960
caagacccag ccgctcaatt attcgccaac gtttacaaga atgcctcttc tcctagagcc    1020
ttgcgtggtt tggctactaa cgtcgctaac tacaacggtt ggaacatcac ttctccacca    1080
tcttacaccc aaggtaacgc tgtttacaac gaaaagttgt acattcacgc tatcggtcca    1140
ttattggcta accatggttg gtctaacgcc ttcttcatca ccgaccaagg tagatccggt    1200
aaacaaccaa ctggtcaaca caatgggggt gattggtgta acgtcatcgg tactggtttc    1260
ggtatcagac catccgctaa cactggtgat tccttgttgg attccttcgt ctgggttaag    1320
ccaggtggtg aatgtgatgg cacctctgat tcctctgctc caagattcga ttcccactgc    1380
gccttgccag acgctttgca accagcccca caagctggtg catggttcca agcttacttt    1440
gtccaattgt tgaccaacgc taacccatct ttcttgtaa                            1479
```

<210> SEQ ID NO 17
<211> LENGTH: 535
<212> TYPE: PRT
<213> ORGANISM: Trichoderma reesei

<400> SEQUENCE: 17

```
Met Val Ser Phe Thr Ser Leu Leu Ala Gly Val Ala Ala Ile Ser Gly
1               5                   10                  15

Val Leu Ala Ala Pro Ala Glu Val Glu Pro Val Ala Val Glu Lys
            20                  25                  30

Arg Glu Ala Glu Ala Glu Ala Gln Ser Ala Cys Thr Leu Gln Ser Glu
        35                  40                  45

Thr His Pro Pro Leu Thr Trp Gln Lys Cys Ser Ser Gly Gly Thr Cys
    50                  55                  60

Thr Gln Gln Thr Gly Ser Val Val Ile Asp Ala Asn Trp Arg Trp Thr
65                  70                  75                  80

His Ala Thr Asn Ser Ser Thr Asn Cys Tyr Asp Gly Asn Thr Trp Ser
                85                  90                  95

Ser Thr Leu Cys Pro Asp Asn Glu Thr Cys Ala Lys Asn Cys Cys Leu
            100                 105                 110

Asp Gly Ala Ala Tyr Ala Ser Thr Tyr Gly Val Thr Thr Ser Gly Asn
        115                 120                 125

Ser Leu Ser Ile Gly Phe Val Thr Gln Ser Ala Gln Lys Asn Val Gly
```

```
            130                 135                 140
Ala Arg Leu Tyr Leu Met Ala Ser Asp Thr Thr Tyr Gln Glu Phe Thr
145                 150                 155                 160

Leu Leu Gly Asn Glu Phe Ser Phe Asp Val Asp Val Ser Gln Leu Pro
                165                 170                 175

Cys Gly Leu Asn Gly Ala Leu Tyr Phe Val Ser Met Asp Ala Asp Gly
            180                 185                 190

Gly Val Ser Lys Tyr Pro Thr Asn Thr Ala Gly Ala Lys Tyr Gly Thr
                195                 200                 205

Gly Tyr Cys Asp Ser Gln Cys Pro Arg Asp Leu Lys Phe Ile Asn Gly
        210                 215                 220

Gln Ala Asn Val Glu Gly Trp Glu Pro Ser Ser Asn Asn Ala Asn Thr
225                 230                 235                 240

Gly Ile Gly Gly His Gly Ser Cys Cys Ser Glu Met Asp Ile Trp Glu
            245                 250                 255

Ala Asn Ser Ile Ser Glu Ala Leu Thr Pro His Pro Cys Thr Thr Val
            260                 265                 270

Gly Gln Glu Ile Cys Glu Gly Asp Gly Cys Gly Gly Thr Tyr Ser Asp
        275                 280                 285

Asn Arg Tyr Gly Gly Thr Cys Asp Pro Asp Gly Cys Asp Trp Asn Pro
290                 295                 300

Tyr Arg Leu Gly Asn Thr Ser Phe Tyr Gly Pro Gly Ser Ser Phe Thr
305                 310                 315                 320

Leu Asp Thr Thr Lys Lys Leu Thr Val Val Thr Gln Phe Glu Thr Ser
                325                 330                 335

Gly Ala Ile Asn Arg Tyr Tyr Val Gln Asn Gly Val Thr Phe Gln Gln
            340                 345                 350

Pro Asn Ala Glu Leu Gly Ser Tyr Ser Gly Asn Glu Leu Asn Asp Asp
            355                 360                 365

Tyr Cys Thr Ala Glu Glu Ala Glu Phe Gly Gly Ser Ser Phe Ser Asp
        370                 375                 380

Lys Gly Gly Leu Thr Gln Phe Lys Lys Ala Thr Ser Gly Gly Met Val
385                 390                 395                 400

Leu Val Met Ser Leu Trp Asp Asp Tyr Tyr Ala Asn Met Leu Trp Leu
                405                 410                 415

Asp Ser Thr Tyr Pro Thr Asn Glu Thr Ser Ser Thr Pro Gly Ala Val
                420                 425                 430

Arg Gly Ser Cys Ser Thr Ser Ser Gly Val Pro Ala Gln Val Glu Ser
            435                 440                 445

Gln Ser Pro Asn Ala Lys Val Thr Phe Ser Asn Ile Lys Phe Gly Pro
        450                 455                 460

Ile Gly Ser Thr Gly Asn Pro Ser Gly Gly Asn Pro Pro Gly Gly Asn
465                 470                 475                 480

Arg Gly Thr Thr Thr Thr Arg Arg Pro Ala Thr Thr Thr Gly Ser Ser
                485                 490                 495

Pro Gly Pro Thr Gln Ser His Tyr Gly Gln Cys Gly Gly Ile Gly Tyr
            500                 505                 510

Ser Gly Pro Thr Val Cys Ala Ser Gly Thr Thr Cys Gln Val Leu Asn
            515                 520                 525

Pro Tyr Tyr Ser Gln Cys Leu
    530                 535

<210> SEQ ID NO 18
```

```
<211> LENGTH: 471
<212> TYPE: PRT
<213> ORGANISM: Trichoderma reesei

<400> SEQUENCE: 18

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
```

```
                385                 390                 395                 400
Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
                420                 425                 430

Pro Arg Phe Asp Ser His Cys Ala Leu Pro Asp Ala Leu Gln Pro Ala
            435                 440                 445

Ala Gln Ala Gly Ala Trp Phe Gln Ala Tyr Phe Val Gln Leu Leu Thr
        450                 455                 460

Asn Ala Asn Pro Ser Phe Leu
465                 470

<210> SEQ ID NO 19
<211> LENGTH: 148
<212> TYPE: DNA
<213> ORGANISM: Artificial Sequence
<220> FEATURE:
<223> OTHER INFORMATION: Synthetic xyn2 secretion signal

<400> SEQUENCE: 19
gaattcttaa ttaaaaacaa aatggtctcc ttcacctccc tgctggccgg cgttgccgct      60
atctctggtg tcctagcagc ccctgccgca gaagttgaac ctgtcgcagt tgagaaacgt     120
gaggccgaag cagaagctcc cgggactc                                        148

<210> SEQ ID NO 20
<211> LENGTH: 39
<212> TYPE: PRT
<213> ORGANISM: Artificial Sequence
<220> FEATURE:
<223> OTHER INFORMATION: Synthetic xyn2 secretion signal

<400> SEQUENCE: 20

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Glu Ala Glu Ala Glu Ala
        35
```